US010961358B2

(12) United States Patent
Iwamura et al.

(10) Patent No.: US 10,961,358 B2
(45) Date of Patent: Mar. 30, 2021

(54) WATER-ABSORBING RESIN COMPOSITION

(71) Applicant: NIPPON SHOKUBAI CO., LTD., Osaka (JP)

(72) Inventors: Taku Iwamura, Hyogo (JP); Yasuhisa Nakajima, Hyogo (JP); Kazushi Torii, Hyogo (JP); Taku Fujimoto, Hyogo (JP); Hiroki Kawada, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 128 days.

(21) Appl. No.: 16/336,609

(22) PCT Filed: Sep. 29, 2017

(86) PCT No.: PCT/JP2017/035663
§ 371 (c)(1),
(2) Date: Mar. 26, 2019

(87) PCT Pub. No.: WO2018/062539
PCT Pub. Date: Apr. 5, 2018

(65) Prior Publication Data
US 2019/0338082 A1 Nov. 7, 2019

(30) Foreign Application Priority Data
Sep. 30, 2016 (JP) .............................. JP2016-194827

(51) Int. Cl.
*A61L 15/22* (2006.01)
*C08J 3/075* (2006.01)
*A61L 15/48* (2006.01)
*C08K 5/09* (2006.01)

(52) U.S. Cl.
CPC ............ *C08J 3/075* (2013.01); *A61L 15/22* (2013.01); *A61L 15/48* (2013.01); *C08K 5/09* (2013.01); *C08J 2300/12* (2013.01)

(58) Field of Classification Search
CPC ... A61L 15/22; A61L 5/48; C08J 3/075; C08J 2300/12; C08K 5/09
USPC ....................................................... 502/402
See application file for complete search history.

(56) References Cited

U.S. PATENT DOCUMENTS

| 2002/0120074 | A1 | 8/2002 | Wada et al. |
| 2003/0176589 | A1 | 9/2003 | Wada et al. |
| 2004/0181031 | A1 | 9/2004 | Nogi et al. |
| 2005/0209352 | A1 | 9/2005 | Dairoku et al. |
| 2005/0272600 | A1 | 12/2005 | Wada et al. |
| 2007/0041796 | A1 | 2/2007 | Irie et al. |
| 2007/0066167 | A1 | 3/2007 | Wada et al. |
| 2007/0141338 | A1 | 6/2007 | Ishizaki et al. |
| 2008/0269372 | A1 | 10/2008 | Dairoku et al. |
| 2010/0072421 | A1 | 3/2010 | Kitano et al. |
| 2010/0240808 | A1 | 9/2010 | Wada et al. |
| 2011/0088806 | A1 | 4/2011 | Nogi et al. |
| 2012/0189861 | A1 | 7/2012 | Matsumoto et al. |
| 2012/0298915 | A1 | 11/2012 | Okuda et al. |
| 2014/0031473 | A1 | 1/2014 | Nogi et al. |
| 2014/0042364 | A1 | 2/2014 | Nogi et al. |
| 2014/0371400 | A1 | 12/2014 | Tachi et al. |
| 2015/0218341 | A1 | 8/2015 | Nakashima et al. |

FOREIGN PATENT DOCUMENTS

| CN | 1530384 | A | 9/2004 |
| CN | 1916032 | A | 2/2007 |
| CN | 101627086 | A | 1/2010 |
| CN | 102549028 | A | 7/2012 |
| JP | 2009154155 | A | 7/2009 |
| JP | 2012143755 | A | 8/2012 |
| JP | 2014073448 | A | 4/2014 |
| JP | 2015120933 | A | 7/2015 |
| WO | 2005075070 | A1 | 8/2005 |
| WO | 2009048145 | A1 | 4/2009 |
| WO | 2011099586 | A1 | 8/2011 |
| WO | 2012102406 | A1 | 8/2012 |
| WO | 2012133734 | A1 | 10/2012 |
| WO | 2014034667 | A1 | 3/2014 |

OTHER PUBLICATIONS

International Search Report for PCT Application No. PCT/JP2017/035663 dated Dec. 12, 2017.
International Preliminary Report on Patentability for PCT Application No. PCT/JP2017/035663 dated Apr. 2, 2019.
Extended European Search Report for EP Application No. 17856486.0 dated Oct. 8, 2019.
Office Action from corresponding Chinese Application No. 201780074008.4 dated Nov. 4, 2020.

*Primary Examiner* — Edward M Johnson
(74) *Attorney, Agent, or Firm* — Harness Dickey & Pierce P.L.C.

(57) ABSTRACT

To provide a water-absorbing resin composition having both a high centrifuge retention capacity (CRC) and a sufficient urine resistance and a method for producing such a water-absorbing resin composition, an aspect of the present invention is a water-absorbing resin composition having the following properties: (1) A centrifuge retention capacity (CRC) being not less than 35 g/g; (2) A post-degradation-test one-hour eluted soluble component being not more than 19% by mass; (3) An absorbency against pressure 0.7 psi (AAP0.7) being not less than 10 g/g; and (4) A content of a water-absorbing resin in dust being not more than 300 ppm with respect to a total mass of the water-absorbing resin composition.

11 Claims, No Drawings

WATER-ABSORBING RESIN COMPOSITION

PRIORITY STATEMENT

This application is a national stage application under 35 U.S.C. § 371 of PCT International Application No. PCT/JP2017/035663, which has an international filing date of 29 Sep. 2017 and claims priority under 35 U.S.C. § 119 to Japanese Patent Application No. 2016-194827 filed on 30 Sep. 2016. The contents of each application recited above are incorporated herein by reference in their entirety.

TECHNICAL FIELD

The present invention relates to a water-absorbing resin composition and a method for producing a water-absorbing resin composition. The present invention more particularly relates to a water-absorbing resin composition having an excellent urine resistance and a method for producing a water-absorbing resin composition having an excellent urine resistance.

BACKGROUND ART

As a sanitary material for a disposable diaper, a sanitary napkin, an incontinence pad, and the like, a water-absorbing resin composition including a water-absorbing resin as a main component is widely used for the purpose of absorbing a body fluid.

In recent years, such sanitary materials have increasingly higher performance. Research and development are being carried out in which a surfactant and/or an ion sealing agent, for example, is added to impart various functions to a water-absorbing resin composition.

Patent Literature 1, for example, discloses a method for producing a water-absorbing agent, the method including adding a surface-treating agent including (A) a surface-crosslinking agent and (B) a surfactant or a lubricant powder to a water-absorbing resin for surface-crosslinking the water-absorbing resin, as a method for achieving a high fluidity and a high water absorption performance and reducing a decrease caused in the surface tension of an absorption liquid when the water-absorbing agent comes into contact with the absorption liquid.

Patent Literature 2 discloses a method for producing a water-absorbing agent, the method including adding water and a chelating agent to a surface-crosslinked water-absorbing resin for granulation, as a method for producing a urine-resistant water-absorbing agent, that is, a water-absorbing agent that is not easily degraded as a result of urine absorption.

Patent Literatures 3, 4, and 5 each disclose a method for producing a water-absorbing agent, the method including adding a surfactant and a chelating agent after a surface-crosslinking step.

CITATION LIST

Patent Literature

[Patent Literature 1]
International Publication No. 2005/075070 pamphlet (Publication Date: Aug. 18, 2005)
[Patent Literature 2]
Japanese Patent Application Publication, Tokukai, No. 2009-154155 (Publication Date: Jul. 16, 2009)
[Patent Literature 3]
Japanese Patent Application Publication, Tokukai, No. 2014-073448 (Publication Date: Apr. 24, 2014)
[Patent Literature 4]
International Publication No. 2012/133734 pamphlet (Publication Date Apr. 10, 2012)
[Patent Literature 5]
International Publication No. 2009/048145 pamphlet (Publication Date: Apr. 16, 2009)

SUMMARY OF INVENTION

Technical Problem

Conventional art such as the above unfortunately involves the following issue: A water-absorbing resin composition having a high centrifuge retention capacity (CRC) fails to have a sufficient urine resistance.

The present invention has been accomplished in view of the above issue. It is an object of the present invention to provide a water-absorbing resin composition that has, for example, a reduced re-wet, a shortened liquid absorbing time, and a reduced stickiness and that is suitable for use in a diaper. Another object of the present invention is to provide a water-absorbing resin composition having both a high centrifuge retention capacity (CRC) and a sufficient urine resistance and a method for producing such a water-absorbing resin composition.

Solution to Problem

An aspect of the present invention is a water-absorbing resin composition having the following properties:
(1) A centrifuge retention capacity (CRC) being not less than 35 g/g;
(2) A post-degradation-test one-hour eluted soluble component being not more than 19% by mass;
(3) An absorbency against pressure 0.7 psi (AAP0.7) being not less than 10 g/g; and
(4) A content of a water-absorbing resin in dust being not more than 300 ppm with respect to a total mass of the water-absorbing resin composition.

Advantageous Effects of Invention

A water-absorbing resin composition in accordance with an embodiment of the present invention allows a reduced re-wet, a shortened liquid absorbing time, and a reduced stickiness when used in a diaper. Further, a method in accordance with an embodiment of the present invention for producing a water-absorbing resin composition imparts both a high centrifuge retention capacity (CRC) and a sufficient urine resistance to a water-absorbing resin composition.

DESCRIPTION OF EMBODIMENTS

The following description will discuss an embodiment of the present invention. The present invention is, however, not limited to the embodiment.

In the present specification, any numerical range "A to B" means "not less than A and not more than B".

A method in accordance with an embodiment of the present invention for producing a water-absorbing resin composition is a method for producing a water-absorbing resin composition having a centrifuge retention capacity (CRC) of not less than 35 g/g, the method including adding a surfactant and/or a lubricant and a chelating agent to water-absorbing resin particles.

The inventors of the present invention disclosed the following knowledge in the basic application (Tokugan 2016-19482) for the present application.

A production method in accordance with an embodiment of the present invention includes adding, together with a chelating agent (which imparts urine resistance to a water-absorbing resin), a surfactant and/or a lubricant, neither of which produces the effect of improving the urine resistance (that is, decreasing the amount of a post-degradation-test one-hour eluted soluble component). This allows the urine resistance of the water-absorbing resin composition to be improved more than in a case where only a chelating agent has been added.

In contrast, Patent Literature 1 discusses a water-absorbing resin having a low centrifuge retention capacity (CRC) of not more than 34 g/g. Patent Literature 1 thus does not disclose knowledge on a water-absorbing resin having a high centrifuge retention capacity (CRC), for which the present invention is intended. Patent Literature neither teaches nor suggests the above-described synergistic effect for the urine resistance.

Patent Literature 2 discloses adding a chelating agent to a water-absorbing resin having a high centrifuge retention capacity (CRC) to produce the effect of improving the urine resistance. However, the effect of improving the urine resistance produced by an ion sealing agent (that is, a chelating agent) alone is insufficient.

The inventors of the present invention have discovered that adding a surfactant and/or a lubricant and a chelating agent to water-absorbing resin particles allows the post-degradation-test one-hour eluted soluble component to be reduced significantly (stated differently, the urine resistance to be improved significantly) as compared to a case where only a chelating agent has been added to water-absorbing resin particles. In view of the fact that a surfactant and/or a lubricant itself does not produce the effect of improving the urine resistance, it is surprising how the combined use of a surfactant and/or a lubricant and a chelating agent produces the synergistic effect for the urine resistance.

Such a synergistic effect is produced presumably for the following reason: A water-absorbing resin having a high centrifuge retention capacity (CRC) has a low polymer crosslinking density. Even a small degree of degradation (that is, polymer chain breakage) tends to increase the soluble component (that is, decrease the urine resistance). An increase of the soluble component undesirably leads to, for example, stickiness of a diaper. One method for preventing such degradation of a water-absorbing resin is addition of a chelating agent.

The inventors of the present invention have discovered the following issue with conventional art: In a case where a water-absorbing resin composition includes a large amount of fine powder of water-absorbing resin and a large amount of dust of the water-absorbing resin, adding a chelating agent unfortunately results in a major portion of the chelating agent being distributed on such fine powder and dust, each of which has a large particle surface area per unit weight. Assuming, for instance, that a water-absorbing resin composition includes spherical water-absorbing resin particles, reducing the particle diameter r by half results in a two-fold increase in the surface area of the water-absorbing resin composition per unit weight (g). Water-absorbing resin particles, which have relatively large particle diameters, have relatively small surface areas per unit weight. This causes the chelating agent to be distributed on the water-absorbing resin particles in only a small amount, with the result of a failure to produce a desired effect with the chelating agent.

For an example water-absorbing resin composition of the present invention and an example method for producing a water-absorbing resin composition, adding a surfactant and/or a lubricant reduces damage (process damage) such as breakage of the surfaces of water-absorbing resin particles during the production process. This reduces the amount of fine powder and dust generated, and in turn allows the chelating agent to be distributed in a large amount on water-absorbing resin particles, which have large particle diameters. This presumably allows the above synergistic effect to be produced as a result.

The chelating agent added is present on the surfaces of water-absorbing resin particles. Fine powder and dust generated by process damage tend to result from breakage of the surface of the water-absorbing resin. This tendency and other factors lead to a tendency that water-absorbing resin particles having small particle diameters contain a large amount of the chelating agent.

Further, since fine powder and dust of water-absorbing resin themselves each have a large particle surface area per unit weight, a soluble component is easily eluted from the fine powder and dust. The amount of fine powder and dust of water-absorbing resin being large itself leads to a decrease in the urine resistance.

In view of the above knowledge, the inventors of the present invention have, for a water-absorbing resin composition in accordance with an embodiment of the present invention, uniquely considered the amount of fine powder and dust as a factor that can contribute to improvement in the urine resistance.

For a typical process of producing a water-absorbing resin having a high CRC, particles to be subjected to a pulverizing step tend to have large particle diameters. Thus, producing a water-absorbing resin having a predetermined average particle diameter requires pulverization involving a strong pulverization energy or a long-time pulverization. This results in a large process damage, increasing the amount of fine powder and dust and leading to a decrease in the urine resistance.

As described above, the inventors of the present invention have, in relation to Patent Literatures 1 to 5, considered the amount of fine powder and dust (which has not at all been considered in conventional art) and discovered that the content of water-absorbing resin in dust in a water-absorbing resin composition influences the urine resistance, and have thereby completed the present invention.

The amount of fine powder and dust generated can be reduced by a method of adding a surfactant and/or a lubricant ((1) below) as well as by a method of (2) below or a method of (3) below. These methods can be combined with each other.

(1) Reduction of process damage: A surfactant and/or a lubricant is used during a process of producing water-absorbing resin particles to reduce process damage. This reduces the amount of fine powder and dust generated.

(2) Removal of fine powder and dust generated: Water-absorbing resin particles are subjected to additional classification steps (namely, second and third classification steps) for removal of fine powder and dust generated.

(3) A predetermined amount of a plasticizing agent (in particular, water) is added or contained for prevention of dust on the water-absorbing resin.

The inventors of the present invention have discovered that a water-absorbing resin composition which is produced by a method including one or more of (1) to (3) above and to which a chelating agent has been added (stated differently, a water-absorbing resin composition containing only a small amount of fine powder and dust) has both a high CRC and an excellent urine resistance, thereby completing the present invention.

A water-absorbing resin having a low CRC (for example, less than 35 g/g) has a high polymer crosslinking density, and does not suffer much from stickiness caused by polymer degradation. However, in a case where a water-absorbing resin composition including a low-CRC water-absorbing resin is used for a sanitary product (for example, a diaper), the water-absorbing resin composition will be needed in a large amount for a sufficient amount of liquid absorption. Such a water-absorbing resin composition is not preferable in terms of cost.

[1] Definitions of Terms (1-1) Water-Absorbing Resin Composition

The term "water-absorbing resin composition" as used in the present specification refers to an agent for gelling a water-based liquid, the agent including water-absorbing resin particles as a main component (preferably not less than 60% by mass, more preferably not less than 80% by mass, even more preferably not less than 90% by mass, of the water-absorbing resin composition as a whole, with an upper limit of 100% by mass).

For the present invention, the word "composition" is used even in a case where a water-absorbing resin accounts for 100% by mass, as long as it satisfies the requirements of the present invention. The water-absorbing resin composition may contain, as another component(s), water, an inorganic fine particle, a cationic polymer compound, a water-soluble polyvalent metal cation-containing compound, an anti-coloring agent, a urine resistance improver, a deodorant agent, a perfume, an antibacterial agent, a foaming agent, a pigment, a dye, a fertilizer, an oxidizing agent, a reducing agent, and/or the like each in an amount of not less than 0% by mass and not more than 10% by mass, preferably not less than 0.1% by mass and not more than 1% by mass.

A water-absorbing resin composition in accordance with an embodiment of the present invention preferably contains water-absorbing resin particles as a main component (that is, in an amount within a range of 60% by mass to 100% by mass). The water-absorbing resin composition preferably further contains one or more, or two or more, of a chelating agent described later, a surfactant and/or a lubricant, water, and a polyvalent metal salt and/or an inorganic fine particle. In a case where the water-absorbing resin composition contains another compound(s), the content of water-absorbing resin has an upper limit of less than 100%. The shape of the water-absorbing resin composition is not limited, but is preferably in particulate form. In other words, the water-absorbing resin composition is a particulate water-absorbing resin composition in which water-absorbing resin particles contain various additives (preferably in an integrated manner). The term "particulate water-absorbing resin composition" as used in the present specification refers to a water-absorbing resin composition in particulate form.

(1-2) Water-Absorbing Resin Particles

The term "water-absorbing resin particles" as used in the present specification refers to a particulate water-absorbing resin, and covers any particulate water-absorbing resin present during a process of producing a water-absorbing resin composition. The term "water-absorbing resin particles" can thus refer to, for example, all of a particulate crosslinked hydrogel polymer generated during a polymerization step, a particulate crosslinked hydrogel polymer obtained through a gel-crushing step, a dried particulate crosslinked hydrogel polymer (dry polymer) obtained through a drying step, a pulverized particulate dry polymer obtained through a pulverizing step, a particulate water-absorbing resin obtained through a classification step and having adjusted particle sizes, and a surface-crosslinked particulate water-absorbing resin. The term "particulate" as used in the present specification refers to a pulverized non-uniform shape, a spherical shape, a fibrous shape, a bar shape, a substantially spherical shape, and a flat shape. The term "water-absorbing resin" refers to a water-swellable, water-insoluble polymer gelling agent. The term "water-swellable" indicates that the centrifuge retention capacity (CRC) as defined in ERT 441.2-02 is not less than 5 g/g. The term "water-insoluble" indicates that the water-soluble component (Extr) as defined in ERT 470.2-02 is not less than 0% by mass and not more than 50% by mass.

(1-3) CRC

The term "CRC" as used in the present specification stands for and means "centrifuge retention capacity". The term "centrifuge retention capacity" is the same in meaning as "absorption capacity without load". The term "CRC" as used in the present specification indicates a value as measured in conformity with an EDANA method (ERT 441.2-02). A method in accordance with an embodiment of the present invention for producing a water-absorbing resin composition is a method for producing a water-absorbing resin composition having a centrifuge retention capacity (CRC) of not less than 35 g/g.

[2] Surfactant and/or Lubricant

A method in accordance with an embodiment of the present invention for producing a water-absorbing resin composition includes adding a surfactant and/or a lubricant and a chelating agent to water-absorbing resin particles. Stated differently, a method in accordance with an embodiment of the present invention for producing a water-absorbing resin composition includes adding at least one selected from a surfactant and a lubricant and a chelating agent to water-absorbing resin particles.

The surfactant and/or the lubricant is added to the water-absorbing resin particles in an amount (which is substantially the content in the water-absorbing resin composition) within a range of 0.0001 parts by mass to 0.1 parts by mass, preferably 0.0001 parts by mass to 0.05 parts by mass, more preferably 0.0003 parts by mass to 0.02 parts by mass, even more preferably 0.0004 parts by mass to 0.015 parts by mass, particularly preferably 0.0005 parts by mass to 0.01 parts by mass, most preferably 0.0005 parts by mass to 0.005 parts by mass, with respect to 100 parts by mass of the water-absorbing resin composition. In a case where the surfactant and/or the lubricant is added to the water-absorbing resin particles in an amount within the above range, even a water-absorbing resin composition having a high centrifuge retention capacity (CRC) has a sufficient urine resistance in a case where a chelating agent is also added to the water-absorbing resin particles. The amount of the surfactant and/or the lubricant added to the water-absorbing resin particles refers to the amount of the surfactant in a case where only a surfactant is added, the amount of the lubricant in a case where only a lubricant is added, or the combined amount of the surfactant and the lubricant in a case where both a surfactant and a lubricant are added.

The amount of the surfactant and/or the lubricant added is preferably not less than 0.0001 parts by mass because such an amount allows the urine resistance to be improved. On the other hand, as a comparison between Example 2 and Comparative Example 6 described later shows, the amount of the surfactant and/or the lubricant added is preferably not more than 0.1 parts by mass (preferably not more than 0.05 parts by mass) because such an amount alleviates the stickiness and re-wet increase in a case where, for example, the water-absorbing resin composition is used for a diaper.

An excessive amount of surfactant causes stickiness presumably for the following reason: An excessive amount of surfactant added excessively increases the fluidity of water-absorbing resin particles. The water-absorbing resin particles thus remains for a shorter retention time in a heating device (for example, a continuous paddle mixer for a surface-crosslinking operation) (the retention time is calculated by dividing the amount of fluidized water-absorbing resin particles by the capacity of the device).

This leaves the water-absorbing resin particles insufficiently heated, with the result of insufficient surface-crosslinking. Insufficiently surface-crosslinked water-absorbing resin particles have an increased post-degradation-test one-hour eluted soluble component, thereby causing stickiness.

An excessive amount of surfactant increases re-wet presumably for the following reason: An excessive amount of surfactant added leads to the surfactant in the water-absorbing resin composition to be eluted into a liquid to be absorbed. This decreases the surface tension of the liquid to be absorbed, thereby increasing re-wet.

The following description will discuss a surfactant and a lubricant to be added in a method in accordance with an embodiment of the present invention for producing a water-absorbing resin composition.

(2-1) Surfactant

The term "surfactant" as used in the present specification refers to molecules each having both a hydrophilic portion and a lipophilic (hydrophobic) portion and that is adsorbed on a surface of an object due to the balance between hydrophilicity and hydrophobicity to modify a surface property of that object. Example surfactants usable include anionic surfactants, nonionic surfactants, cationic surfactants, and amphoteric surfactants cited in Patent Literatures 1 and 3 to 5 as examples.

The surfactant for use in an embodiment of the present invention may have any HLB (hydrophile-lipophile balance; defined by the Griffin method). The HLB is, however, within a range of preferably 8 to 18, more preferably 9 to 17, even more preferably 10 to 17, particularly preferably 11 to 16, most preferably 12 to 16. With the HLB within the above range, even a water-absorbing resin composition having a high centrifuge retention capacity (CRC) has a sufficient urine resistance in a case where a chelating agent is also added to the water-absorbing resin particles.

Example anionic surfactants include fatty acid salts such as mixed fatty acid sodium soap, tack dry beef tallow fatty acid sodium soap, stearic acid sodium soap, oleic acid potassium soap, and castor oil potassium soap; alkyl sulfate ester salts such as sodium lauryl sulfate, higher alcohol sodium sulfate, sodium lauryl sulfate, and triethanolamine lauryl sulfate; alkyl benzene sulfonates such as sodium dodecylbenzenesulfonate; alkyl naphthalene sulfonates such as sodium alkylnaphthalenesulfonate; alkyl sulfosuccinate such as sodium dialkylsulfosuccinate; alkyl diphenyl ether disulfonates such as sodium alkyl diphenyl ether disulfonate; alkyl phosphates such as potassium alkyl phosphate; polyoxyethylene alkyl (or alkyl allyl) sulfates such as sodium polyoxyethylene lauryl ether sulfate, sodium polyoxyethylene alkyl ether sulfate, triethanolamine sulfate salt of polyoxyethylene alkyl ether, and sodium polyoxyethylene alkyl phenyl ether sulfate; a special reaction type anionic surfactant; a special carboxylic acid type surfactant: naphthalene sulfonic acid formalin condensates such as a sodium salt of β-naphthalenesulfonic acid formalin condensate and a sodium salt of special aromatic sulfonic acid formalin condensate; a special polycarboxylic acid type polymer surfactant; and polyoxyethylene alkyl phosphate ester.

Example nonionic surfactants include polyoxyethylene alkyl ethers such as polyoxyethylene lauryl ether, polyoxyethylene cetyl ether, polyoxyethylene stearyl ether, polyoxyethylene oleyl ether, and polyoxyethylene higher alcohol ether; polyoxyethylene alkylaryl ethers such as polyoxyethylene nonyl phenyl ether; polyoxyethylene derivatives; sorbitan fatty acid esters such as sorbitan monolaurate, sorbitan monopalmitate, sorbitan monostearate, sorbitan tristearate, sorbitan monooleate, sorbitan trioleate, sorbitan sesquioleate, and sorbitan distearate; polyoxyethylene sorbitan fatty acid esters such as polyoxyethylene sorbitan monolaurate, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, and polyoxyethylene sorbitan trioleate; polyoxyethylene sorbitol fatty acid ester such as polyoxyethylene sorbitol tetraoleate; glycerin fatty acid esters such as glycerol monostearate, glycerol monooleate, and self-emulsifying glycerol monostearate;

polyoxyethylene fatty acid esters such as polyethylene glycol monolaurate, polyethylene glycol monostearate, polyethylene glycol distearate, and polyethylene glycol monooleate; polyoxyethylene alkylamine; polyoxyethylene hydrogenated castor oil; and alkyl alkanol amide.

Examples of the cationic surfactants and the amphoteric surfactants include alkyl amine salts such as coconut amine acetate and stearylamine acetate; quaternary ammonium salts such as lauryl trimethyl ammonium chloride, stearyl trimethyl ammonium chlorite, cetyl trimethyl ammonium chloride, distearyl dimethyl ammonium chloride, and alkyl benzyl dimethyl ammonium chloride; alkyl betaines such as lauryl betaine, stearyl betaine, and lauryl carboxymethyl hydroxyethyl imidazolinium betaine; and amine oxides such as lauryl dimethyl amine oxide.

Another example surfactant is a fluorine-based surfactant. The fluorine-based surfactant usable in an embodiment of the present invention may vary. An example is prepared by replacing a hydrogen of a hydrophobic group of a common surfactant with a fluorine into a perfluoroalkyl group so that the substance has much higher surface activity.

For a fluorine-based surfactant, even in a case where a fluorocarbon chain of the same structure is used as a hydrophobic group, changing a hydrophilic group can change the fluorine-based surfactant into any of an anionic surfactant, a nonionic surfactant, a cationic surfactant, and an amphoteric surfactant. The carbon chain as a hydrophobic group may be a linear chain or be branched for use. Typical examples of fluorine-based surfactants include the following.

Fluoroalkyl (C2-C10) carboxylic acid, disodium N-perfluorooctanesulfonylglutamate, sodium 3-[fluoroalkyl (C6-C11) oxy]-1-alkyl (C3-C4) sulfonate, sodium 3-[co-fluoroalkanoyl (C6-C8)-N-ethylamino]-1-propanesulfonate, N-[3-(perfluorooctanesulfonamido) propyl]-N, N-dimethyl-N-carboxymethyleneammonium betaine, fluoroalkyl (C11-C20) carboxylic acid, perfluoroalkyl carboxylic acid (C7-C13), perfluorooctanesulfonic acid diethanolamide, perfluoroalkyl (C4-C12) sulfonate (Li, K, Na), N-propyl-N-(2-hydroxyethyl)perfluorooctanesulfonamide, perfluoroalkyl (C6-C10) alphonamidopropyl trimethyl ammonium salt, perfluoroalkyl (C6-C10)-N-ethylsulfonylglycine salt (K), bis(N-perfluorooctylsulfonyl-N-ethylaminoethyl) phosphate, monoperfluoroalkyl (C6-C16) ethyl phosphate, perfluoroalkyl quaternary ammonium iodide (trade name: Fluorad FC-135, cationic fluorine-based surfactant available from Sumitomo 3M Ltd.), perfluoroalkyl alkoxylate (trade name: Fluorad FC-171, nonionic surfactant available from Sumitomo 3M Ltd.), and a potassium salt of perfluoroalkylsulfonic acid (trade name: Fluorad FC-95 and FC-98, anionic surfactant available from Sumitomo 3M Ltd.). The number following each "C" refers to the number of carbon atoms. The expression "C2 to C10", for example, is intended to mean having 2 to 10 carbon atoms.

An embodiment of the present invention can use an organometallic surfactant as well. An embodiment of the present invention can use an organometallic surfactant as molecules each including a metal such as Si, Ti, Sn, Zr, and Ge in a main chain or side chain. The organometallic surfactant preferably is in the form of molecules each including Si in a main chain. The organometallic surfactant is more preferably a siloxane-based surfactant.

Representative examples of the organometallic surfactant include organometallic surfactants mentioned at page 34 of Yoshida, Kondo, Ogaki, and Yamanaka's "Shinban: Kaimenkasseizai handobukku" (New edition: Surfactant Handbook) published by Kogaku Tosho in 1966. The organometallic surfactant may include a metal of, for example, Sn, Zr, or Ge instead of Si or Ti. The surfactant for use in an embodiment of the present invention is not limited to any of the above surfactants.

The surfactant is, among the above surfactants, preferably a nonionic surfactant, more preferably fatty ester among other nonionic surfactants, particularly preferably sorbitan fatty acid ester or polyoxyethylene sorbitan fatty acid ester, in terms of safety.

Fatty acid ester for use as the surfactant has an acid value of preferably 0.001 mgKOH/g to 2.5 mgKOH/g, more preferably 0.001 mgKOH/g to 1.5 mgKOH/g, even more preferably 0.01 mgKOH/g to 1.0 mgKOH/g. An acid value of not more than 2.5 for the fatty acid ester is preferable because such an acid value can prevent an increase in the hydrophobicity of the surfactant. This prevents the surfactant from being left undissolved or deposited to clog a spray nozzle. The surfactant is thus easy to handle. The acid value of fatty acid ester cited in the present specification is a value as measured in conformity to a neutralization titration method defined in JIS K 0070 (1992).

(2-2) Lubricant

A lubricant is a substance that is present between two surfaces slidable on each other to decrease friction (resistance). In a case where two objects are in contact with each other, the slidability and resistance vary according to the state of the respective contact surfaces of the objects. A lubricant increases the slidability and decreases the resistance.

Examples of the lubricant for use in an embodiment of the present invention include lubricants cited in, for example, Patent Literature 1 as examples. Specific examples include a polymeric additive and other lubricants, which are described below.

(2-2a) Polymeric Additive (Composition of Polymeric Additive)

The polymeric additive usable for an embodiment of the present invention is a polymer compound obtained by (co)polymerizing monomers each having, in a side chain, a hydrocarbon group having not less than 7 carbon atoms or a polymer compound obtained by introducing, into a side chain of a polymer compound having a reactive group, a hydrocarbon group having not less than 7 carbon atoms.

The hydrocarbon group is made of carbon and hydrogen and has a hydrocarbon unit portion having not less than 7 carbon atoms. The hydrocarbon group may be a linear chain or branched chain, or may be cyclic. The hydrocarbon group may be saturated or unsaturated.

A monomer having the hydrocarbon group in a side chain is a monomer such that in a case where the monomer has been polymerized, a polymer compound has a hydrocarbon group suspended from a main chain. The present specification does not regard a branch caused during a polymerizing process as a side chain.

Specifically, the present specification does not construe, as a side chain, a branched chain of a polyolefin portion of, for example, an ethylene-acrylic acid copolymer, an ethylene-maleic anhydride copolymer, an ethylene-vinyl acetate copolymer, a propylene-acrylic acid copolymer, a propylene-maleic anhydride copolymer, or a propylene-vinyl acetate copolymer to each of which a method for synthesizing a high-pressure polyolefin (for example, polyethylene and polypropylene) is applied. These compounds are not economical because the polymer structure of each of such compounds cannot be controlled accurately, and the compound needs to be added in a large amount to improve the fluidity during moisture adsorption.

The side chain in which the hydrocarbon group is present has a length of preferably not less than 7 carbon atoms, more preferably not less than 8 carbon atoms, even more preferably not less than 10 carbon atoms, even more preferably not less than 12 carbon atoms, most preferably not less than 14. The length of the hydrocarbon group has no particular upper limit, but is preferably not more than 50, more preferably not more than 40, most preferably not more than 30.

The monomer for use in a polymeric additive for an embodiment of the present invention has, in a side chain, a hydrocarbon group having not less than 7 carbon atoms. The side chain may further contain, for example, a polyoxyethylene group and/or a polyoxypropylene group. Thus, the monomer having, in a side chain, a hydrocarbon group having not less than 7 carbon atoms may be water-soluble or water-insoluble.

The term "water-soluble monomer" (hydrophilic monomer) as used in the present specification refers to a monomer having a solubility of not less than 1 g, preferably not less than 5 g, more preferably not less than 10 g, most preferably not less than 20 g, with respect to 100 g of water having a temperature of 20° C.

The term "water-insoluble monomer" as used in the present specification refers to a monomer having a solubility of less than 1 g (with a lower limit of 0 g), preferably not more than 0.5 g, more preferably not more than 0.1 g, with respect to 100 g of water having a temperature of 20° C.

The monomer having, in a side chain, a hydrocarbon group having not less than 7 carbon atoms is, for example, an ester or amide monomer produced by causing an alcohol or amine having a linear-chain, branched-chain, or cyclic hydrocarbon group having not less than 7 carbon atoms to react with an ethylenic unsaturated monomer having a carboxyl group. Representative examples of such a monomer include (meth)acrylate esters and alkyl substituted (meth)acrylamides such as 2-ethyl-hexyl (meth)acrylate, lauryl (meth)acrylate, stearyl (meth)acrylate, isostearyl (meth)acrylate, palmityl (meth)acrylate, myristyl (meth)

acrylate, capryl (meth)acrylate, cetyl (meth)acrylate, isobornyl (meth)acrylate, undecylenyl (meth)acrylate, oleyl (meth) acrylate, 2-ethyl-hexyl (meth)acrylamide, lauryl (meth) acrylamide, stearyl (meth)acrylamide, isostearyl (meth) acrylamide, palmityl (meth)acrylamide, myristyl (meth) acrylamide, capryl (meth)acrylamide, cetyl (meth) acrylamide, isobornyl (meth)acrylamide, undecylenyl (meth)acrylamide, oleyl (meth)acrylamide. Examples of the monomer further include the esters and the amides of similar monomers such as maleic acid, fumaric acid, crotonic acid, and itaconic acid.

The monomer having, in a side chain, a hydrocarbon group having not less than 7 carbon atoms may be an ester monomer produced by causing a carboxylic acid having a linear-chain, branched-chain, or cyclic hydrocarbon group having not less than 7 carbon atoms to react with an ethylenic unsaturated monomer having a hydroxyl group. Representative examples of such a monomer include vinyl esters such as vinyl caprylate, vinyl caprate, vinyl laurate, vinyl myristate, vinyl palmitate, vinyl stearate, vinyl isostearate, vinyl undecylenate, vinyl behenate, vinyl naphthenate, vinyl linoleate, and vinyl linoleate. Examples of the monomer further include the esters of similar monomers such as hydroxyalkyl (meth)acrylate and polyethylene glycol (meth) acrylate. Examples of the similar monomers include undecylenoxy polyethylene glycol (meth)acrylate, which is particularly suitable.

The monomer having, in a side chain, a hydrocarbon group having not less than 7 carbon atoms may be an amide monomer produced by causing a carboxylic acid having a linear-chain, branched-chain, or cyclic hydrocarbon group having not less than 7 carbon atoms to react with an ethylenic unsaturated monomer having an amino group. Representative examples of such a monomer include vinylamides such as caprylic acid-N-vinylamide, capric acid-N-vinylamide, lauric acid-N-vinylamide, myristic acid-N-vinylamide, palmitic acid-N-vinylamide, stearic acid-N-vinylamide, isostearic acid-N-vinylamide, palmitic acid-N-vinylamide, undecylenic acid-N-vinylamide, behenic acid-N-vinylamide, naphthenic acid-N-vinylamide, linoleic acid-N-vinylamide, and linolenic acid-N-vinylamide.

The monomer having, in a side chain, a hydrocarbon group having not less than 7 carbon atoms may be a quarternary salt monomer, neutralized salt, or amine produced by causing a halide, alcohol, or carboxylic acid having a linear-chain, branched-chain, or cyclic hydrocarbon group having not less than 7 carbon atoms to react with an ethylenic unsaturated monomer having an amino group. Representative examples of such a monomer include quaternary salts, neutralizing salts, and amines of dialkylaminoalkyl (meth) acrylate, dialkylaminoalkyl (meth)acrylamide, vinylamine, allylamine, ethylene imine, or the like each having heptyl, octyl, 2-ethylhexyl, nonyl, lauryl, palmityl, stearyl, isostearyl, undecylenyl, behenyl, naphthyl, oleyl, cetyl, isobonyl group, or the like.

The monomer having, in a side chain, a hydrocarbon group having not less than 7 carbon atoms may be an ester monomer produced by causing an alcohol having a linear-chain, branched-chain, or cyclic hydrocarbon group having not less than 7 carbon atoms to react with an ethylenic unsaturated monomer having a sulfonate group or phosphate group. Representative examples of such a monomer include esters (such as heptyl esters, octyl esters, 2-ethylhexyl esters, nonyl esters, lauryl esters, palmityl esters, stearyl esters, isostearyl esters, undecylenyl esters, behenyl esters, naphthyl esters, oleyl esters, isobornyl esters, and cetyl esters) of vinyl sulfonic acid, styrene sulfonic acid, 2-(meth)acrylamide-2-methylpropanesulfonic acid, (meth)acryloxyalkane sulfonic acid, and the like.

The monomer having, in a side chain, a hydrocarbon group having not less than 7 carbon atoms may be α-olefin having, in a side chain, a linear-chain, branched-chain, or cyclic hydrocarbon group having not less than 7 carbon atoms. Representative examples of such a monomer include 1-nonene, 1-decene, and 1-octadecene.

It is possible to use only one of the above monomers or an appropriate mixture of two or more of the above monomers.

Similarly to the case of (co)polymerization, a polymer compound having, in a side chain, a hydrocarbon group having not less than 7 carbon atoms is construed as a polymeric additive, the polymer compound being obtained by causing a hydrocarbon group having not less than 7 carbon atoms to react later with a reactive group such as a carboxyl group, an amino group, a hydroxyl group, a sulfonate group, or a phosphate group.

In other words, a polymeric additive having, in a side chain, a hydrocarbon group having not less than 7 carbon atoms may be obtained by causing a polymer compound having a reactive group such as a carboxyl group, an amino group, a hydroxyl group, a sulfonate group, or a phosphate group to react with, for example, an alcohol, carboxylic acid, sulfonic acid, or amine having a hydrocarbon group having not less than 7 carbon atoms.

In a case where the polymeric additive has, in a side chain, a hydrocarbon group having not less than 7 carbon atoms, even a water-absorbing resin composition having a high centrifuge retention capacity (CRC) has a sufficient urine resistance in a case where the polymeric additive is added to the water-absorbing resin particles, and a chelating agent is also added to the water-absorbing resin particles.

In a case where the polymeric additive is obtained by copolymerization, the monomer having, in a side chain, a hydrocarbon group having not less than 7 carbon atoms is (co)polymerized in an amount within a range of preferably 15% by mass to 100% by mass, more preferably 20% by mass to 85% by mass, even more preferably 20% by mass to 70% by mass, with respect to the (co)polymer as a polymeric additive.

In a case where a polymeric additive is to be obtained by later introducing a hydrocarbon group having not less than 7 carbon atoms into a polymer compound having a reactive group, the hydrocarbon group having not less than 7 carbon atoms is contained in an amount within a range of preferably 15% by mass to 100% by mass, more preferably 20% by mass to 85% by mass, even more preferably 20% by mass to 70% by mass, with respect to the polymer as a polymeric additive in terms of the repeating unit (monomer unit). The expression "in terms of the repeating unit (monomer unit)" refers to the following: In a case where, for instance, stearyl alcohol has been caused to react with polyacrylic acid to obtain a polymeric additive having a stearyl group in a side chain, the polymeric additive is construed as a copolymer of acrylic acid and stearyl acrylate, and the above rate is calculated as the rate (mass) of the monomer (stearyl acrylate) having a stearyl group to the polymer as a polymeric additive.

In a case where the monomer having, in a side chain, a hydrocarbon group having not less than 7 carbon atoms is contained in an amount within the above range, even a water-absorbing resin composition having a high centrifuge retention capacity (CRC) has a sufficient urine resistance in a case where the polymeric additive is added to the water-absorbing resin particles, and a chelating agent is also added to the water-absorbing resin particles.

The polymeric additive has, in a side chain, a hydrocarbon group having not less than 7 carbon atoms. Any other monomer may be used in addition.

Specifically, such an additional monomer may be a monomer having, in a side chain, a hydrocarbon group having less than 7 carbon atoms or a water-soluble monomer. Examples of such a monomer include (meth)acrylic acid, maleic acid (anhydride), fumaric acid, crotonic acid, itaconic acid, vinyl sulfonic acid, 2-(meth)acrylamide-2-methylpropane sulfonic acid, (meth)acryloxyalkane sulfonic acid, esters thereof, amide, N-vinyl-2-pyrrolidone, N-vinylacetamide, (meth)acrylamide, N-isopropyl(meth)acrylamide, N,N-dimethyl (meth)acrylamide, 2-hydroxyethyl(meth) acrylate, methoxypolyethylene glycol(meth)acrylate, polyethylene glycol(meth)acrylate, and isobutylene. It is possible to use only one of the above monomers or an appropriate mixture of two or more of the above monomers.

To control the hydrophilicity and hydrophobicity of the surface of the water-absorbing resin composition, a polymeric additive in which the monomer having, in a side chain, a hydrocarbon group having not less than 7 carbon atoms and a water-soluble monomer have been (co)polymerized is preferably used. Such a water-soluble monomer is suitably (meth)acrylic acid, (meth)acrylamide, N-vinyl-2-pyrrolidone, 2-hydroxyethyl (meth)acrylate, methoxypolyethyleneglycol (meth)acrylate, or polyethyleneglycol (meth)acrylate.

The polymeric additive is preferably a polymeric additive in which both a hydrophobic, water-insoluble monomer and a hydrophilic, water-soluble monomer have been copolymerized. The mass ratio of the water-soluble monomer to the water-insoluble monomer is within a range of preferably 15:85 to 85:15, more preferably 20:80 to 80:20, even more preferably 20:80 to 70:30, most preferably 20:80 to 60:40.

In a case where a polymeric additive containing, in a polymer chain, a water-soluble monomer and a water-insoluble monomer that have been copolymerized is added to the water-absorbing resin particles, even a water-absorbing resin composition having a high centrifuge retention capacity (CRC) has a sufficient urine resistance in a case where the polymeric additive is added to the water-absorbing resin particles, and a chelating agent is also added to the water-absorbing resin particles.

In a case where the hydrophilic monomer of the polymeric additive to be added to the water-absorbing resin particles is a monomer having a carboxyl group, a monomer having a sulfonate group, a monomer having a phosphate group, or a monomer having an amino group, the polymeric additive may be in the form of a neutralized salt (for example, an alkali metal salt, an alkaline earth metal salt, a transition metal salt, an ammonium salt, a halide salt, an organic salt, a phosphate, or a sulfonate). The polymeric additive is preferably a metal salt having a valence of 1 or more. Examples include sodium, potassium, iron, magnesium, silver, zinc, copper, and tin. The neutralization degree is preferably not more than 75 mol % (with a lower limit of 0 mol %), more preferably not more than 50 mol %, even more preferably not more than 25 mol %, most preferably not more than 10 mol %, with respect to the number of moles of all the carboxyl groups, sulfonate groups, and amino groups in the polymeric additive.

In a case where the polymeric additive is to be added to the water-absorbing resin particles in the form of powder or suspension, it is possible to, in addition to the above monomer, copolymerize or react a crosslinking monomer (referred to also as a crosslinking agent) including molecules in each of which two or more polymerizable unsaturated groups or two or more reactive groups are present. Specific examples of the crosslinking agent include N,N'-methylenebis(meth)acrylamide, (poly)ethylene glycol di(meth)acrylate, (poly)propylene glycol di(meth)acrylate, trimethylolpropane tri(meth)acrylate, glycerin tri(meth)acrylate, glycerin acrylate methacrylate, ethyleneoxide modified trimethylol propane tri(meth)acrylate, pentaerythritol hexa (meth)acrylate, triallyl cyanurate, triallyl isocyanurate, triallyl phosphate, triallylamine, poly(meth)allyloxy alkane, (poly)ethylene glycol diglycidyl ether, glycerol diglycidyl ether, ethylene glycol, polyethylene glycol, propylene glycol, glycerin, pentaerythritol, ethylenediamine, ethylene carbonate, propylene carbonate, polyethyleneimine, and glycidyl (meth)acrylate.

It is possible to use only one of the above crosslinking agents or an appropriate mixture of two or more of the above crosslinking agents. Further, it is possible to add the total amount of the crosslinking agent to the reaction system at one time or add the crosslinking agent to the reaction system in separate portions.

Determining whether to add such a crosslinking agent and how much of the crosslinking agent to add can adjust the solubility of the polymeric additive with respect to neutral water so that the polymeric additive is either soluble or insoluble. The crosslinking agent is used in an amount within a range of preferably 0.001 mol % to 10 mol %, more preferably 0.005 mol % to 5 mol %, even more preferably 0.01 mol % to 1 mol %, with respect to the monomer (except the internal crosslinking agent).

The polymeric additive has a melting point, a glass transition point, or a softening point within a range of preferably 40° C. to 250° C., more preferably 50° C. to 200° C., even more preferably 60° C. to 150° C. In a case where the polymeric additive has a melting point, a glass transition point, or a softening point of not lower than 40° C., even a water-absorbing resin composition having a high centrifuge retention capacity (CRC) preferably has a sufficient urine resistance in a case where the polymeric additive is added to the water-absorbing resin particles, and a chelating agent is also added to the water-absorbing resin particles. Further, the polymeric additive preferably has a melting point, a glass transition point, or a softening point of not higher than 250° C. because in that case, neither a base material nor the water-absorbing resin composition is thermally degraded.

The polymeric additive has a molecular weight (mass average molecular weight) within a range of normally 1,000 to 1,000,000, preferably 5,000 to 1,000,000, more preferably 10,000 to 1,000,000, most preferably 50,000 to 1,000,000. In a case where the polymeric additive has a molecular weight within the above range, even a water-absorbing resin composition having a high centrifuge retention capacity (CRC) preferably has a sufficient urine resistance in a case where the polymeric additive is added to the water-absorbing resin particles, and a chelating agent is also added to the water-absorbing resin particles.

When the polymeric additive is added to the water-absorbing resin particles, the polymeric additive may be in the form of a solution, a suspension, or powder.

In a case where the polymeric additive is to be added to the water-absorbing resin particles in the form of powder (fine particles), the polymeric additive powder may have any particle diameter or particle shape. The polymeric additive powder normally has a mass average particle diameter smaller than that of the water-absorbing resin particles. Preferably, not less than 90% by mass (with an upper limit of 100% by mass) of the total amount of the polymeric additive powder is within a range of 0.01 μm to 100 μm. In particular, not less than 90% by mass of the total amount of the polymeric additive powder is within a range of more preferably 0.01 μm to 75 μm, even more preferably 5 μm to 75 μm, most preferably 5 μm to 50 μm.

The polymeric additive powder has an average particle diameter (D50) within a range of preferably 0.01 μm to 100 μm, more preferably 0.01 μm to 75 μm, most preferably 0.01 μm to 50 μm. The particle diameter distribution and the average particle diameter can each be measured easily by a conventional measurement method such as Coulter counter method or laser diffraction scattering method. The form of particles may be a granulated product of fine particles or primary particles (single particles).

In a case where the polymeric additive powder (fine particles) has particle diameters within the above range, even a water-absorbing resin composition having a high centrifuge retention capacity (CRC) preferably has a sufficient urine resistance in a case where the polymeric additive is added to the water-absorbing resin particles, and a chelating agent is also added to the water-absorbing resin particles.

(2-2b) Other Lubricants

A lubricant(s) usable for an embodiment of the present invention other than the polymeric additive is not limited to any particular one as long as the lubricant is a solid lubricant. Examples of the other lubricant include a hydrocarbon-based lubricant, a fatty acid-based lubricant, a fatty acid amide-based lubricant, an ester-based lubricant, an alcohol-based lubricant, and a metal soap lubricant. Among others, a metal soap lubricant is preferable because it acts not only as a lubricant but also as a stabilization agent.

Examples of the hydrocarbon-based lubricant include a low polymerization polyethylene. A low polymerization polyethylene is a polyethylene having a molecular weight within a range of approximately 1500 to 2000.

The fatty acid-based lubricant is not limited to any particular one as long as the fatty acid acts as a lubricant. The fatty acid-based lubricant is preferably a fatty acid having not less than 12 (C12) carbon atoms. Specific examples of the fatty acid-based lubricant include lauric acid, myristic acid, palmitic acid, stearic acid, arachidic acid, and behenic acid. Among others, stearic acid is preferable because it is easily available. The fatty acid-based lubricant is preferably in the form of fine particles. The fatty acid-based lubricant is desirably a fatty acid-based lubricant that contains no heavy metal such as Fe and Ni, which accelerates degradation of the water-absorbing resin particles, and that is a refined product having a low iodine value and a low ester value.

The fatty acid amide-based lubricant is a compound derived from fatty acid and expressed by the general chemical formula $RCONH_2$. The fatty acid amide can be a primary amide (R—$CONH_2$), a secondary amide (($RCO)_2NH$), or a tertiary amide (($RCO)_3N$). The fatty acid amide is preferably a primary amide. Specific examples of the fatty acid amide-based lubricant include stearylamide, palmitylamide, oleylamide, methylene-bis-stearamide, and ethylene-bis-stearamide. Among others, methylene-bis-stearamide and ethylene-bis-stearamide are preferable because they are excellent in compatibility, transparency, weather resistance, and nonadherence.

Examples of the ester-based lubricant include a polyhydric alcohol ester of fatty acid and a polyglycol ester of fatty acid. The polyhydric alcohol ester of fatty acid is preferably hydrogenated castor oil. The polyglycol ester of fatty acid is preferably ethyleneglycol monostearate.

The alcohol-based lubricant is produced by replacing hydrogen of a hydrocarbon-based lubricant or fatty acid-based lubricant with a hydroxyl group. The alcohol-based lubricant is not limited to any particular one as long as the alcohol-based lubricant is produced by replacing hydrogen of a hydrocarbon-based lubricant or fatty acid-based lubricant with a hydroxyl group. Examples of the alcohol-based lubricant include a fatty alcohol having a single hydroxyl group in each molecule such as cetyl alcohol and stearyl alcohol; a glycol having two hydroxyl groups in each molecule such as polyethylene glycol; and polyglycerol having three hydroxyl groups in each molecule. Polyethylene glycol and polyglycerol each not only act as a lubricant but also produce an antistatic effect.

The metal soap lubricant is made of a metal salt (other than an alkali metal salt) of fatty acid, petroleum acid, polymer acid, or the like as an organic acid.

The lubricant is normally in the form of powder and may have any particle diameter. The lubricant normally has a mass average particle diameter smaller than that of the water-absorbing resin particles. Not less than 90% by mass of the powder is not more than 100 μm, preferably not more than 50 μm, more preferably not more than 10 μm.

It is possible to use only one of the above lubricants or a combination of two or more of the above lubricants.

The lubricant can be added to the water-absorbing resin particles by a method similar to a method by which the polymeric additive is added to the water-absorbing resin particles.

In a case where the lubricant is to be dispersed into the form of slurry to be mixed with the water-absorbing resin particles, the slurry has a lubricant concentration that is selected as appropriate depending on the lubricant used, the kind of the dispersion solvent, and the viscosity of the slurry and that is not limited to any particular value. The lubricant concentration is, however, within a range of normally 0.0001% by mass to 0.1% by mass, preferably 0.001% by mass to 0.05% by mass.

In a case where the water-absorbing resin particles with which the lubricant is to be mixed is in the form of powder, the water-absorbing resin particles have a powder temperature of normally not lower than room temperature when mixed with the lubricant. The powder temperature is, however, preferably not lower than 40° C., more preferably not lower than 50° C., to produce a water-absorbing resin composition having a stable water absorbent property, flow rate, and bulk density.

(2-3) Adding Surfactant and/or Lubricant

A method in accordance with an embodiment of the present invention for producing a water-absorbing resin composition includes adding a surfactant and/or a lubricant at any stage during the production of a water-absorbing resin. As described later, the production of the water-absorbing resin composition includes steps such as a polymerization step, a gel-crushing step, a drying step, a pulverizing step, a classification step, a surface-crosslinking step, and an additive adding step. The surfactant and/or the lubricant may be added in any of the above steps.

The following description will discuss specific examples of the stage at which the surfactant and/or the lubricant is added and a method for adding the surfactant and/or the lubricant. The classification step described herein refers to a classification step carried out before a surface-crosslinking step. The classification step is more preferably a step of, before a surface-crosslinking step, classifying water-absorbing resin particles that have been polymerized, dried, and pulverized.

1. A method of, at any stage during the period after the end of the step of polymerizing a water-absorbing resin and before the start of the classification step (for example, at the end of the polymerization step during which a particulate crosslinked hydrogel polymer is obtained, during the gel-crushing step, after the end of the gel-crushing step and before the start of the drying step, during the drying step, after the end of the drying step and before the start of the pulverizing step, during the pulverizing step, or after the end of the pulverizing step and before the start of the classification step), adding a surfactant and/or a lubricant to the water-absorbing resin particles at the stage and as necessary gel-crushing, drying, pulverizing, classifying, surface-crosslinking, and/or adding an additive to the water-absorbing resin particles to obtain a water-absorbing resin composition.

2. A method of, at any stage after the end of the classification step and until the end of the surface-crosslinking step (for example, after the end of the classification step and before the surface-crosslinking step or during the surface-crosslinking step), adding a surfactant and/or a lubricant to the water-absorbing resin particles that have not been surface-crosslinked and as necessary surface-crosslinking and/or adding an additive to the water-absorbing resin particles to obtain a water-absorbing resin composition. The surfactant and/or the lubricant may be added at the same time as the addition of a surface crosslinking agent solution containing a surface-crosslinking agent, separately from or as mixed with the surface crosslinking agent solution, before the addition of the surface-crosslinking agent solution, after the addition of the surface-crosslinking agent solution and before the heating, or after the addition of the surface-crosslinking agent solution, during the heating, and after the heating.

3. A method of, at any stage after the surface-crosslinking (for example, after the surface-crosslinking and before the additive adding step, during the additive adding step, or after the additive adding step), adding a surfactant and/or a lubricant to the water-absorbing resin particles and as necessary adding an additive to the water-absorbing resin particles to obtain a water-absorbing resin composition.

4. A method of adding a surfactant and/or a lubricant to the water-absorbing resin particles, heating the water-absorbing resin particles while stirring the water-absorbing resin particles to melt the surfactant and/or the lubricant, and then cooling the water-absorbing resin particles to produce a water-absorbing resin composition.

Among the above steps, the surfactant and/or the lubricant is added preferably during the period extending from the time at which at least a portion of the crosslinked hydrogel polymer becomes particulate during the polymerization step or gel-crushing step to the end of the surface-crosslinking step, more preferably during the period extending from the end of the pulverizing step to the end of the surface-crosslinking step, particularly preferably during the period extending from the end of the classification step to the end of the surface-crosslinking step. In other words, the method 2 above is the most preferable among the above examples. In a case where a surfactant and/or a lubricant is added during any of the above stages, even a water-absorbing resin composition having a high centrifuge retention capacity (CRC) has a sufficient urine resistance in a case where a chelating agent is also added to the water-absorbing resin particles.

The surfactant and/or the lubricant may be added at the same time as or at a time point different from the addition of a chelating agent described later. The addition of the surfactant and/or the lubricant and the addition of a chelating agent described later may be based on a combination of when to add the surfactant and/or the lubricant described above and when to add a chelating agent described later. In particular, the surfactant and/or the lubricant is added preferably before the addition of the chelating agent. Such an order of addition allows even a water-absorbing resin composition having a high centrifuge retention capacity (CRC) to have a sufficient urine resistance.

The combination of when to add the surfactant and/or the lubricant and when to add the chelating agent is as follows: (i) Preferably, the surfactant and/or the lubricant is added during the period extending from the time at which at least a portion of the crosslinked hydrogel polymer becomes particulate during the polymerization step or gel-crushing step to the end of the surface-crosslinking step, and the chelating agent is added thereafter during the period extending from the end of the polymerization step to the end of the additive adding step. (ii) More preferably, the surfactant and/or the lubricant is added during the period extending from the end of the classification step to the end of the surface-crosslinking step, and the chelating agent is added thereafter. (iii) Even more preferably, the surfactant and/or the lubricant is added during the period extending from the end of the classification step to the end of the surface-crosslinking step, and the chelating agent is added thereafter after the end of the surface-crosslinking step. As a preferable embodiment of (iii) above, the surfactant and/or the lubricant is added during the surface-crosslinking step in the form of a surface-treating liquid containing a surface-crosslinking agent and the surfactant and/or the lubricant, and the chelating agent is added thereafter during the additive adding step together with water and as necessary an additive(s). This also allows even a water-absorbing resin composition having a high centrifuge retention capacity (CRC) to have a sufficient urine resistance.

[3] Chelating Agent

Examples of the chelating agent for use in an embodiment of the present invention include aminocarboxylic acid and salts thereof, polycarboxylic acid and derivatives thereof, (poly)phosphoric acid and derivatives thereof, N-acylated glutamic acid and N-acylated aspartic acid and salts thereof, β-diketone derivatives, tropolone derivatives, and organic phosphoric acid compounds.

Examples of the aminocarboxylic acid and salts thereof include dihydroxyethylglycine, iminodiacetic acid, hydroxyethyl iminodiacetic acid, dihydroxyethylglycine, nitrilotriacetic acid, ethylenediamine tetraacetic acid, diethylenetriamine pentaacetic acid, triethylene tetramine hexaacetic acid, cyclohexane-1,2-diamine tetraacetic acid, N-hydroxyethylethylenediaminetriacetic acid, ethylene glycol diethyl ether diamine tetraacetic acid, ethylenediamine tetrapropionic acid, N-alkyl-N'-carboxymethyl aspartic acid, N-alkenyl-N'-carboxymethyl aspartic acid, and alkali metal salts thereof, alkaline earth metal salts thereof, and ammonium salts or amine salts thereof. Among others, an aminocarboxylic acid having three or more carboxyl groups and salts thereof are preferable in terms of chelating ability.

Examples of the polycarboxylic acid and derivatives thereof include succinic acid, polyacrylic acid, citric acid monoalkylamide, citric acid monoalkenylamide, malonic acid monoalkylamide, malonic monoalkenyl amide, and alkali metal salts thereof, alkaline earth metal salts thereof, and ammonium salts or amine salts thereof.

Examples of the (poly)phosphoric acid and derivatives thereof include hexametaphosphoric acid, metaphosphoric acid, tripolyphosphoric acid, phosphate alkyl ester, phosphoric acid alkenyl ester, and alkali metal salts thereof, alkaline earth metal salts thereof, and ammonium salts or amine salts thereof.

Examples of the N-acylated glutamic acid and N-acylated aspartic acid and salts thereof include Amisoft HS-11 and Amisoft GS-11, which are commercially available from Ajinomoto Co., Inc.

Examples of the β-diketone derivatives include acetylacetone and benzoylacetone.

Examples of the tropolone derivatives include tropolone, β-thujapricin, and γ-thujapricin.

Examples of the organic phosphoric acid compounds include ethylidene phosphonic acid, 1-hydroxyethylidene-1,1-diphosphonic acid, aminotrimethylene phosphonic acid, ethylenediamine tetra(methylene phosphonic acid), and diethylenetriamine penta(methylene phosphonic acid). Particularly preferable examples include 1-hydroxyethylidene-1,1-diphosphonic acid, ethylenediaminetetra(methylene phosphonic acid), and diethylenetriaminepenta(methylene phosphonic acid). Preferable examples of the salts include alkali metal salts such as a Na salt and K salt, ammonium salts, and amine salts. These compounds are each known as a kind of sequestering agent.

Among the above chelating agents, an aminocarboxylic acid having three or more carboxyl groups and salts thereof are preferable. Among others, diethylenetriaminepentaacetic acid, triethylenetetraaminehexaacetic acid, cyclohexane-1,2-diaminotetraacetic acid, N-hydroxyethylethylenediaminetriacetic acid, and salts thereof are the most preferable in terms of urine resistance.

For an embodiment of the present invention, the chelating agent is used in an amount within a range of 0.0001 parts by mass to 1.0 part by mass, preferably 0.0005 parts by mass to 0.1 parts by mass, more preferably 0.001 parts by mass to 0.05 parts by mass, even more preferably 0.005 parts by mass to 0.03 parts by mass, particularly preferably 0.008 parts by mass to 0.03 parts by mass, most preferably 0.01 parts by mass to 0.03 parts by mass, with respect to 100 parts by mass of the water-absorbing resin composition. In a case where the amount of the chelating agent is not more than 1.0 part by mass, the combined use of the chelating agent and the surfactant and/or the lubricant allows for a sufficient urine resistance, is economical, and allows for a sufficient absorption amount. In a case where the amount of the chelating agent is not less than 0.0001 parts by mass, the urine resistance is improved.

The chelating agent can be added at any stage as long as the water-absorbing resin is in particulate form. Specifically, during the process described later of producing a water-absorbing resin composition, the chelating agent can be added at any stage after the time at which at least a portion of the crosslinked hydrogel polymer becomes particulate during the polymerization step or gel-crushing step. The chelating agent is preferably added during the period extending from the end of the polymerization step to the end of the additive adding step. In a case where the chelating agent is added at such a stage, even a water-absorbing resin composition having a high centrifuge retention capacity (CRC) (for example, not less than 35 g/g) has a sufficient urine resistance in a case where the surfactant and/or the lubricant is also added to the water-absorbing resin particles.

Among the stages that satisfy the above condition, the chelating agent is added preferably during the period extending from the end of the classification step to the end of the additive adding step, more preferably during the surface-crosslinking step or after the end of the surface-crosslinking step, particularly preferably during the period extending from the end of the surface-crosslinking to the end of the additive adding step, most preferably during the additive adding step. This allows the chelating agent to be present locally at and near the surfaces of the water-absorbing resin particles, and thereby allows for a sufficient urine resistance. Adding the chelating agent during the additive adding step can economically reduce the number of steps necessary for the production. The classification step described herein refers to a classification step carried out before a surface-crosslinking step. The classification step is more preferably a step of, before a surface-crosslinking step, classifying water-absorbing resin particles that have been polymerized, dried, and pulverized.

In a case where the chelating agent is to be added during the additive adding step, the chelating agent can be added by, for example, spraying water and the chelating agent onto the water-absorbing resin particles that have been surface-crosslinked with use of a surface-crosslinking agent. This makes it possible to obtain a water-absorbing resin composition having an excellent urine resistance. In this case, the amount of water to be added is within a range of 0.1 parts by mass to 20 parts by mass, preferably 0.1 parts by mass to 10 parts by mass, more preferably 0.2 parts by mass to 5 parts by mass, particularly preferably 0.3 parts by mass to 3 parts by mass, with respect to 100 parts by mass of the water-absorbing resin particles. If the amount of water added is less than 0.1 parts by mass, the chelating agent will undesirably be distributed non-uniformly on the surfaces of the water-absorbing resin particles. If the amount of water added is more than 20 parts by mass, the chelating agent will permeate through the water-absorbing resin particles, undesirably making it impossible to obtain a water-absorbing resin composition intended for the present invention and additionally breaking the surface-crosslinked layer at the surfaces of the water-absorbing resin particles.

A hydrophilic organic solvent such as methanol, ethanol, and isopropyl alcohol can additionally be used for the chelating agent and water to be mixed better with the water-absorbing resin particles. Further, an additive(s) of inorganic fine particles of silica, titanium oxide, or the like can also be added before or at the same time as the addition of the chelating agent.

The chelating agent may be added by any method. Example methods other than the above method include a method of adding the chelating agent to the water-absorbing resin particles and then adding water and as necessary an additive(s) for granulation.

Adding the chelating agent after surface-crosslinking the water-absorbing resin particles allows the chelating agent to be present locally at and near the surfaces of the water-absorbing resin particles. Since degradation of water-absorbing resin particles starts at the surfaces of the particles, it is useful to cause the chelating agent to be present at and near the surfaces of the water-absorbing resin particles.

If the chelating agent is added when a water-soluble monomer that can be contained in water-absorbing resin particles is polymerized, the monomer will be polymerized in the presence of the chelating agent. This slows the polymerization of the monomer, and may thereby make it impossible to obtain water-absorbing resin particles having an excellent absorbing performance. Further, the chelating agent may lose its chelating ability during the polymerization. In addition, if the chelating agent is added during the polymerization, the chelating agent will be present inside the particles. This may result in a decreased effect of urine resistance improvement as compared to a case where the chelating agent is added in the same amount after the particles are formed.

[4] Method for Producing Water-Absorbing Resin Composition

A method in accordance with an embodiment of the present invention for producing a water-absorbing resin composition having a centrifuge retention capacity (CRC) of not less than 35 g/g preferably includes adding a surfactant and/or a lubricant and a chelating agent to water-absorbing resin particles.

The water-absorbing resin particles are preferably such that water-absorbing resin particles (base polymer) that are obtained by as necessary gel-crushing, drying, as necessary pulverizing and classifying a crosslinked hydrogel polymer obtained through the polymerization step and that have not been surface-crosslinked have a centrifuge retention capacity (CRC) of preferably not less than 35 g/g, more preferably not less than 40 g/g, even more preferably not less than 45 g/g, particularly preferably not less than 48 g/g (although the water-absorbing resin particles are not limited as such). The CRC normally has an upper limit of preferably not more than 70 g/g, more preferably not more than 60 g/g, for balance with other properties (in particular, urine resistance).

The surface-crosslinking step described later may cause the centrifuge retention capacity (CRC) to decrease. In that case, adjustment is made so that water-absorbing resin particles (base polymer) that have not been surface-crosslinked have a high centrifuge retention capacity (CRC). In a case where, for instance, surface-crosslinking causes the centrifuge retention capacity (CRC) to decrease by 10 g/g, the amount of the internal crosslinking agent is adjusted so that water-absorbing resin particles that have not been surface-crosslinked have a centrifuge retention capacity (CRC) of not less than 45 g/g. This allows surface-crosslinked water-absorbing resin particles to have a centrifuge retention capacity (CRC) adjusted to not less than 35 g/g.

A method for producing water-absorbing resin particles for use in a method in accordance with an embodiment of the present invention for producing a water-absorbing resin composition may include a polymerization step, a gel-crushing step, a drying step, a pulverizing step, a classification step, a surface-crosslinking step, an additive adding step, and as necessary a fine powder removal step each described later.

The water-absorbing resin particles are obtained by crosslinking the vicinity of the surfaces of water-absorbing resin particles obtained by polymerizing a monomer component containing unsaturated carboxylic acid in the presence of an internal crosslinking agent. The use of an internal crosslinking agent can prevent a soluble component from being eluted from inside a swollen gel in a case where the gel has been exposed to a degrading atmosphere. Granulation allows the water-absorbing resin particles to have a larger average particle diameter, and improves the fluidity during moisture absorption, making the water-absorbing resin particles easier to handle.

(4-1) Polymerization Step

This step is a step of polymerizing an aqueous solution containing an unsaturated monomer to obtain a crosslinked hydrogel polymer (hereinafter referred to as "hydrogel").

(Unsaturated Monomer (Except for Crosslinking Agent))

Examples of the water-absorbing resin include a polyacrylic acid (salt)-based crosslinked polymer, a hydrolyzed starch-acrylonitrile graft polymer, a starch-acrylic acid graft polymer, a saponified vinyl acetate-acrylic ester copolymer, a hydrolyzed acrylonitrile copolymer or hydrolyzed acrylamide copolymer, a crosslinked acrylonitrile copolymer or crosslinked acrylamide copolymer, a denatured crosslinked polyvinyl alcohol containing a carboxyl group, and a crosslinked isobutylene-maleic anhydride copolymer. It is possible to use only one of these polymers or a combination of two or more of the polymers. Thus, a monomer that allows for desired properties is selected as the unsaturated monomer for obtaining a water-absorbing resin. The water-absorbing resin is particularly preferably a polyacrylic acid (salt)-based crosslinked polymer (which is synonymous with "polyacrylic acid (salt)-based water-absorbing resin") in terms of the properties of a water-absorbing resin to be obtained.

In a case where a polyacrylic acid (salt)-based crosslinked polymer is used, the unsaturated monomer is an acrylic acid (salt) as a main component. A monomer (hereinafter referred to as "other monomer(s)") other than an acrylic acid (salt) may be used as a copolymerization component. This makes it possible to impart, to a water-absorbing resin composition as a final product, a property other than water absorption such as an antibacterial property and a deodorizing property and produce a water-absorbing resin composition more inexpensively. Such a polyacrylic acid (salt)-based water-absorbing resin may optionally contain a graft component (for example, starch or polyvinyl alcohol) in an amount within a range of preferably not less than 0% by mass and not more than 50% by mass, more preferably not less than 0% by mass and not more than 40% by mass. Such a graft polymer is also referred to herein as "polyacrylic acid (salt)-based water-absorbing resin".

The other monomer(s) is not limited to any particular one. Examples of the other monomer(s) include water-soluble or hydrophobic unsaturated monomers such as methacrylic acid, maleic acid (anhydride), fumaric acid, crotonic acid, itaconic acid, vinyl sulfonic acid, 2-(meth)acrylamide-2-methylpropanesulfonic acid, (meth)acryloxyalkanesulfonic acid and alkali metal salts or ammonium salts thereof, N-vinyl-2-pyrrolidone, N-(meth)acrylamide, N,N-dimethyl (meth)acrylamide, 2-hydroxyethyl (meth)acrylate, methoxy polyethylene glycol (meth)acrylate, polyethylene glycol (meth)acrylate, isobutylene, and lauryl (meth)acrylate.

The other monomer(s) described above is used in an amount within a range of 0 mol % to 50 mol %, preferably 0 mol % to 30 mol %, more preferably 0 mol % to 10 mol %, even more preferably 0 mol % to 5 mol %, with respect to the total number of moles of the unsaturated monomer as a whole. Stated differently, the acrylic acid (salt) as a main component is used in an amount within a range of preferably 70 mol % to 100 mol %, more preferably 90 mol % to 100 mol %, even more preferably 95 mol % to 100 mol %. However, the acrylic acid (salt) as a main component is most preferably used in an amount of substantially 100 mol % in terms of the water absorption performance (such as AAP) of a water-absorbing resin composition to be obtained.

In a case where the unsaturated monomer (including the other monomer(s) described above) is a monomer having an acid group, a salt of the unsaturated monomer is an alkali metal salt, an alkaline earth metal salt, or an ammonium salt. Among others, a monovalent salt, in particular a monovalent metal salt, more particularly a sodium salt or a potassium salt, is preferably used in terms of, for example, the performance of a water-absorbing resin composition to be obtained and industrial availability and safety of the unsaturated monomer salt.

In a case where the unsaturated monomer is an acrylic acid (salt), (i) preferably, an acrylic acid is contained in an amount within a range of 0 mol % to 50 mol %, and an acrylic acid salt is contained in an amount within a range of 50 mol % to 100 mol % (as long as the total of the two is not more than 100 mol %; this applies hereafter in this paragraph), (ii) more preferably, an acrylic acid is contained in an amount within a range of 10 mol % to 40 mol %, and an acrylic acid salt is contained in an amount within a range of 60 mol % to 90 mol %, and (iii) even more preferably, an acrylic acid is contained in an amount within a range of 20 mol % to 30 mol %, and an acrylic acid salt is contained in an amount within a range of 70 mol % to 80 mol %, with respect to the combined number of moles of the acrylic acid and the acrylic acid salt. In other words, the neutralization rate (which is a molar ratio of the acrylic acid salt to the combined amount of the acrylic acid and the acrylic acid salt) is within a range of preferably 50 mol % to 100 mol %, more preferably 60 mol % to 90 mol %, even more preferably 70 mol % to 80 mol %.

An acrylic acid salt can be prepared by neutralizing an acrylic acid as a monomer before polymerization, neutralizing an acrylic acid while the acrylic acid is being polymerized or as a polymer after polymerization, or a combination of these operations. Alternatively, an acrylic acid and an acrylic acid salt may be mixed with each other to prepare an acrylic acid (salt).

(Internal Crosslinking Agent)

A water-absorbing resin in accordance with an embodiment of the present invention may be regarded as having an internal crosslinked structure if the water-absorbing resin is water-swellable and water-insoluble. This means that the internal crosslinked structure may be achieved through self-crosslinking of the unsaturated monomer, without use of an internal crosslinking agent. The internal crosslinked structure is, however, preferably achieved through copolymerization or reaction of the unsaturated monomer and an internal crosslinking agent. The internal crosslinking agent is, for example, an internal crosslinking agent having two or more polymerizable unsaturated groups and two or more reactive groups in each molecule.

Specific examples of the internal crosslinking agent include N,N'-methylenebis(meth)acrylamide, (poly)ethylene glycol di(meth)acrylate, (poly)propylene glycol di(meth)acrylate, trimethylolpropane tri(meth)acrylate, glycerin tri(meth)acrylate, glycerin acrylate methacrylate, ethyleneoxide modified trimethylol propane tri(meth)acrylate, pentaerythritol hexa(meth)acrylate, triallyl cyanurate, triallyl isocyanurate, triallyl phosphate, triallylamine, poly(meth)allyloxy alkane, (poly)ethylene glycol diglycidyl ether, glycerol diglycidyl ether, ethylene glycol, polyethylene glycol, propylene glycol, glycerin, pentaerythritol, ethylenediamine, ethylene carbonate, propylene carbonate, polyethyleneimine, and glycidyl (meth)acrylate.

It is possible to use only one of the above internal crosslinking agents or an appropriate mixture of two or more of the above internal crosslinking agents. Further, it is possible to add the total amount of the internal crosslinking agent to the reaction system at one time or add the internal crosslinking agent to the reaction system in separate portions. In view of the water absorption performance of a water-absorbing resin composition as a final product, it is preferable to use an internal crosslinking agent having two or more polymerizable unsaturated groups for polymerization.

The internal crosslinking agent is used in an amount within a range of preferably 0.0005 mol % to 0.5 mol %, more preferably 0.001 mol % to 0.3 mol %, even more preferably 0.005 mol % to 0.2 mol %, particularly preferably 0.007 mol % to 0.1 mol %, most preferably 0.005 mol % to 0.05 mol %, with respect to the monomers except for the crosslinking agent in order to produce a water-absorbing resin having good properties. A smaller amount of use of the internal crosslinking agent tends to result in an increase in the centrifuge retention capacity (CRC). The amount within a range of 0.0005 mol % to 0.5 mol % is preferable because such an amount allows water-absorbing resin particles and a water-absorbing resin composition to have a centrifuge retention capacity (CRC) of not less than 35 g/g as a water absorption performance.

In a case where the internal crosslinking agent is used to introduce an internal crosslinked structure into the water-absorbing resin, the internal crosslinking agent is added to the reaction system before or during the polymerization of the unsaturated monomer, after the polymerization, or after the neutralization.

(Polymerization initiator) A polymerization initiator for use during the polymerization step is selected as appropriate depending on how the polymerization is carried out, and is not limited to any particular one. Examples of the polymerization initiator include photolytic-type polymerization initiators, pyrolysis-type polymerization initiators, and redox-type polymerization initiators.

Examples of the photolytic-type polymerization initiators include benzoin derivatives, benzyl derivatives, acetophenone derivatives, benzophenone derivatives, and azo compounds. Examples of the pyrolysis-type polymerization initiators include persulfates (sodium persulfate, potassium persulfate, ammonium persulfate), peroxides (hydrogen peroxide, t-butyl peroxide, methyl ethyl ketone peroxide), and azo compounds (2,2'-azobis(2-amidinopropane) dihydrochloride and 2,2'-azobis[2-(2-imidazolin-2-yl) propane]dihydrochloride). Examples of the redox-type polymerization initiators include systems each of which is a combination of any of the persulfates and peroxides and a reducing compound such as L-ascorbic acid or sodium hydrogen sulfite. A photolytic-type polymerization initiator and a pyrolysis-type polymerization initiator can be used in combination with each other as a preferable form.

The polymerization initiator is used in an amount within a range of preferably 0.001 mol % to 2 mol %, more preferably 0.01 mol % to 0.1 mol %, with respect to the monomer. The amount of use of the polymerization initiator being not less than 0.001 mol % eliminates the risk of an increase in the amount of residual monomer. The amount of use of the polymerization initiator being not more than 2 mol % prevents polymerization control from being difficult.

(Polymerization Method)

A polymerization method usable during this step is not limited to any particular one. In terms of the water absorbent property, ease of control of polymerization, and the like, the polymerization method is preferably vapor phase spray polymerization, vapor phase droplet polymerization, aqueous solution polymerization, or reversed phase suspension polymerization, more preferably aqueous solution polymerization or reversed phase suspension polymerization, even more preferably aqueous solution polymerization. Continuous aqueous solution polymerization is particularly preferable, and can be any one of continuous belt polymerization and continuous kneader polymerization.

Specific examples of the form of continuous belt polymerization include those disclosed in U.S. Pat. Nos. 4,893,999, 6,241,928, and U.S. Patent Application Publication No. 2005/0215734. Specific examples of the form of continuous kneader polymerization include those disclosed in U.S. Pat. Nos. 6,987,151 and 6,710,141. In a case where these forms of continuous aqueous solution polymerization are employed, it is possible to improve efficiency with which a water-absorbing resin is produced.

In a case where the unsaturated monomer is to be subjected to aqueous solution polymerization, the aqueous solution has a monomer concentration that depends on the temperature of the aqueous solution and the kind of the monomer and that is not limited to any particular value. The monomer concentration is, however, within a range of preferably 10% by mass to 70% by mass, more preferably 20% by mass to 60% by mass.

Polymerization of the unsaturated monomer is initiated through addition of the polymerization initiator, irradiation of an activation energy ray such as an ultraviolet ray, an electron ray, or a γ ray, or a combination of the two. The polymerization reaction has a reaction temperature that is selected as appropriate depending on the kind of the polymerization initiator to be used and the kind of the activation energy ray to be used and that is not limited to any particular one. The reaction temperature is, however, within a range of preferably 15° C. to 130° C., more preferably 20° C. to 120° C. The reaction temperature being within the above preferable range eliminates the risks of an increase in the amount of residual monomer of a water-absorbing resin to be obtained and an excessive self-crosslinking reaction, thereby preferably eliminating the risk of a decrease in the water absorption performance of a water-absorbing resin to be obtained.

Reversed phase suspension polymerization is a method in which an aqueous monomer solution is suspended in a hydrophobic organic solvent for polymerization, and is disclosed in, for example, U.S. Pat. Nos. 4,093,776, 4,367,323, 4,446,261, 4,683,274, and 5,244,735.

Aqueous solution polymerization is a method in which an aqueous monomer solution is polymerized without use of a dispersion solvent, and is disclosed in, for example, U.S. Pat. Nos. 4,625,001, 4,873,299, 4,286,082, 4,973,632, 4,985,518, 5,124,416, 5,250,640, 5,264,495, 5,145,906, 5,380,808, European Patent No. 0811636, European Patent No. 0955086, and European Patent No. 0922717. A solvent other than water may be used as necessary in combination with water. The kind and the like of the other solvent are not particularly limited.

Thus, using the unsaturated monomer, the polymerization initiator, and the like for a polymerization method disclosed in any of the above patent documents makes it possible to obtain a water-absorbing resin.

(4-2) Gel-Crushing Step

This step is a step of gel-crushing a hydrogel, which has been obtained through the polymerization step, with use of, for example, a kneader, a screw extruder such as a meat chopper, or a gel-crusher such as a cutter mill in order to obtain a particulate hydrogel. The present specification regards such a particulate hydrogel as a form of "water-absorbing resin particles". In a case where the polymerization step is carried out through kneader polymerization, such a step is equivalent to a combination of the polymerization step and the gel-crushing step which are carried out simultaneously. In a case where a particulate hydrogel is directly obtained through a polymerization process such as vapor phase polymerization or reversed phase suspension polymerization, the gel-crushing step may not be carried out.

Gel-crushing conditions and forms other than the above that are preferably used for the present invention are disclosed in International Publication No. 2011/126079. The present specification describes the gel-crushing step before describing the drying step described below. The gel-crushing step may, however, be carried out after the drying step.

(4-3) Drying Step

This step is a step of drying the hydrogel, which has been obtained through the polymerization step and/or the gel-crushing step, so as to obtain a dry polymer.

The drying method is not limited to any particular one as long as the method allows an intended moisture content to be achieved, and may be any of various methods. Specific examples include thermal drying, hot air drying, drying under reduced pressure, infrared drying, microwave drying, dehydration by azeotropy with a hydrophobic organic solvent, and high-humidity drying involving use of high-temperature water vapor. In a case where hot air drying is carried out among the above examples, the hot air has a temperature within a range of normally 60° C. to 250° C., preferably 100° C. to 220° C., more preferably 120° C. to 200° C. The duration of drying depends on the surface area and moisture content of the hydrogel and the kind of the drying device. Thus, the duration of drying is selected as appropriate from within a range of, for example, 1 minute to 5 hours in order to achieve an intended moisture content.

A hydrogel obtained through reversed phase suspension polymerization does not need to undergo a gel-crushing process, and can be dried through the following procedure: A hydrogel is dispersed in a hydrocarbon-based organic solvent such as hexane. The solution is subjected to azeotropic dehydration so that the hydrogel has a moisture content of not more than 40% by mass, preferably not more than 30% by mass. Then, the solution is subjected to decantation or evaporation for separation of the organic solvent and the hydrogel. This produces water-absorbing resin particles. Thus, in a case where the polymerization step involves reversed phase suspension polymerization, a particulate water-absorbing resin is obtained at the time of the end of the drying process. The chelating agent may be added at any stage thereafter. In this case as well, a further, drying process may be carried out as necessary. Surface-crosslinking may be carried out at the same time as the drying during the drying step.

The moisture content after the drying step is determined from a drying loss (for which drying is carried out under the condition that powder or 1 g of particles is heated at 180° C. for 3 hours). The resin solid content (which is calculated by 100−moisture content) after the drying is adjusted to be preferably not less than 80% by mass, more preferably 85% by mass to 99% by mass, even more preferably 90% by mass to 98% by mass, to produce a dry polymer.

(4-4) Pulverizing Step, Classification Step

These steps are steps of pulverizing and/or classifying the dry polymer, which is prepared through the drying step, and adjusting the particle sizes of the pulverized polymer to particle sizes within a predetermined range (classification step) so as to obtain water-absorbing resin particles. The water-absorbing resin particles obtained after the pulverization step may be referred to as "crushed substance".

Reversed phase suspension polymerization involves controlling the particle diameters during dispersion polymerization. The pulverizing step is thus optional. However, as necessary, the polymer may be pulverized, or agglomerates may be crushed (that is, an operation for loosening the agglomeration). With aqueous solution polymerization, it is possible to, depending on the degree of gel grain refining during and after the polymerization, omit a pulverizing step following the drying. It is, however, preferable to carry out pulverization and classification.

The dry polymer obtained through the drying step may directly be used as a water-absorbing resin. It is, however, preferable to adjust the particle sizes to particular particle sizes preferably through pulverization and classification in order to obtain a water-absorbing resin composition in accordance with an embodiment of the present invention. The particle sizes can be appropriately adjusted not only in the pulverization step and the classification step but also in the polymerization step, a fine powder recycling step, a granulation step, or the like step. A particle size adjusting method in the classification step of an embodiment of the present invention is not limited to any particular one, and can be, for example, sieve classification involving use of a JIS standard sieve (JIS Z8801-1 (2000)), airflow classification, or the like.

For an embodiment of the present invention, water-absorbing resin particles (base polymer) obtained through the pulverizing and classification steps have a weight average particle diameter (D50) of preferably 200 μm to 600 μm, more preferably 250 μm to 550 μm, even more preferably 300 μm to 500 μm, particularly preferably 350 μm to 450 μm. The proportion of particles each having a particle diameter of less than 150 μm is preferably not more than 10% by mass, more preferably not more than 5% by mass, even more preferably not more than 1% by mass, particularly preferably not more than 0.5% by mass. The proportion of particles each having a particle diameter of not less than 850 μm is preferably not more than 5% by mass, more preferably not more than 3% by mass, even more preferably not more than 1% by mass, particularly preferably not more than 0.5% by mass. These proportions each have a lower limit that is preferably as low as possible. The lower limit is desirably 0% by mass, but may be approximately 0.1% by mass. The logarithmic standard deviation (σζ) of a particle size distribution is preferably within a range of 0.20 to 0.50, more preferably 0.25 to 0.40, even more preferably 0.27 to 0.35. These particle sizes are as measured with use of a standard sieve in conformity to a measurement method disclosed in U.S. Pat. No. 7,638,570 or EDANA ERT420.2-02.

The particle sizes above apply also to a water-absorbing resin composition obtained as an embodiment of the present invention. Thus, in order for a water-absorbing resin composition to maintain particle sizes within the above range, it is preferable to carry out a surface-crosslinking treatment, and it is more preferable to carry out a sizing step after the surface-crosslinking treatment for particle size adjustment.

Further, it is preferable to remove fine particles (that is, particles each having a particle diameter of less than 150 μm) by classification during a sizing step that follows the surface-crosslinking treatment. A large amount of fine particles of a water-absorbing resin composition in a diaper is not preferable because a problem such as gel on skin may occur when the diaper is in use.

During the process of producing a water-absorbing resin composition, water-absorbing resin particles can be transported, for example, with use of a bucket conveyor or a spring conveyor or by air transport. However, air transport is preferable because it has a small maintenance load and few conduit-path constraints. Further, to prevent a conduit wear and grain breakage, low-speed plug-type high-concentration air transport is preferable.

(4-5) Surface-Crosslinking Step

The water-absorbing resin particles obtained through the above steps are preferably subjected to a surface-crosslinking treatment so that a crosslinking density at and in the vicinities of the surfaces of the water-absorbing resin particles is increased and the properties of the water-absorbing resin are improved.

The following description will discuss a surface-crosslinking compositions (surface-crosslinking raw materials) suitably used in the method for producing a water-absorbing resin composition.

In the method for producing a water-absorbing resin composition, a surface-crosslinking agent used in the above surface-crosslinking step is not limited to any particular one, provided that the surface-crosslinking agent imparts excellent properties to the water-absorbing resin particles to be obtained. However, it is preferable to use one or more kinds, in combination, selected from polyvalent alcohol compounds, epoxy compounds, polyvalent amine compounds, condensates of a polyvalent amine compound and a haloepoxy compound, oxazoline compounds, monooxazolidinone compounds, dioxazolidinone compounds, polyoxazolidinone compounds, polyvalent metal salts, alkylene carbonate compounds, and the like.

More specifically, any of surface-crosslinking agents disclosed in U.S. Pat. Nos. 6,228,930, 6,071,976, 6,254,990, and the like can be used. That is, the surface-crosslinking agents are exemplified by polyvalent alcohol compounds such as monoethylene glycol, diethylene glycol, triethylene glycol, tetraethylene glycol, polyethylene glycol, monopropylene glycol, 1,3-propanediol, dipropylene glycol, 2,3,4-trimethyl-1,3-pentanediol, polypropylene glycol, glycerin, polyglycerin, 2-butene-1,4-diol, 1,4-butanediol, 1,3-butanediol, 1,5-pentanediol, 1,6-hexanediol, and 1,2-cyclohexane dimethanol; epoxy compounds such as ethylene glycol diglycidyl ether and glycidol; polyvalent amine compounds such as ethylenediamine, diethylenetriamine, triethylenetetramine, tetraethylenepentamine, pentaethylenehexamine, polyethyleneimine, and polyamidepolyamine; haloepoxy compounds such as epichlorohydrin, epibromhydrin, and α-methylepichlorohydrin; condensates of a polyvalent amine compound and a haloepoxy compound; oxazolidinone compounds such as 2-oxazolidinone; alkylene carbonate compounds such as ethylene carbonate; and the like.

Note that an ionic bonding surface-crosslinking agent, a polyvalent metal salt, and a polyamine polymer can be used in addition to the surface-crosslinking agent. Note also that, in addition to or instead of an organic surface-crosslinking agent, an inorganic surface-crosslinking agent can be used so as to improve liquid permeability and others. Examples of the inorganic surface-crosslinking agent to be used include divalent or more, preferably trivalent or tetravalent, metal salts (organic salts or inorganic salts) and hydroxides. Examples of such polyvalent metals which can be used include aluminum, zirconium, and the like. Examples of aluminum include aluminum lactate and aluminum sulfate.

As later described, the water-absorbing resin composition in accordance with an embodiment of the present invention preferably further contains a polyvalent metal salt and/or inorganic fine particles. In the production method in accordance with an embodiment of the present invention, the polyvalent metal salt and/or the inorganic fine particles is/are preferably added to the water-absorbing resin simultaneously with, before, or after surface-crosslinking. More preferably, the polyvalent metal salt and/or the inorganic fine particles is/are added so that the polyvalent metal salt and/or the inorganic fine particles is/are distributed on and in the vicinities of the surfaces of the water-absorbing resin particles.

Of those surface-crosslinking agents, a covalent surface-crosslinking agent is preferably used so as to cause various properties of the water-absorbing resin particles to be as excellent as possible. An epoxy compound, a haloepoxy compound, and an oxazolidinone compound each of which can react at a low temperature are preferably used, or alternatively at least any one of an epoxy compound and a haloepoxy compound is more preferably used, or alternatively an epoxy compound is particularly preferably used, so as to prevent a decrease in moisture content during the surface-crosslinking (and so as to enhance stability of the water-absorbing resin against impact).

Note that, in a case where the surface-crosslinking is carried out at a high temperature with use of a dehydration reactive surface-crosslinking agent selected from alkylene carbonates and polyvalent alcohols, water is further added, as appropriate, after the surface-crosslinking so as to adjust the moisture content to a later described moisture content. In a case where a polyvalent alcohol is used as the dehydration reactive surface-crosslinking agent, preferably a polyvalent alcohol having 2 to 10 carbon atoms, more preferably a polyvalent alcohol having 3 to 8 carbon atoms is used as the polyvalent alcohol.

An amount of the surface-crosslinking agent varies depending on, for example, a kind of the surface-crosslinking agent used and a combination of a precursor of the water-absorbing resin and the surface-crosslinking agent, but is preferably 0.001 parts by mass to 10 parts by mass, more preferably 0.01 parts by mass to 5 parts by mass, even more preferably 0.05 parts by mass to 2 parts by mass, particularly preferably 0.1 parts by mass to 1 part by mass, with respect to 100 parts by mass of the water-absorbing resin particles. In a case where the amount of the surface-crosslinking agent is small, the centrifuge retention capacity (CRC) tends to increase, as compared with a case where the amount of the surface-crosslinking agent is large. By using the surface-crosslinking agent within the above range, it is possible to obtain a water-absorbing resin composition having a centrifuge retention capacity (CRC) of not less than 35 g/g.

In a case where the surface-crosslinking treatment is carried out, it is preferable to use water together with the surface-crosslinking agent. An amount of the water used during the surface-crosslinking treatment varies depending on a moisture content of the water-absorbing resin used, but is typically 0.1 parts by mass to 20 parts by mass, preferably 0.5 parts by mass to 10 parts by mass, even more preferably 1 part by mass to 5 parts by mass, with respect to 100 parts by mass of the water-absorbing resin.

In a case where the surface-crosslinking agent or an aqueous solution of the surface-crosslinking agent is mixed with the water-absorbing resin, a hydrophilic organic solvent or a third substance can be used as a mixture auxiliary agent.

Examples of the hydrophilic organic solvent include: lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and methoxy(poly)ethylene glycol; amides such as ε-caprolactam and N,N-dimethylformamide; sulfoxides such dimethyl sulfoxide; and polyvalent alcohols such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerin, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, an oxyethylene-oxypropylene block copolymer, pentaerythritol, and sorbitol.

Note that, in a case where a polyvalent alcohol reacts with the water-absorbing resin, such a polyvalent alcohol is classified into the surface-crosslinking agent, whereas in a case where a polyvalent alcohol does not react with the water-absorbing resin, such a polyvalent alcohol is classified into the hydrophilic organic solvent. Whether or not a polyvalent alcohol reacts with the water-absorbing resin can be easily determined by an amount of a remaining polyvalent alcohol or an increase in ester (which can be detected by, for example, carrying out an IR analysis).

An amount of the hydrophilic organic solvent varies depending on, for example, a kind, a particle diameter, and a moisture content of the water-absorbing resin, but is preferably not more than 10 parts by mass, more preferably 0.1 parts by mass to 5 parts by mass, with respect to 100 parts by mass of the water-absorbing resin composition. As the third substance, an inorganic acid, an organic acid, a polyamino acid, or the like which are disclosed in the specification of European Patent No. 0668080 can be caused to be present. Those mixture auxiliary agents can be each caused to act as a surface-crosslinking agent. Note, however, that the mixture auxiliary agents as surface-crosslinking agents are each preferably a mixture auxiliary agent which does not decrease a water absorption performance of the water-absorbing resin which has been surface-crosslinked with use of the mixture auxiliary agent. In particular, a volatile alcohol having a boiling point of less than 150° C. is desirable because the volatile alcohol volatilizes during the surface-crosslinking treatment and does not remain.

In order that the water-absorbing resin and the surface-crosslinking agent are more uniformly mixed together, a non-crosslinking water-soluble inorganic base (preferably, alkali metal salt, ammonium salt, alkali metal hydroxide, and ammonia or hydroxide thereof) or an irreducible alkali metal salt pH buffer solution (preferably, hydrogencarbonate, dihydrogenphosphate, hydrogenphosphate, or the like) can be caused to be present in a case where the water-absorbing resin and the surface-crosslinking agent are mixed together. An amount of the non-crosslinking water-soluble inorganic base or the irreducible alkali metal salt pH buffer solution varies depending on, for example, the kind and the particle diameter of the water-absorbing resin, but is preferably 0.005 parts by mass to 10 parts by mass, more preferably 0.05 parts by mass to 5 parts by mass, with respect to 100 parts by mass of the water-absorbing resin composition.

(Method of Adding Surface-Crosslinking Agent)

The surface-crosslinking agent can be added by various methods. For example, in a case where the water-absorbing resin is obtained by aqueous solution polymerization, it is preferable to use a method of mixing, as necessary, the surface-crosslinking agent with water and/or a hydrophilic organic solvent in advance and dropping, more preferably spraying, the surface-crosslinking agent onto the water-absorbing resin during or after the drying step. The surface-crosslinking agent is sprayed in the form of liquid droplets having an average size of preferably 0.1 μm to 300 μm, more preferably 1 μm to 200 μm.

In the production method in accordance with an embodiment of the present invention, the surfactant and/or the lubricant is preferably added in accordance with the above method. The surfactant and/or the lubricant can be added together with the surface-crosslinking agent or can be alternatively added separately from the surface-crosslinking agent. By adding the surfactant and/or the lubricant in such a stage and using the chelating agent in combination, it is possible to suitably realize both use of the water-absorbing resin having a high centrifuge retention capacity (CRC) and impartment of a sufficient urine resistance.

A mixing apparatus used to mix the water-absorbing resin, the surface-crosslinking agent, the water, and the hydrophilic organic solvent together preferably has a great mixing power so that those compounds are uniformly and absolutely mixed together. Suitable examples of such a mixing apparatus include cylindrical mixers, double-wall conical mixers, high-speed stirring mixer, V-shaped mixers, ribbon mixers, screw type mixers, twin-arm kneaders, pulverizing type kneaders, rotating mixers, air mixtures, Turbulizer, batch type Loedige mixers, continuous type Loedige mixers, and the like. Note that any of those mixing apparatuses can be also used to mix the chelating agent or any other additive(s) (polyvalent metal salt, inorganic fine particles, water, dust inhibiting agent, and the like) (later described) with the water-absorbing resin. The any other additive(s) can be mixed with the water-absorbing resin, together with the surface-crosslinking agent or separately from the surface-crosslinking agent.

After the surface-crosslinking agent and the water-absorbing resin are mixed together, a heating treatment is preferably carried out. As a condition under which the heating treatment is carried out, a temperature of the water-absorbing resin or a temperature of a heating medium which is used in the heating treatment is preferably 60° C. to 250° C., more preferably 100° C. to 230° C., even more preferably 150° C. to 200° C. A heating time during which the heating treatment is carried out is preferably 1 minute to 2 hours. As such a heating temperature becomes lower and as the heating time becomes shorter, the centrifuge retention capacity (CRC) of the water-absorbing resin to be obtained tends to increase, as compared with a case where the heating temperature is higher and a case where the heating time is longer. Suitable example combinations of the heating temperature and the heating time can be 0.1 hours to 1.0 hour at 200° C. and 0.2 hours to 2.0 hours at 180° C. According to such examples, it is possible to produce a water-absorbing resin composition having a centrifuge retention capacity (CRC) of not less than 35 g/g.

Note that, in a case where an alkylene carbonate or a polyvalent alcohol is used as the surface-crosslinking agent, the temperature of the water-absorbing resin or the temperature of the heating medium which is used in the heating treatment is preferably 100° C. to 250° C., more preferably 150° C. to 250° C., even more preferably 170° C. to 210° C. In a case where an alkylene carbonate or a polyvalent alcohol is used as the surface-crosslinking agent and the heating treatment is carried out within such a temperature range, the moisture content of the water-absorbing resin composition is adjusted to the later described moisture content of the water-absorbing resin composition after the surface-crosslinking.

In a case where a mixture of the surface-crosslinking agent and the water-absorbing resin is heated, the mixture can be heated while the mixture is left to stand still or can be alternatively heated while a mixing means such as stirring is used. In view of uniform heating throughout the entire mixture, it is preferable to heat the mixture while the mixture is stirred and mixed. Particularly, a batch type paddle mixer or a continuous type paddle mixer is more preferable, and a continuous paddle mixer is still more preferable.

Further, in a case where the water-absorbing resin is obtained by reversed phase suspension polymerization, it is possible to obtain a surface-crosslinked water-absorbing resin by dispersing the surface-crosslinking agent, preferably a glycidyl ether compound, in a hydrophobic organic solvent used in the reversed phase suspension polymerization while, for example, the moisture content of the hydrogel is not more than 50% by mass, preferably not more than 40% by mass, more preferably not more than 30% by mass (a lower limit of the moisture content is preferably not less than 5% by mass, more preferably not less than 10% by mass, particularly preferably not less than 15% by mass) during and/or after azeotropic dehydration after the reversed phase suspension polymerization. In this case, it is preferable to add the surfactant and/or the lubricant to the hydrophobic organic solvent.

(4-6) Additive Adding Step

An additive adding step is a step of adding an additive(s) to the water-absorbing resin before, during, or after the surface-crosslinking, preferably after the surface-crosslinking, so as to impart various functions to the water-absorbing resin. The additive adding step includes one or more steps.

Examples of the additive(s) include dust inhibiting agents, water, polyvalent metal salts, inorganic fine particles, surfactants, perfumes, foaming agents, pigments, dyes, fertilizers, and the like. The additive(s) can impart or enhance a function(s). The function(s) imparted is/are not limited in particular, but examples of the function(s) include transportability, liquid permeability, a resistance to moisture absorption blocking, a urine resistance, an antibacterial property, a deodorizing property, and a reduction in amount of dust of the water-absorbing resin composition.

In a preferred embodiment of the present invention, the water-absorbing resin composition contains a dust inhibiting agent.

In another preferred embodiment of the present invention, the water-absorbing resin composition contains a polyvalent metal salt and/or inorganic fine particles.

In still another preferred embodiment of the present invention, the water-absorbing resin composition contains water.

The method in accordance with an embodiment of the present invention for producing a water-absorbing resin composition includes an adding step of adding such an additive(s). In the adding step, the additive(s) is/are preferably distributed on the surfaces of the particles. The adding step is preferably carried out with respect to the water-absorbing resin particles which have been dried.

An amount of the additive(s) is less than 10% by mass, preferably less than 5% by mass, more preferably less than 1% by mass, with respect to 100% by mass of the water-absorbing resin which has been surface-crosslinked, unless otherwise specified. The additive(s) can be added in the surface-crosslinking step or can be alternatively added in another step.

In the production method in accordance with an embodiment of the present invention, the chelating agent is preferably added in the additive adding step, more preferably added in the additive adding step which is carried out after the surface-crosslinking. By adding the chelating agent in the additive adding step, it is possible to cause the chelating agent to be localized on and in the vicinity of a surface of the water-absorbing resin, and possible to sufficiently achieve an effect of preventing generation of a post-degradation-test one-hour eluted soluble component. Note that the chelating agent can be added together with the additive(s) other than the chelating agent. This is preferable because it is possible to reduce the number of production steps.

(4-7) Fine Powder and Dust Removing Step (Second Classification Step)

A fine powder and dust removing step indicates a step of removing at least part of fine powder and dust of the water-absorbing resin (in particular, water-absorbing resin particles capable of passing through a classification mesh having a mesh size of 150 μm) by further carrying out a classification step (in other words, second classification step) after the surface-crosslinking step.

The fine powder and dust of the water-absorbing resin can be removed in the classification step (first classification step) which is carried out before the surface-crosslinking. However, due to classification efficiency, it is not always possible to remove 100% of the fine powder and dust. For example, even in a case where classification is carried out before the surface-crosslinking while an upper limit and a lower limit of the mesh size of the classification mesh is set to 850 μm and 150 μm, respectively, or 710 μm and 150 μm, respectively, as in Production Examples 1 and 2 (later described), a few percent to less than one percent of water-absorbing resin particles that pass through a classification mesh having a mesh size of 150 μm may be included in the water-absorbing resin particles which have been subjected to the classification. Furthermore, since the fine powder and dust may also be generated by damage caused in the surface-crosslinking step, it is preferable to carry out the classification again after the surface-crosslinking so as to remove the fine powder and dust of the water-absorbing resin (second classification step).

The fine powder and dust removing step is preferably carried out before the additive adding step is carried out. However, the fine powder and dust removing step can be carried out only after the additive adding step or can be alternatively carried out both before and after the additive adding step. In a case where the fine powder and dust removing step is carried out both before and after the additive adding step, the fine powder and dust removing step which is carried out after the additive adding step can be also referred to as a "third classification step." In the fine powder and dust removing step, it is possible to employ gravity classification which is carried out with use of a sieve mesh, as well as classification which is carried out with use of airflow. Alternatively, classification which is carried out with use of a combination of a sieve mesh and airflow can be employed.

The mesh size of the classification mesh used in the fine powder and dust removing step is preferably not more than 300 μm, more preferably not more than 260 μm, even more preferably not more than 210 μm, most preferably not more than 180 μm. A proportion of the water-absorbing resin particles which are capable of passing through the classification mesh having a mesh size of 150 μm and which are removed is preferably not less than 0.1 parts by mass, more preferably not less than 0.5 parts by mass, most preferably not less than 1.0 part by mass, with respect to 100 parts by mass of the water-absorbing resin particles which have been surface-crosslinked.

In a case where the classification is carried out with use of airflow, a flow of air, a flow of a nitrogen gas, a flow of a mixed gas of these gases, or the like can be used as the airflow. The airflow is preferably airflow having a temperature equal to or lower than its dew point. A volume of the airflow used for the classification (so-called air velocity) is not limited in particular, provided that the volume of the airflow allows movement of powder. The volume of the airflow is preferably adjusted as appropriate depending on a direction (direction of gravity, horizontal direction, and the like) of the movement of the powder and flowability of the powder.

The "water-absorbing resin particles which include the particles capable of passing through the classification mesh having a mesh size of 150 μm" which have been removed are mixed with preferably water (and/or an aqueous solution) (more preferably, after mixed with fine particles which have been removed before the surface-crosslinking step), granulated, and then recycled in the drying step.

[5] Water-Absorbing Resin Composition

An aspect of the present invention is a water-absorbing resin composition (first water-absorbing resin composition) having the following properties:

(1) A centrifuge retention capacity (CRC) being not less than 35 g/g;

(2) A post-degradation-test one-hour eluted soluble component being not more than 19% by mass;

(3) An absorbency against pressure 0.7 psi (AAP0.7) being not less than 10 g/g; and (4) A content of a water-absorbing resin in dust being not more than 300 ppm with respect to a total mass of the water-absorbing resin composition.

A water-absorbing resin composition (second water-absorbing resin composition) in accordance with another aspect of the present invention contains water-absorbing resin particles and a chelating agent, the water-absorbing resin composition containing the chelating agent in an amount of not more than 1.0% by mass with respect to a total mass of the water-absorbing resin composition, the water-absorbing resin composition having a centrifuge retention capacity (CRC) of not less than 35 g/g, the water-absorbing resin composition including a post-degradation-test one-hour eluted soluble component at a proportion of not more than 19%.

A water-absorbing resin composition in accordance with an embodiment of the present invention more preferably contains water-absorbing resin particles, a surfactant and/or a lubricant, and a chelating agent.

The water-absorbing resin composition (for example, the first water-absorbing resin composition and the second water-absorbing resin composition) in accordance with another embodiment of the present invention has the following properties: (1) a centrifuge retention capacity (CRC) being not less than 35 g/g; (2) a post-degradation-test one-hour eluted soluble component being not more than 19% by mass; (3) an absorbency against pressure 0.7 psi (AAP0.7) being not less than 10 g/g; and (4) a content of a water-absorbing resin in dust being not more than 300 ppm with respect to the total mass of the water-absorbing resin composition.

A shape of each of the water-absorbing resin particles contained in the water-absorbing resin composition in accordance with an embodiment of the present invention is not limited in particular. For example, the water-absorbing resin particles can each have a pulverized non-uniform shape (non-uniform shape), a spherical shape, a fibrous shape, a bar shape, a substantially spherical shape, or a flat shape. In consideration of use of the water-absorbing resin composition for a sanitary product such as a diaper for a child, the water-absorbing resin particles each preferably has a non-uniform shape out of the above particle shapes, in view of diffusion of a liquid (urine), difficulty of drop of the water-absorbing resin particles from pulp, and the like.

The amount of the chelating agent contained in the water-absorbing resin composition in accordance with an embodiment of the present invention is preferably 1 ppm to 10000 ppm, more preferably 5 ppm to 7000 ppm, even more preferably 10 ppm to 5000 ppm, particularly preferably 50 ppm to 4000 ppm, especially even more preferably 80 ppm to 3000 ppm, most preferably 100 ppm to 2000 ppm with respect to the total mass of the water-absorbing resin composition.

The amount of the chelating agent contained in the water-absorbing resin composition in accordance with an embodiment of the present invention is identical to the amount, described in [3], of the chelating agent added to the water-absorbing resin particles. That is, the amount of the chelating agent is 0.0001 parts by mass to 1.0 part by mass with respect to 100 parts by mass as the total mass of the water-absorbing resin composition, and a more preferable amount is also identical to that described in [3].

Note that the above amount is 0.0001% by mass to 1.0% by mass, preferably 0.0005% by mass to 0.7% by mass, more preferably 0.001% by mass to 0.05% by mass, even more preferably 0.005% by mass to 0.03% by mass, particularly preferably 0.008% by mass to 0.03% by mass, most preferably 0.01% by mass to 0.03% by mass, with respect to 100% by mass of the total mass of the water-absorbing resin composition.

The water-absorbing resin composition in accordance with an embodiment of the present invention can be produced by the method described in the above [4]. However, how to produce the water-absorbing resin composition is not limited to such a method.

The centrifuge retention capacity (CRC) of the water-absorbing resin composition in accordance with an embodiment of the present invention only needs to be not less than 35 g/g, but is more preferably not less than 36 g/g, even more preferably not less than 37 g/g, particularly preferably not less than 38 g/g, most preferably not less than 39 g/g. An upper limit of the CRC is preferably as high as possible, but is preferably not more than 70 g/g, more preferably not more than 65 g/g, even more preferably not more than 60 g/g, particularly preferably not more than 55 g/g, most preferably not more than 50 g/g, in view of balance between the CRC and other properties (particularly, degradable soluble component).

The post-degradation-test one-hour eluted soluble component of the water-absorbing resin composition in accordance with an embodiment of the present invention is preferably not more than 19% by mass, more preferably not more than 18% by mass, even more preferably not more than 17% by mass. In a case where the post-degradation-test one-hour eluted soluble component is not more than 19% by mass, the water-absorbing resin composition has an excellent urine resistance. A lower limit of the post-degradation-test one-hour eluted soluble component is preferably as low as possible, but presence of approximately 2% by mass, 5% by mass, or 8% by mass of the post-degradation-test one-hour eluted soluble component can be allowed, in view of balance between the post-degradation-test one-hour eluted soluble component and other properties (particularly, degradable soluble component). Note, here, that the post-degradation-test one-hour eluted soluble component indicates a value measured by a method later described in Examples below. According to the water-absorbing resin composition in accordance with an embodiment of the present invention, it is possible to realize both use of a water-absorbing resin having a high centrifuge retention capacity (CRC) and impartment of a sufficient urine resistance.

The absorbency against pressure 0.7 psi (AAP0.7) of the water-absorbing resin composition in accordance with an embodiment of the present invention is preferably not less than 10 g/g, more preferably not less than 13 g/g, even more preferably not less than 15 g/g, particularly preferably not less than 18 g/g, most preferably not less than 20 g/g. An upper limit value of the absorbency against pressure 0.7 psi (AAP0.7) is not limited in particular, but is preferably not more than 30 g/g, in view of balance between a production cost and the absorbency against pressure 0.7 psi (AAP0.7) and other properties.

In a case where the AAP0.7 psi is not less than 10 g/g, an excessively large amount of a liquid is not released (generally, referred to as "Re-Wet") when a load is applied to an absorbent body. The AAP0.7 psi of not less than 10 g/g is therefore suitable for an absorbent body of a sanitary material such as a disposable diaper. Note that AAP can be controlled on the basis of, for example, a particle size and/or a surface-crosslinking agent.

The water-absorbing resin composition in accordance with an embodiment of the present invention has a surface tension, which is measured by a method described in Examples, of preferably not less than 65 mN/m, more preferably not less than 66 mN/m, even more preferably not less than 67 mN/m, particularly preferably not less than 68 mN/m, most preferably not less than 69 mN/m. An upper limit value of the surface tension is not limited in particular, but is preferably not more than 75 mN/m, more preferably not more than 73 mN/m. Depending on circumstances, the upper limit value can be not more than 70 mN/m.

In a case where the surface tension is not less than 65 mN/m, an excessively large amount of a liquid is not released (generally, referred to as "Re-Wet") when a load is applied to an absorbent body. The surface tension of not less than 65 mN/m is therefore suitable for an absorbent body of a sanitary material such as a disposable diaper. Note that the "surface tension" as used in the present specification indicates a value measured by a method described in Examples.

The surfactant contained in the water-absorbing resin composition in accordance with an embodiment of the present invention has HLB (hydrophile-lipophile balance; defined by the Griffin method) of preferably 8 to 18, more preferably 9 to 17, even more preferably 10 to 17, particularly preferably 11 to 16, most preferably 12 to 16.

In a case where the HLB falls with the above range, it is possible to achieve both a high centrifuge retention capacity and a sufficient urine resistance.

An acid value of the surfactant contained in the water-absorbing resin composition in accordance with an embodiment of the present invention is preferably 0.001 mgKOH/g to 2.5 mgKOH/g, more preferably 0.001 mgKOH/g to 1.5 mgKOH/g, even more preferably 0.01 mgKOH/g to 1.0 mgKOH/g. In a case where the acid value of the surfactant is not more than 2.5, an increase in hydrophobicity of the water-absorbing resin composition is suppressed. This allows a sufficiently high liquid absorbing speed and sufficiently reduced re-wet. The acid value of not more than 2.5 is therefore preferable.

An amount of the surfactant contained in the water-absorbing resin composition in accordance with an embodiment of the present invention is 0.0001 parts by mass to 0.1 parts by mass, preferably 0.0001 parts by mass to 0.05 parts by mass, more preferably 0.0003 parts by mass to 0.02 parts by mass, even more preferably 0.0004 parts by mass to 0.015 parts by mass, particularly preferably 0.0005 parts by mass to 0.01 parts by mass, most preferably 0.0005 parts by mass to 0.005 parts by mass, with respect to 100 parts by mass as the total mass of the water-absorbing resin composition.

In a case where the amount of the surfactant is not more than 0.0001 parts by mass, it is possible to prevent occurrence of stickiness of an absorbent body, and possible to prevent an excessive increase in re-wet. The amount of not more than 0.0001 parts by mass is therefore suitable for an absorbent body of a sanitary material such as a disposable diaper.

The surfactant and/or the lubricant contained in the water-absorbing resin composition in accordance with an embodiment of the present invention is/are preferably present more on and in the vicinities of surfaces of the water-absorbing resin particles than inside the water-absorbing resin particles. Specifically, the surfactant and/or the lubricant contained in the water-absorbing resin composition is/are preferably localized in a region ranging from a surface of each of the water-absorbing resin particles to part approximately 10 μm deep from the surface. That is, a proportion of the surfactant and/or the lubricant which is/are present on and in the vicinities of the surfaces of the water-absorbing resin particles contained in the water-absorbing resin composition is preferably not less than 50%, more preferably not less than 70%, even more preferably not less than 90%, with respect to a total mass of the surfactant and/or the lubricant which is/are contained in the entire water-absorbing resin composition. The fact that the surfactant and/or the lubricant is/are present more on and in the vicinities of the surfaces of the water-absorbing resin particles allows an improvement in stickiness of an absorbent body including the water-absorbing resin particles.

Note that the surfactant and/or the lubricant may or may not be contained inside the water-absorbing resin particles (i.e., in a region of each of the water-absorbing resin particles, excluding the region ranging from the surface of each of the water-absorbing resin particles to the part approximately 10 μm deep from the surface).

The chelating agent contained in the water-absorbing resin composition in accordance with an embodiment of the present invention is preferably present more on and in the vicinities of the surfaces of the water-absorbing resin particles than inside the water-absorbing resin particles. Specifically, the chelating agent contained in the water-absorbing resin composition is preferably localized in the region ranging from the surface of each of the water-absorbing resin particles to the part approximately 10 μm deep from the surface. That is, a proportion of the chelating agent which is present on and in the vicinities of the surfaces of the water-absorbing resin particles contained in the water-absorbing resin composition is preferably not less than 50%, more preferably not less than 70%, even more preferably not less than 90%, with respect to a total mass of the chelating agent which is contained in the entire water-absorbing resin composition. The fact that the chelating agent is present more on and in the vicinities of the surfaces of the water-absorbing resin particles allows an improvement in stickiness of an absorbent body including the water-absorbing resin particles.

Note that the chelating agent may or may not be contained inside the water-absorbing resin particles (i.e., in the region of each of the water-absorbing resin particles, excluding the region ranging from the surface of each of the water-absorbing resin particles to the part approximately 10 μm deep from the surface).

(1) The surfactant and/or the lubricant and (2) the chelating agent which are contained in the water-absorbing resin composition in accordance with an embodiment of the present invention are preferably present more on and in the vicinities of the surfaces of the water-absorbing resin particles.

The water-absorbing resin composition in which (1) the surfactant and/or the lubricant and/or (2) the chelating agent is/are distributed as described above can be produced by, for example, adding (1) the surfactant and/or the lubricant and/or (2) the chelating agent at a time point after a water-absorbing resin is made particulate. Such a production method allows (1) the surfactant and/or the lubricant and/or (2) the chelating agent to be localized on and in the vicinities of the surfaces of the water-absorbing resin particles.

The water-absorbing resin composition in accordance with an embodiment of the present invention is preferably a particulate water-absorbing resin composition containing polyacrylic acid (salt)-based water-absorbing resin particles in an amount of 60 parts by mass to 100 parts by mass with respect to 100 parts by mass as a total mass of the water-absorbing resin composition. A particle diameter (upper limit and lower limit, average particle diameter, particle size distribution) of the particulate water-absorbing resin composition preferably falls within a range described in (4-4), and is mainly 850 μm to 150 μm.

Examples of a shape of each of particles of the water-absorbing resin and a shape of each of particles of the water-absorbing resin composition include a spherical shape, a substantially spherical shape, a pulverized non-uniform shape (pulverized before or after drying), and a granulated product thereof. Out of the above shapes, the particles of the water-absorbing resin and the particles of the water-absorbing resin composition are each preferably a particle having a pulverized non-uniform shape or a granulated product thereof. Note that Examples (later described) describe water-absorbing resin particles each having a pulverized non-uniform shape and a particulate water-absorbing resin composition having a pulverized non-uniform shape, each of which is obtained by pulverizing a hydrogel that has not been dried and a dried material that has been obtained by drying the hydrogel.

According to the water-absorbing resin composition in accordance with an embodiment of the present invention, a proportion of particles capable of passing through a classification mesh having a mesh size of 150 μm is preferably not more than 5% by mass, more preferably not more than 4% by mass, even more preferably not more than 3% by mass, particularly preferably not more than 2% by mass, most preferably not more than 1% by mass, with respect to the total mass of the water-absorbing resin composition. A lower limit of the proportion is not particularly limited, but is preferably not less than 0.01% by mass.

In a case where the proportion of the particles capable of passing through the classification mesh having a mesh size of 150 μm is not more than 5% by mass, a problem of "gel on skin" is not likely to occur while a consumer uses a disposable diaper. Therefore, the proportion is preferably not more than 5% by mass. Note that the "gel on skin" indicates a state where swollen gel is in direct contact with the skin of a wearer.

A moisture content of the water-absorbing resin composition in accordance with an embodiment of the present invention is not more than 10% by mass, preferably not more than 5% by mass, more preferably not more than 4.5% by mass, even more preferably not more than 4.0% by mass. A lower limit of the moisture content is not particularly limited, but is preferably not less than 1% by mass. That is, the water-absorbing resin composition in accordance with an embodiment of the present invention preferably contains the water-absorbing resin and water as components. By causing the moisture content to be not less than 1% by mass, it is possible to plasticize the water-absorbing resin, and also possible to reduce dust. Meanwhile, in a case where the moisture content is not more than 5% by mass, absorption properties such as an absorbency are not deteriorated. Therefore, the moisture content is preferably not more than 5% by mass.

Note that the moisture content can be measured by a method described in, for example, Examples. Furthermore, the moisture content can be adjusted by the method described in the "(4-3) drying step."

The content of the water-absorbing resin which is contained in the dust of the water-absorbing resin composition in accordance with an embodiment of the present invention is preferably not more than 300 ppm, more preferably not more than 280 ppm, even more preferably not more than 260 ppm, particularly preferably not more than 240 ppm, most preferably not more than 220 ppm, with respect to a total mass of the water-absorbing resin particles. Meanwhile, a lower limit value of the content of the water-absorbing resin which is contained in the dust is not particularly limited, but can be approximately 5 ppm. The content of the water-absorbing resin which is contained in the dust of the water-absorbing resin composition can be measured by a method described in Examples.

In a case where the content of the water-absorbing resin which is contained in the dust falls within the above range, the water-absorbing resin composition has an excellent urine resistance. Therefore, in a case where such a water-absorbing resin composition is used for a sanitary product (such as a disposable diaper), it is possible to suppress stickiness. This mechanism is not clear. However, since a large amount of a chelating agent is taken into dust as has been described, the chelating agent which is distributed on and in the vicinities of surfaces of water-absorbing resin particles that are not the dust is relatively decreased. It is assumed that, as a result, a urine resistance of an entire water-absorbing resin composition is decreased.

In order to suppress the content of the water-absorbing resin which is contained in the dust of the water-absorbing resin composition, it is preferable to take, in a production process, measures of, for example, (1) reducing process damage (for example, using a surfactant and/or a lubricant in a surface-crosslinking step and/or the like), (2) removing fine powder and dust (for example, carrying out a classification step before an additive adding step), and (3) adding a plasticizer such as water or causing a plasticizer such as water to be contained.

A vertical diffusing absorbency under pressure 0.3 psi (VDAUP0.3) of the water-absorbing resin composition in accordance with an embodiment of the present invention is preferably not less than 10 g/g, more preferably not less than 15 g/g, even more preferably not less than 18 g/g, particularly preferably not less than 20 g/g. An upper limit value of the vertical diffusing absorbency under pressure 0.3 psi is not limited in particular, but can be approximately 30 g/g. The vertical diffusing absorbency under pressure 0.3 psi can be measured by a method described in Examples.

By causing the vertical diffusing absorbency under pressure 0.3 psi to fall within the above range, the water-absorbing resin contained in an absorbent body is efficiently used in a case where the water-absorbing resin composition is used for a diaper. This causes a reduction in stickiness of a diaper.

A surface-eluted soluble component of the water-absorbing resin composition in accordance with an embodiment of the present invention is preferably not more than 2.0% by mass, more preferably not more than 1.5% by mass, even more preferably not more than 1.2% by mass, particularly preferably not more than 1.0% by mass. A lower limit value of the surface-eluted soluble component is not limited in particular, but can be approximately 0.1% by mass. The surface-eluted soluble component can be measured by a method described in Examples.

By causing the surface-eluted soluble component to fall within the above range, a soluble component eluted from the surfaces of the water-absorbing resin particles is reduced in a case where the water-absorbing resin composition is used for a diaper. This causes a reduction in stickiness of a diaper.

The water-absorbing resin composition in accordance with an embodiment of the present invention preferably contains a polyvalent metal salt and/or inorganic fine particles. The polyvalent metal salt is generally used as a surface-crosslinking agent or an additive in a process of producing the water-absorbing resin composition. Meanwhile, the inorganic fine particles are generally used as an additive in the process of producing the water-absorbing resin composition. However, applications of the polyvalent metal salt and the inorganic fine particles are not limited to such. Specific examples of the polyvalent metal salt and/or the inorganic fine particles, which is/are preferably contained in the water-absorbing resin composition, include compounds disclosed in, for example, EP1594556A2 and Japanese Patent Application Publication, Tokukai, No. 2015-107488. Furthermore, a preferable amount(s) of the polyvalent metal salt and/or the inorganic fine particles is/are also disclosed in, for example, EP1594556A2 and Japanese Patent Application Publication, Tokukai, No. 2015-107488.

A particle diameter of each of the inorganic fine particles is preferably not more than 500 μm, more preferably not more than 100 μm, most preferably not more than 10 μm, in view of handleability and an effect brought about by addition of the inorganic fine particles. As the polyvalent metal salt, a trivalent or more metal salt can be used, and an aluminum salt is preferable.

The particle diameter can be a particle diameter of a primary particle or can be alternatively a particle diameter of a secondary particle (granulated product, aggregate). In a case where a particle which is so hard as not to be easily broken by an impact force, such as silica or alumina each of which is not an aggregate (primary particle), is used, the particle diameter of the primary particle is preferably not more than 5 μm, more preferably not more than 1 μm, most preferably not more than 0.1 μm. Note that an aggregate or a granulated product (secondary particle) of the primary particle having the above particle diameter can be added.

Specific examples of the inorganic particles contained in the water-absorbing resin composition in accordance with an embodiment of the present invention include: minerals (such as hydrotalcite, calcium phosphate, talc, kaolin, fuller's earth, bentonite, activated clay, barite, natural asphaltum, strontium ore, ilmenite, and pearlite); hydrophilic amorphous silicas (such as ReolosilQS-20 (available from Tokuyama Corporation), which is obtained by a dry method, and Sipernat22S and Sipernat2200 (each available from DEGUSSA), each of which is obtained by a precipitation method); oxide complexes (such as complexes of silicon oxide, aluminum oxide, and magnesium oxide (for example, Attagel #50 available from ENGELHARD), complexes of silicon oxide and aluminum oxide, and complexes of silicon oxide and magnesium oxide); and the like Specific examples of the polyvalent metal salt include: aluminum compounds (such as aluminum sulfate tetradeca-, pentadeca-, hexadeca-, heptadeca-, and octadecahydrates (or anhydrates), aluminum lactate, potassium aluminum sulfate dodecahydrate, aluminum sodium sulfate dodecahydrate, aluminum ammonium sulfate dodecahydrate, aluminum chloride, polyaluminum chloride, and aluminum oxide); and other polyvalent metal salts, polyvalent metal oxides, polyvalent metal hydroxides, and the like.

The inorganic particles and/or the polyvalent metal salt is/are added in an amount falling within a range of preferably 0.001% by mass to 5% by mass, more preferably 0.05% by mass to 3% by mass, even more preferably 0.1% by mass to 1% by mass, with respect to the total mass of the water-absorbing resin composition. In a case where the amount of the inorganic particles and/or the polyvalent metal salt is more than 5% by mass, an absorbency may be decreased. In a case where the amount of the inorganic particles and/or the polyvalent metal salt is less than 0.01% by mass, an effect(s) of adding the inorganic particles and/or the polyvalent metal salt may not be brought about.

In a case where a droplet of a 0.9 mass % aqueous sodium chloride solution is dropped on the water-absorbing resin composition in accordance with an embodiment of the present invention, a contact angle is preferably not more than 90 degrees, more preferably not more than 70 degrees, even more preferably not more than degrees, particularly preferably not more than 30 degrees. Note that a lower limit value of the contact angle in a case where the droplet of the 0.9 mass % aqueous sodium chloride solution is dropped on the water-absorbing resin composition is 0 (zero) degree. The contact angle can be measured by a method described in Examples.

In a case where the contact angle is not more than degrees, the water-absorbing resin composition has high hydrophilicity, and is therefore excellent in diffusion of a liquid in a case where the water-absorbing resin composition is used for an absorbent body. This causes an increase in an area, which absorbs a liquid, of the absorbent body, and causes an improvement in a property of the absorbent body. The contact angle is therefore preferably not more than 90 degrees.

[6] Sanitary Product

The water-absorbing resin composition in accordance with an embodiment of the present invention has both a higher centrifuge retention capacity (CRC) and a more sufficient urine resistance than a conventional one.

Therefore, the water-absorbing resin composition is suitably used for a sanitary product such as a disposable diaper, an incontinence pad, and a medical pad, and particularly suitably used for a disposable diaper.

In a case where the water-absorbing resin composition is used for a sanitary product, the sanitary product preferably includes: a liquid-permeable top sheet to be so positioned as to be adjacent to the body of a wearer; a liquid-impermeable back sheet to be so positioned as to be far from the body of the wearer and adjacent to clothes worn by the wearer; and an absorbent body including the water-absorbing resin composition and positioned between the top sheet and the back sheet. The absorbent body can be provided in two or more layers or can be used in combination with a pulp layer or the like. The absorbent body which includes the water-absorbing resin composition can solely include the water-absorbing resin composition or can include a fibrous material (particularly, pulp) in addition to the water-absorbing resin. The absorbent body includes the water-absorbing resin composition in an amount falling within a range of typically 10% by mass to 100% by mass, preferably 30% by mass to 100% by mass, more preferably 50% by mass to 100% by mass.

Using water-absorbing resin particles having a low centrifuge retention capacity (CRC) is also considered as a method for improving a urine resistance. However, a water-absorbing resin composition which contains the water-absorbing resin particles having a low centrifuge retention capacity (CRC) absorbs a lower amount of a liquid than the water-absorbing resin composition which contains the water-absorbing resin particles having a high low centrifuge retention capacity (CRC), in a case where those water-absorbing resin compositions are identical in amount. Therefore, in a case where the water-absorbing resin composition which contains the water-absorbing resin particles having a low centrifuge retention capacity (CRC) is used as a member of the absorbent body, the absorbent body absorbs an insufficient amount of a liquid. This ultimately causes stickiness. The amount of the liquid absorbed by the absorbent body can be increased by increasing an amount of the water-absorbing resin composition to be used. However, this method leads to an increase in a cost.

[Arrangements of the Present Invention]

The present invention can be arranged as follows.

An aspect of the present invention is a water-absorbing resin composition having the following properties:

(1) A centrifuge retention capacity (CRC) being not less than 35 g/g;

(2) A post-degradation-test one-hour eluted soluble component being not more than 19% by mass;

(3) An absorbency against pressure 0.7 psi (AAP0.7) being not less than 10 g/g; and (4) A content of a water-absorbing resin in dust being not more than 300 ppm with respect to a total mass of the water-absorbing resin composition.

The water-absorbing resin composition is preferably arranged so as to further include: a chelating agent in an amount of not less than 1 ppm and not more than 1.0% by mass with respect to 100 parts by mass of the water-absorbing resin composition.

The water-absorbing resin composition is preferably arranged so as to further include: a surfactant and/or a lubricant.

The water-absorbing resin composition is preferably arranged such that the water-absorbing resin composition has a surface tension of not less than 65 mN/m.

The water-absorbing resin composition is preferably arranged such that the water-absorbing resin composition has a moisture content of not more than 5% by mass.

The water-absorbing resin composition is preferably arranged so as to further include: a polyvalent metal salt and/or an inorganic fine particle.

The water-absorbing resin composition is preferably arranged such that the water-absorbing resin composition has a vertical diffusing absorbency under pressure 0.3 psi (VDAUP0.3) of not less than 10 g/g.

The water-absorbing resin composition is preferably arranged such that the water-absorbing resin composition includes a surface-eluted soluble component of not more than 2.0% by mass.

The water-absorbing resin composition is preferably arranged such that a proportion of a particle capable of passing through a classification mesh having a mesh size of 150 μm is not more than 5% by mass with respect to the total mass of the water-absorbing resin composition.

The water-absorbing resin composition is preferably arranged such that in a case where a droplet of a 0.9 mass % aqueous sodium chloride solution has been dropped on the water-absorbing resin composition, a contact angle is not more than 90 degrees.

The water-absorbing resin composition is preferably arranged such that the water-absorbing resin composition is a particulate water-absorbing resin composition including a polyacrylic acid (salt)-based water-absorbing resin particle in an amount within a range of 60 parts by mass to 100 parts by mass with respect to 100 parts by mass as the total mass of the water-absorbing resin composition.

Another aspect of the present invention is a sanitary product, including: a water-absorbing resin composition as described above.

The present invention can be also arranged as follows.

An aspect of the present invention is a method for producing a water-absorbing resin composition having a centrifuge retention capacity (CRC) of not less than 35 g/g, the method including: using a water-absorbing resin particle; and adding a surfactant and/or a lubricant and a chelating agent to the water-absorbing resin particle.

Another aspect of the present invention is a method for producing a water-absorbing resin composition having a centrifuge retention capacity (CRC) of not less than 35 g/g, the method including: a surface-crosslinking step; a step of adding a surfactant and/or a lubricant to a water-absorbing resin particle; and a step of adding a chelating agent to the water-absorbing resin particle, the surfactant and/or the lubricant being added to the water-absorbing resin particle between a first time point, at which at least part of a crosslinked hydrogel polymer obtained by polymerizing a unsaturated monomer under the presence of an internal crosslinking agent, is made particulate, and a second time point, at which the surface-crosslinking ends.

The above production method is preferably arranged such that, after the surfactant and/or the lubricant is added, the chelating agent is added.

The production method is preferably arranged so as to further include a classification step, the surface-crosslinking step being carried out after the classification step, and the surfactant and/or the lubricant being added to the water-absorbing resin particle between a third time point, at which the classification step ends, and the second time point, at which the surface-crosslinking step ends.

The production method is preferably arranged such that the surface-crosslinking step is carried out with use of a continuous type paddle mixer.

The production method is preferably arranged so as to further include a second classification step after the surface-crosslinking step, in the second classification step, at least part of a particle capable of passing through a classification mesh having a mesh size of 150 μm being removed.

The production method is preferably arranged such that the surfactant and/or the lubricant is/are used in an amount of 0.0001 parts by mass to 0.05 parts by mass with respect to 100 parts by mass of the water-absorbing resin composition.

The production method is preferably arranged such that the chelating agent is used in an amount of 0.0001 parts by mass to 1.0 part by mass with respect to 100 parts by mass of the water-absorbing resin composition.

The production method is preferably arranged such that an aqueous solution of the surfactant, the lubricant, and/or the chelating agent is added to the water-absorbing resin particle.

The production method is preferably arranged so as to further include an air transport step in a production process.

An another aspect of the present invention is a water-absorbing resin composition having a centrifuge retention capacity (CRC) of not less than 35 g/g, the water-absorbing resin composition including: a water-absorbing resin particle, a surfactant and/or a lubricant, and a chelating agent, the water-absorbing resin composition including the chelating agent in an amount of not more than 1.0% by mass with respect to a total mass of the water-absorbing resin composition, the water-absorbing resin composition including a degradable soluble component at a proportion of not more than 19%.

The water-absorbing resin composition is preferably arranged such that an absorbency against pressure 0.7 psi (AAP0.7) is not less than 15 g/g.

The water-absorbing resin composition is preferably arranged such that the water-absorbing resin composition has a surface tension of not less than 65 mN/m.

The water-absorbing resin composition is preferably arranged such that the surfactant has HLB of 8 to 18.

The water-absorbing resin composition is preferably arranged such that the water-absorbing resin composition includes the surfactant in an amount of not more than 100 ppm with respect to the total mass of the water-absorbing resin composition.

The water-absorbing resin composition is preferably arranged such that the water-absorbing resin composition includes the chelating agent in an amount of 80 ppm to 3000 ppm with respect to the total mass of the water-absorbing resin composition.

The water-absorbing resin composition is preferably arranged such that the water-absorbing resin composition satisfies the following conditions (1) and (2):
(1) the surfactant and/or the lubricant included in the water-absorbing resin composition is/are present more on and in the vicinity of a surface of the water-absorbing resin particle than inside the water-absorbing resin particle.
(2) the chelating agent included in the water-absorbing resin composition is present more on and in the vicinity of the surface of the water-absorbing resin particle than inside the water-absorbing resin particle.

The water-absorbing resin composition is preferably arranged such that a proportion of a particle capable of passing through a classification mesh having a mesh size of 150 μm is not more than 5% by mass with respect to the total mass of the water-absorbing resin composition.

The water-absorbing resin composition is preferably arranged such that the water-absorbing resin composition has a moisture content of not more than 5% by mass.

Still another aspect of the present invention is a sanitary product including a water-absorbing resin composition as described above.

The present invention is not limited to the embodiments, but can be altered by a skilled person in the art within the scope of the claims. The present invention also encompasses, in its technical scope, any embodiment derived by combining technical means disclosed in differing embodiments.

EXAMPLES

The following description will discuss an embodiment of the present invention with reference to Examples. It should be noted that the present invention is not limited in construction to Examples. Unless otherwise stated, properties specified in the present specification or Examples were obtained by EDANA methods and other measurement methods below under a condition that a temperature was a room temperature (20° C. to 25° C.) and a humidity was 50% RH. For electric devices used in Examples and Comparative Examples, power sources of 200 V or 100 V and 60 Hz were used. For convenience, "liter" will be referred to as L.

[Method for Measuring Properties]

(1) Centrifuge Retention Capacity (CRC)

In the present specification, a centrifuge retention capacity (CRC) was measured in conformity with an EDANA method (ERT 441.2-02).

(2) Absorbency Against Pressure 0.3 Psi (AAP0.3)

In the present specification, an absorbency against pressure 0.3 psi (AAP0.3) was measured in conformity with an EDANA method (ERT 442.2-02). Note that measurement was carried out under a load of 2.03 kPa (0.3 psi).

(3) Absorbency Against Pressure 0.7 Psi (AAP0.7)

An absorbency against pressure 0.7 psi (AAP0.7) (g/g) was measured by a method similar to the above-described method for measuring the above-described absorbency against pressure 0.3 psi (AAP0.3), except that a load applied to a water-absorbing resin composition was set to 4.83 kPa.

(4) Vertical Diffusing Absorbency Under Pressure 0.3 Psi (VDAUP0.3)

A vertical diffusing absorbency under pressure 0.3 psi (VDAUP0.3) (g/g) was determined by a method similar to the above-described method for measuring an absorbency against pressure 0.3 psi (see the item (2) in this section), except that a weight of a water-absorbing resin was changed to 5.000 g.

(5) Eluted Soluble Component

In the present specification, an eluted soluble component was measured in conformity with an EDANA method (ERT 470.2-02).

More specifically, 184.3 g of a 0.90 mass % aqueous sodium chloride solution (saline) was weighed and introduced into a 250 mL plastic container (diameter: 6 cm, height: 9 cm) having a lid, and 1.00 g of a water-absorbing resin composition was added to the 0.90 mass % aqueous sodium chloride solution. The saline in the container was stirred for 16 hours at a rotation speed of 500 rpm with use of a magnetic stirring bar having a diameter of 8 mm and a length of 25 mm, so that an eluted soluble component in the water-absorbing resin composition was extracted. An extract thus obtained was filtered with use of one sheet of filter paper (Advantec Toyo Kaisha, Ltd., Product name: JIS P 3801, No. 2, thickness: 0.26 mm, retaining particle diameter: 5 μm), and 50.0 g of a filtrate thus obtained was weighed and used as a solution for measurement.

First, a saline to which no water-absorbing resin composition was added was titrated with a 0.1N aqueous sodium hydroxide to reach pH10, further titrated with 1N hydrochloric acid to reach pH2.7. Control titers (referred to as [bNaOH] and [bHCl], respectively) were obtained.

A similar titration operation was also conducted with respect to the solution for measurement, and titers (referred to as [NaOH] and [HCl], respectively) were obtained.

In a case of a water-absorbing resin composition including a known amount of acrylic acid and sodium salt thereof, an eluted soluble component in the water-absorbing resin composition was calculated in accordance with the following equation on the basis of an average molecular weight of monomers of the water-absorbing resin composition and titers obtained by the above operation. In a case of a water-absorbing resin composition including an unknown amount of acrylic acid and sodium salt thereof, an average molecular weight of monomers was calculated with use of a neutralization rate which was determined by making calculation in accordance with the results of the above titration and the following equation, and then an eluted soluble component (% by mass) was calculated.

$$\text{Eluted soluble component (\% by mass)} = 0.1 \times (\text{average molecular weight of monomers}) \times 184.3 \times 100 \times ([HCl] - [bHCl])/(1000 \times 1.0 \times 50.0)$$

$$\text{Neutralization rate(mol \%)} = [1 - ([NaOH] - [bNaOH])/([HCl] - [bHCl])] \times 100$$

(6) Surface-Eluted Soluble Component

Into a 250 mL plastic container (diameter: 6 cm, height: 9 cm) having a lid, 20 g of a 0.90 mass % aqueous sodium chloride solution (physiological saline) and 1.00 g of a water-absorbing resin composition were introduced and then allowed to stand still for 1 hour. Thereafter, 180 g of a 0.90 mass % saline was further added, and stirring was carried out for 1 minute (at 500 rpm, with use of a magnetic stirrer measuring 8 mm in diameter and 25 mm in length). In this way the surface-eluted soluble component was extracted from the water-absorbing resin composition.

Promptly after the 1 minute of stirring was finished, the extract was filtered with use of one sheet of filter paper (Advantec Toyo Kaisha, Ltd., product name: JIS P 3801, No. 2, thickness: 0.26 mm, retains particle diameter of 5 μm). 50.0 g of the obtained filtrate was used as a liquid for measurement.

Titration was carried out in a manner similar to that in the measurement of eluted soluble component (see item "(5)" of the present section), and the soluble component eluted from the vicinity of the surface of particles of the water-absorbing resin composition (surface-eluted soluble component, % by mass) was calculated.

(7) Post-Degradation-Test One-Hour Eluted Soluble Component

As used in the present specification, the term "post-degradation-test one-hour eluted soluble component" refers to a water-soluble component measured in a manner such that, in a measurement method defined by an EDANA method (ERT470.2-02), a 0.90 mass % aqueous sodium chloride solution is changed to an aqueous solution (degradation test liquid) obtained by mixing L-ascorbic acid with a 0.90 mass % aqueous sodium chloride solution, wherein the water-soluble component is that observed after the water-absorbing resin composition is allowed to stand still in the degradation test liquid for 2 hours at 60° C. and then stirred for 1 hour.

200.0 g of an aqueous solution containing 0.05% by mass of L-ascorbic acid and 0.90% by mass of sodium chloride (i.e., a degradation test liquid which was a mixture of 0.10 g of L-ascorbic acid and 199.90 g of 0.90 mass % aqueous sodium chloride solution) was introduced into a 250 mL plastic container (having an inner lid and outer lid) into which a rotor (length: 35 mm) had been placed. 1.00 g of water-absorbing resin composition was added to the aqueous solution, and the plastic container was then sealed with use of the inner and outer lids. The plastic container was left to stand still for 2 hours in an incubator set to 60° C.±2° C. After the 2 hours had passed, the plastic container was removed from the incubator, and stirring was carried out for 1 hour at room temperature with use of a stirrer (rotation speed: approximately 500 rpm). Through these operations, the water-soluble component of the particulate water-absorbing resin composition was extracted.

After the stirring, the extract (which is the aqueous solution) was filtered with the use of one sheet of filter paper (Advantec Toyo Kaisha, Ltd., Product name: JIS P 3801, No. 2, thickness 0.26 mm, retains particle diameter of 5 μm), and 50.0 g of the obtained filtrate was weighed and used as a solution for measurement. Next, the solution for measurement was titrated with a 0.1N—NaOH aqueous solution until a pH of 10 was attained, and then titrated with a 0.1N—HCl aqueous solution until a pH of 2.7 attained. The amounts of the aqueous solutions ([NaOH] mL, [HCl] mL) used in the titration operations were determined.

Furthermore, the same operation was performed on 200.0 g of a degradation test liquid alone, without addition of the water-absorbing resin composition. The amounts of the aqueous solutions ([b2NaOH] mL, [b2HCl] mL) used in the blank titration operations were determined.

The amount of the aqueous solutions used in titration and the monomer average molecular weight of the water-absorbing resin were used in the following formula to calculate the post-degradation-test one-hour eluted soluble component.

Post-degradation-test one-hour eluted soluble component [% by mass]=0.1×monomer average molecular weight×200×100×([HCl]−[b2HCl])/(1000×1.0×50.0)

In cases where the monomer average molecular weight was unknown, the monomer average molecular weight was calculated with use of the neutralization rate calculated in item "(5)" above.

(8) Moisture Content 1.00 g of water-absorbing resin was spread uniformly in an aluminum cup (height: 2 cm, diameter of bottom surface: 4 cm) on the bottom surface thereof, and a combined mass W1 (g) of the aluminum cup and the water-absorbing resin therein was measured. The aluminum cup containing the water-absorbing resin therein was placed for 3 hours into a dryer (EYELA, manufactured by Tokyo Rikakikai Co., Ltd., fixed temperature incubator/dryer (natural oven) NDO-450) which had been set to 180° C. Thereafter, the aluminum cup containing the water-absorbing resin was removed from the hot air dryer, and the combined mass W2 (g) of the aluminum cup and the water-absorbing resin therein was measured immediately after removal (at least within 1 minute of removal). The values of W1 and W2 were used in the following formula to calculate moisture content (% by mass).

moisture content (% by mass)=[($W1$(g)−$W2$(g))/(mass(g)of water-absorbing resin)]×100

(9) Particle Size Distribution (Mass Average Particle Diameter (D50), and Logarithmic Standard Deviation (σξ) of Particle Size Distribution)

10.0 g of water-absorbing resin was placed in a set of JIS standard sieves (THE IIDA TESTING SIEVE, diameter: 8 cm) having respective mesh sizes of 850 μm, 500 μm, 300 μm, and 150 μm. A vibration classifier (IIDA SIEVE SHAKER, Type: ES-65, Ser. No.: 0501) was then used to carry out classification for 5 minutes, and a percent R of the water-absorbing resin remaining on each sieve was plotted on logarithmic probability paper. From the results of classification, a particle diameter for which R=50% by mass was considered to be the weight average particle diameter (D50).

Furthermore, in a case where a particle diameter for which R=84.1% by mass is represented as X1, and a particle diameter for which R=15.9% by mass is represented as X2, the logarithmic standard deviation (σξ) is represented by the formula below. In the formula below, a smaller σξ value means a narrower particle size distribution.

σξ=0.5×ln($X2/X1$).

Note that the water-absorbing resin used in the measurement had been dried for 24 hours at 60±5° C. under reduced pressure (less than 1 mmHg (133.3 Pa)) prior to measurement.

(10) Surface Tension 50 ml of physiological saline having a temperature adjusted to be 23° C. to 25° C. was put into a sufficiently washed 100-ml beaker. Then, the surface tension of the physiological saline was measured with the use of a surface tension meter (K11 automatic surface tension meter, manufactured by KR USS). Because this measurement was made in order to determine a standard, the measured value of the surface tension needs to be in a range of 71 mN/m to 75 mN/m.

Next, a fluorocarbon resin rotor (length: 25 mm) that had been sufficiently washed and 0.5 g of a water-absorbing resin composition were put into the beaker containing the physiological saline, whose temperature had been adjusted to be 23° C. to 25° C. and surface tension had been measured, and then stirring was performed at 500 rpm for 4 minutes. After the 4 minutes, the stirring was stopped, and then, after the water-absorbing resin composition which had absorbed water precipitated, the surface tension of the supernatant liquid was measured. For the present measurement, a plate method using a platinum plate was employed. Before being used in each of the measurements, the plate was sufficiently washed, and also washed while being heated with use of a gas burner.

(11) Acid Value of Surfactant

Acid values of surfactants were measured in conformity with a neutralization titration method defined in JIS K 0070 (1992).

(12) Content of Water-Absorbing Resin in Dust

Content of water-absorbing resin in dust (content of water-absorbing resin in dust occurring from 100 parts by mass of water-absorbing resin composition) was determined through the following procedure:

Step 1: Measure amount of dust.

Step 2: Determine proportions (% by mass) of water-absorbing resin, $SiO_2$, and aluminum sulfate contained in dust. In a case where $SiO_2$ and/or aluminum sulfate is/are not contained in the dust, the proportion thereof is considered to be 0% by mass.

Step 3: Calculate content of the water-absorbing resin in the dust.

<Measurement of Amount of Dust>

An increase in mass due to dust attracted/caught by glass fiber filter paper over a predetermined period of time was measured in accordance with the conditions described below. This measured value was considered to be the amount of dust occurring from the water-absorbing resin composition. The measuring apparatus used was Heubach DUSTMETER (manufactured by Heubach Engineering GmbH (German)), and a measurement mode Type I was used. The measurement was carried out in an atmosphere at a temperature of 25° C. (±2° C.), at a relative humidity of 20% to 40%. The measurement was carried out under a normal pressure.

Specifics of the measurement method are as follows.

1. The water-absorbing resin composition (100.00 g) was placed as a measurement sample into a rotatable drum of the DUSTMETER.

2. A mass ([Da] g) of the glass fiber paper filter was measured to 0.00001 g accuracy. The glass fiber filter paper retains a particle diameter of 0.5 μm (can be determined in accordance with precipitation retaining properties defined in JIS P3801) and has a diameter of 50 mm. For example, the glass fiber filter paper may be the product GLASS FIBER, GC-90 (manufactured by ADVANTEC), or an equivalent product, the product being processed so as to have a diameter of 50 mm.

3. A coarse particle separator was fixed to the rotatable drum, and a filter case to which the glass fiber filter paper was mounted was fixed to coarse particle separator.

4. The DUSTMETER was set to the following measurement conditions, and then measurement was carried out. Rotation speed of the drum: 30 R/min; suction air volume: 20 L/min; time (measurement time): 30 minutes.

5. After the 30 minutes elapsed, a mass ([Db] g) of the glass fiber filter paper was measured to 0.00001 g accuracy.

The amount of dust was calculated from the formula below, using [Da] and [Db]. Calculated from the formula below is the amount [ppm] of dust with respect to the total mass of the water-absorbing resin composition.

$$\text{Amount of dust[ppm]}=\{([Db]-[Da])/100.00\}\times 1000000$$

<Determining Proportions (% by Mass) of Water-Absorbing Resin, $SiO_2$, and Aluminum Sulfate in Dust>

The proportions (% by mass) of water-absorbing resin, $SiO_2$, and aluminum sulfate in the dust (collected in the above-described dust amount measurement) were determined.

In order to determine these proportions, the proportions of elemental Na, elemental Si, and elemental Al contained in the dust were analyzed. Then, the mass ratio of the water-absorbing resin, the $SiO_2$, and the aluminum sulfate were calculated from results of the analysis, in accordance with the neutralization rate and the weight average molecular weight of the water-absorbing resin (including sodium salt as a neutralized salt).

Note that even in a case where the neutralized salt of the water-absorbing resin is not sodium salt but some other salt such as potassium salt, lithium salt, or ammonium salt, it is possible to find the proportions of water-absorbing resin, $SiO_2$, and aluminum sulfate in the dust in a manner similar to the above-described method. For example, in a case where the neutralized salt of the water-absorbing resin is potassium salt, analysis can be performed to determine proportions of elemental K, elemental Si, and elemental Al.

Quantitative analysis of the elemental Na, elemental Si, and elemental Al contained in the dust was carried out via a ZAF method with use of an SEM/EDS (Energy Dispersive X-ray Spectrometer).

An appropriate amount of dust was collected from the glass fiber filter paper used in the above-described dust amount measurement and then subjected to quantitative analysis. The dust was transferred to a stage for SEM, on which was affixed carbon tape measuring 5 mm×5 mm. At this time, the dust was dispersed uniformly on the carbon tape.

The example discussed here is a method of quantifying $SiO_2$ and aluminum sulfate. Note, however, that in a case where a substance containing element(s) other than elemental Si and elemental Al exists in the dust, quantitative analysis can be performed for the element(s) contained in that substance. Furthermore, even in a case where a substance, such as moisture, which does not contain a metallic element exists in the dust, that substance can be subjected to quantitative analysis as necessary with use of known techniques.

Measurement conditions used during the quantitative analysis are as follows.
  Device: Scanning electron microscope (JSM-5410LV SCANNING MICROSCOPE, manufactured by JOEL)
  Acceleration voltage: 20 kV
  Magnification: 20 times
  Measurement field of view: Approximately 900 μm×1200 μm (measurement carried out in state where at least 50% by area of the entire area of the measurement field of view was covered by dust)
  Si peak: SiKα 1.739 KeV
  Na peak: NaKα 1.041 KeV
  Al peak: AlKα 1.486 KeV Note that in cases where the above-described peaks of elements of interest coincided with the peak of some other element (for example, NaKα vs ZnLα), measured values were calibrated by subtracting the value of the peak derived from the other element (ZnKα in the case of Zn).

By using the % by mass of the elemental Na (hereinafter abbreviated as "Na %"), the % by mass of the elemental Al (hereinafter abbreviated as "Al %"), the % by mass of the elemental Si (hereinafter abbreviated as "Si %"), the neutralization rate N (mol %) (described below) of the water-absorbing resin, and the polymer unit weight average molecular weight Mw (described below) of the water-absorbing resin, the proportions (% by mass) of the water-absorbing resin, the $SiO_2$, and the aluminum sulfate contained in the dust can be calculated from the formulas below.

Polymer unit weight average molecular weight $Mw=72.06\times(1-N/100)+94.05\times N/100$
  Water-absorbing resin component amount $P=\{(Na\%/23)/(N/100)\}\times Mw$
  $SiO_2$ component amount $S=(Si\%/28.08)\times 60.08$
  Aluminum sulfate component amount $A=(Al\%/26.98)\times 630.4/2$
  Proportion (% by mass) of water-absorbing resin in dust$=\{P/(P+S+A)\}\times 100$
  proportion (% by mass) of $SiO_2$ in dust$=\{S/(P+S+A)\}\times 100$
  Proportion (% by mass) of aluminum sulfate in dust$=\{A/(P+S+A)\}\times 100$ The neutralization rate N of the water-absorbing resin as used in the above formulas can be measured via the above-described method of measuring the eluted soluble component amount (see item "(5)" of the present section).

The proportions of the water-absorbing resin, the $SiO_2$, and the aluminum sulfate in the dust are preferably measured by the above-described method. However, in a case where, for example, the components are unknown or there are a large number of other elements existing in the dust, a conventionally known method (elemental analysis or the like) can be used to carry out measurement.

<Measurement of Content of Water-Absorbing Resin in Dust>

The content of the water-absorbing resin in the dust can be calculated via the formula below, using the amount of dust (collected in the above-described dust amount measurement) and the measured proportions of the water-absorbing resin, the $SiO_2$, and the aluminum sulfate. The value of the amount of dust as used in the formula below is a value with respect to the total mass of the water-absorbing resin composition, as described earlier. As such, in the formula below, the value of the content of the water-absorbing resin in the dust is also a value with respect to the total mass of the water-absorbing resin composition.

Content of water-absorbing resin in dust[ppm]= amount of dust[ppm]×$P/(P+S+A)$.

(13) FGBP (Free Swell GBP)

FGBP was measured basically in conformance with a gel bed permeability test using the "free swell" conditions as disclosed in International Publication No. 2004/096304. However, while a water-absorbing resin composition falling in the range of 300 μm to 600 μm was selected and subjected to measurement in International Publication No. 2004/096304, in the present examples, selection of the water-absorbing resin composition based on particle size was not carried out. Rather, the water-absorbing resin compositions themselves, as obtained in the examples, were subjected to measurement.

(14) Moisture Absorption Blocking Rate

Approximately 2 g of water-absorbing resin composition was dispersed uniformly in an aluminum cup having a diameter of 52 mm. The aluminum cup containing the water-absorbing resin composition was then placed for 30 minutes in a thermo-hygrostat (ESPEC CORP.; MODEL: SH-641) set to a temperature of 25° C. and a relative humidity of 80±5% RH.

Thereafter, the water-absorbing resin composition in the aluminum cup was gently transferred onto a JIS standard sieve (The IIDA TESTING SIEVE/inner diameter: 80 mm) having a mesh size of 2000 μm (8.6 mesh). A low-tap type sieve shaker (product name:"ES-65 sieve shaker", manufactured by Sieve Factory Iida Co., Ltd., rotation speed: 230 rpm, number of impacts: 130 rpm) was used to carry out classification for 5 seconds at a temperature of 20° C. to 25° C. and a relative humidity of 50% RH.

A mass (mass W3 [g]) of the water-absorbing resin composition remaining on the JIS standard sieve, and a mass (mass W4 [g]) of the water-absorbing resin composition which passed through the JIS standard sieve were measured, and then fluidity during moisture absorption (moisture absorption blocking rate) was calculated using the formula below. A lower value of the moisture absorption blocking rate corresponds to a more favorable fluidity during moisture absorption.

$$\text{Moisture absorption blocking rate[\% by mass]} = \{W3/(W3+W4)\} \times 100$$

(15) Contact Angle

Double-sided adhesive tape was affixed to a stainless steel plate, and water-absorbing resin composition was dispersed onto the double-sided adhesive tape. Thereafter, water-absorbing resin composition which did not adhere to the double-sided tape was scraped off. In this way, a sample plate whose surface was covered with the water-absorbing resin composition was prepared.

Measurements were made to determine the contact angle produced when a 0.90 mass % physiological saline was brought into contact with the sample plate. The measurement was carried out via a drop method using a contact angle meter (model: FACE CA-X, manufactured by Kyowa Interface Science Co., LTD), at 20° C. and 60% RH. More specifically, measurement was carried out to determine the contact angle as observed 1 second after a droplet of the 0.90 mass % physiological saline was dropped onto the sample plate. For each sample, this measurement was carried out five times, and the average of the five measurements was considered to be the contact angle of the water-absorbing resin composition.

(16) Evaluation of Performance of Absorbent Body

In order to evaluate the performance of an absorbent article in which the water-absorbing resin (or water-absorbing resin composition) is used in an absorbent body, absorbent articles were produced and subjected to a feel test, measurement of liquid absorbing time, and measurement of re-wet.

(Production of Absorbent Article)

First, 50 parts by mass of the water-absorbing resin composition and 50 parts by mass of wood-ground pulp were dry-mixed with use of a mixer. Then, on a 400-mesh wire screen (mesh size of 38 μm), the resulting mixture was formed into a web (absorbent body having water-absorbing resin concentration of 50%) measuring 120 mm×400 mm, via air-laid paper making carried out with use of a batch-type air-laid paper making device. Next, the web was pressed for 5 seconds at a pressure of 196.14 kPa so as to obtain an absorbent body in which a basis weight of the water-absorbing resin composition was approximately 0.047 [g/cm$^2$].

Next, a liquid impermeable back sheet (liquid impermeable sheet) made of polypropylene and having a so-called leg gather, the absorbent body, and a liquid permeable top sheet (liquid permeable sheet) made of polypropylene were adhered to each other in this order with use of double-sided tape. Thereafter, a so-called tape fastener was fixed to these members adhered to each other, and thus an absorbent article (i.e., a disposable diaper) was produced. The absorbent article had a mass of 46 g.

(Feel Test Method)

The absorbent article produced as above was spread out on a flat surface so that the liquid permeable top sheet faced upward. A resin cylinder (inner diameter: 70 mm, inner volume: 346 cm$^3$) was then placed in a center part of the absorbent article. Thereafter, 300 mL of the degradation test liquid described in item "(5)" above was poured into the cylinder in a manner so as not to overflow. After all of the liquid was absorbed by the absorbent article, the absorbent article having the liquid absorbed therein was placed into a polypropylene bag (re-sealable plastic bag with zipper, Uni-Pack 1-4, manufactured by SEISANNIPPONSHA Ltd.), and the bag was sealed with the zipper after air in the bag was removed as much as possible.

Thereafter, the bag sealed thusly was allowed to stand still for 2 hours in an incubator set to 60±2° C. After the 2 hours, the absorbent article was removed from the bag, the top sheet (into which the liquid had been poured) was touched, and stickiness was evaluated based on the following five-point scale. Evaluation was carried out by at least five evaluators, and the average value was used as the evaluation score.

<Stickiness>

5: Very sticky; 4: sticky; 3: slightly sticky; 2: almost no stickiness; 1: no stickiness.

(Liquid Absorbing Time)

An acrylic plate (size: 120 mm×400 mm) having a liquid inlet (diameter: 70 mm) was placed on the top sheet (liquid permeable sheet) of the absorbent article produced as above, so that the liquid inlet was positioned in a center part of the top sheet. A weight was then placed on the acrylic plate. The weight was prepared in a manner such that a load of 2.1 kPa would be applied evenly across the entire area of contact between the acrylic plate and the top sheet.

Next, 75 mL of physiological saline (0.9 wt % aqueous sodium chloride solution) was poured into the liquid inlet 5 times (total poured amount: 375 mL), with an interval of 30 minutes between each pouring. The time taken for the absorbent article to absorb the physiological saline of the fifth pouring (i.e., the amount of time measured from the fifth pouring of the physiological saline to when the physiological saline above the liquid permeable sheet was taken into the absorbent article) was recorded as the "liquid absorbing time".

(Method for Evaluating Re-Wet)

30 minutes after measuring the liquid absorbing time as described above, the weight and the acrylic plate were removed, and 30 paper towels (size: 120 mm×400 mm; manufactured by Oji Nepia Co., Ltd.) were placed onto the absorbent article. A total mass (W1 [g]) of the 30 paper towels had been measured prior to their placement. A weight (total mass: 10 kg) was quickly placed on the paper towels.

After 1 minute, the mass (W2 [g]) of the 30 paper towels was measured, and the re-wet of the absorbent article was calculated using the formula below.

$$\text{Re-wet[g]}=W2-W1$$

Production Example 1

Into a reactor formed by attaching a lid to a stainless steel twin-arm kneader (capacity: 10 L) having two sigma-type blades and a jacket, 382.5 g of acrylic acid, 4047.4 g of a 37 mass % aqueous sodium hydroxide solution, 544.8 g of deionized water, and 1.96 g of polyethylene glycol diacrylate (molecular weight: 523) (0.019 mol % with respect to unsaturated monomer(s) having a carboxyl group) were fed and dissolved to obtain an aqueous monomer solution (a1). The aqueous monomer solution (a1) was degassed in a nitrogen atmosphere for 20 minutes. Next, while the aqueous monomer solution (a1) was stirred, 12.74 g of a 10 mass % aqueous sodium persulfate solution and 10.62 g of a 0.1 mass % aqueous L-ascorbic acid solution were added thereto. Polymerization commenced approximately 1 minute thereafter. Then, polymerization was carried out at 20° C. to 95° C. while crushing a gel that was created. 30 minutes after polymerization had started, a hydrogel (1) was obtained and taken out. The hydrogel (1) obtained thusly had been grain refined such that its particles were not more than approximately 5 mm in size.

The grain-refined hydrogel (1) was spread out on a metal gauze (50 mesh) and dried with hot air at 180° C. for 50 minutes. A resulting dried material was pulverized with use of a roll mill and then classified with use of a JIS standard sieve having a mesh size of 850 μm and a JIS standard sieve having a mesh size of 150 μm. This produced water-absorbing resin particles (A1) having a non-uniformly pulverized shape, the particles having a particle diameter of 850 μm to 150 μm. The water-absorbing resin particles (A1) had a centrifuge retention capacity (CRC) of 51.2 g/g and an eluted soluble component amount of 25.9% by mass.

Production Example 2

441.0 g of acrylic acid, 0.768 g of polyethylene glycol diacrylate (molecular weight: 523) as an internal crosslinking agent (0.024 mol % with respect to unsaturated monomer(s) having a carboxyl group), 2.70 g of a 1.0 mass % aqueous diethylenetriamine pentaacetic acid trisodium (DTPA.3Na) solution, 181.69 g of a 48.5 mass % aqueous sodium hydroxide solution, and 366.44 g of deionized water (ion-exchange water) were introduced into a 2-liter polypropylene container, and were mixed with one another so as to prepare an aqueous monomer solution (a2').

Next, the aqueous monomer solution (a2') was cooled while being stirred. At a time point at which the liquid temperature reached 39.5° C., 189.76 g of a 48.5 mass % aqueous sodium hydroxide solution having a temperature adjusted to 40° C. was added to the aqueous monomer solution (a2'), and was mixed therewith so as to prepare an aqueous monomer solution (a2). At this time, the temperature of the aqueous monomer solution (a2) rose to 79.8° C. immediately after the preparation due to heat of neutralization at a second stage.

Next, 17.68 g of a 4.5 mass % aqueous sodium persulfate solution was added to the aqueous monomer solution (a2) while stirring was carried out. Immediately after that, the resulting solution was poured in an atmospheric air open system into a stainless steel vat-type vessel (with a bottom surface of 340 mm×340 mm and a height of 25 mm; inner surface: Teflon (registered trademark) coating). Pouring of the aqueous monomer solution (a2) into the vat-type vessel commenced 55 seconds after the start of the second-stage neutralization. The vat-type vessel was heated with use of a hot plate (NEO HOTPLATE HI-1000; Iuchi Seiei Do Ltd.) until surface temperature reached 40° C.

Then, 58 seconds after the aqueous monomer solution (a2) was poured into the vat-type vessel, a polymerization reaction started. In this polymerization reaction, a polymer that was generated gave off water vapor and swelled and foamed in various directions. The polymer then shrunk to a size slightly larger than the size of the vat-type vessel. Then, 3 minutes after the start of the polymerization reaction, a hydrogel polymer (2) was obtained and taken out. Note that this series of operations was carried out in an atmospheric air open system.

The hydrogel (2) prepared through the above polymerization reaction was subjected to gel-crushing with use of a meat chopper (HL-3225N; plate pore diameter: 10.0 mm; Remacom Co., Ltd.), so as to obtain a particulate hydrogel (2).

The hydrogel (2) was introduced into the meat chopper at a rate of 230 g/min. The gel-crushing was carried out while deionized water having a temperature adjusted to 90° C. was being added at a rate of 50 g/min simultaneously with the introduction of the hydrogel (2).

The particulate hydrogel (2) prepared through the above operation was spread on a stainless-steel metal gauze having a mesh size of 850 μm, and was dried by letting through 180° C. hot air for 30 minutes. Subsequently, a dry polymer (2) obtained through the drying treatment was pulverized with use of a roll mill (WML-type roll crusher; Inoguchi Giken Ltd.), and was then classified with use of JIS standard sieves having respective mesh sizes of 710 μm and 45 μm. This produced water-absorbing resin particles (A2) having a non-uniformly pulverized shape, the particles having a particle diameter of 710 μm to 45 μm. The water-absorbing resin particles (A2) had a centrifuge retention capacity (CRC) of 48.3 g/g and an eluted soluble component amount of 24.6% by mass.

Example 1

With 100 parts by mass of the water-absorbing resin particles (A1) having a non-uniform particle shape as obtained in Production Example 1 (particle diameter: 850 μm to 150 μm), a surface-treating agent solution was mixed uniformly, the surface-treating agent solution being obtained by mixing 0.385 parts by mass of ethylene carbonate, 0.644 parts by mass of propylene glycol, 2.6 parts by mass of deionized water, and 0.01 parts by mass of a polyoxyethylene (20) sorbitan monostearate solution having a concentration of 10% by mass (0.001 parts by mass of polyoxyethylene (20) sorbitan monostearate). The resulting mixture was subjected to a heating treatment in a paddle mixer heated to 200° C. An average time (retention time) that the mixture was retained in the paddle mixer was approximately 50 minutes. The heated material was cooled and then subjected to classification with use of JIS standard sieves having respective mesh sizes of 850 μm and 150 μm, so that surface-crosslinked water-absorbing resin particles (1) were obtained. Surface-crosslinked water-absorbing resin particles which remained on the 850 μm sieve (i.e., agglutinated particles having a particle diameter exceeding 850 μm) were crushed until they passed through the 850 μm sieve.

Next, with 100 parts by mass of the surface-crosslinked water-absorbing resin particles (1), a solution was mixed uniformly, the solution being obtained by mixing 1.0 parts by mass of deionized water and 0.01 parts by mass of diethylenetriamine pentaacetic acid trisodium (DTPA.3Na). Thereafter, in a windless environment, after a heating treatment was carried out at 60° C. for 45 minutes, agglutinated particles exceeding 850 μm were crushed until they passed through a JIS standard sieve having a mesh size of 850 μm, so that a particulate water-absorbing resin composition (1) which passed through the 850 μm sieve was obtained.

[Example 2] Alteration of Water-Absorbing Resin

Operations were carried out similarly to Example 1, except that 100 parts by mass of the water-absorbing resin particles (A2) having a non-uniform particle shape as obtained in Production Example 2 (particle diameter: 710 μm to 45 μm) were used. This produced surface-crosslinked water-absorbing resin particles (2), as well as a particulate water-absorbing resin composition (2) which passed through an 850 μm sieve.

[Example 3] Removal of Fine Powder (Second Classification) After Surface-Crosslinking The particulate water-absorbing resin composition (1) as obtained in Example 1 was further classified with use of a JIS standard sieve having a mesh size of 150 μm, so as to remove a fraction which passed through a the sieve having the mesh size of 150 μm. This produced a particulate water-absorbing resin composition (3) with a particle diameter of 850 μm to 150 μm.

[Example 4] Alteration of Type of Surfactant

Operations were carried out similarly to Example 1, except that the 0.001 parts by mass of polyoxyethylene (20) sorbitan monostearate was replaced with 0.001 parts by mass of sorbitan monolaurate (product name: IONET S-20, manufactured by Sanyo Chemical Industries, Ltd.). This produced surface-crosslinked water-absorbing resin particles (4), as well as a particulate water-absorbing resin composition (4) which passed through an 850 μm sieve.

[Example 5] Alteration of Type of Surfactant

Operations were carried out similarly to Example 2, except that the 0.001 parts by mass of polyoxyethylene (20) sorbitan monostearate was replaced with 0.010 parts by mass of sorbitan monolaurate (SPAN (registered trademark) 20, manufactured by Sigma-Aldrich), and the 0.01 parts by mass of the diethylenetriamine pentaacetic acid trisodium (DTPA.3Na) was replaced with 0.01 parts by mass of ethylenediamine tetramethylene phosphonic acid pentasodium (EDTMP.5Na). This produced surface-crosslinked water-absorbing resin particles (5), as well as a particulate water-absorbing resin composition (5) which passed through an 850 μm sieve.

Example 6

Operations were carried out similarly to Example 2, except that the amount of polyoxyethylene (20) sorbitan monostearate solution having a concentration of 10% by mass was changed to 0.1 parts by mass (so that there were 0.01 parts by mass of polyoxyethylene (20) sorbitan monostearate). This produced surface-crosslinked water-absorbing resin particles (6), as well as a particulate water-absorbing resin composition (6) which passed through an 850 μm sieve.

[Example 7] Alteration of Surface-Crosslinking Agent Composition Containing Surfactant Operations were carried out similarly to Example 2, except that the above-described surface-treating agent solution was replaced with a surface-treating agent solution obtained by mixing 0.32 parts by mass of 1,4-butanediol, 0.5 parts by mass of propylene glycol, 2.6 parts by mass of deionized water, and 0.01 parts by mass of a polyoxyethylene (20) sorbitan monostearate solution having a concentration of 10% by mass (so that there were 0.001 parts by mass of polyoxyethylene (20) sorbitan monostearate). This produced surface-crosslinked water-absorbing resin particles (7), as well as a particulate water-absorbing resin composition (7) which passed through an 850 μm sieve.

[Example 8] Alteration of Surface-Crosslinking Agent Composition

Operations were carried out similarly to Example 7, except that the 0.32 parts by mass of 1,4-butanediol was replaced with 0.3 parts by mass of 1,3-propanediol. This produced surface-crosslinked water-absorbing resin particles (8), as well as a particulate water-absorbing resin composition (8) which passed through an 850 μm sieve.

[Example 9] Alteration of Surface-Crosslinking Agent Composition Containing Surfactant Operations were carried out similarly to Example 2, except that the above-described surface-treating agent solution was replaced with a surface-treating agent solution obtained by mixing 1.0 parts by mass of ethylene glycol, 2.0 parts by mass of deionized water, and 0.01 parts by mass of a polyoxyethylene (20) sorbitan monostearate solution having a concentration of 10% by mass (so that there were 0.001 parts by mass of polyoxyethylene (20) sorbitan monostearate). This produced surface-crosslinked water-absorbing resin particles (9), as well as a particulate water-absorbing resin composition (9) which passed through an 850 μm sieve.

[Example 10] Alteration of Surface-Crosslinking Agent Composition

Operations were carried out similarly to Example 2, except that 0.03 parts by mass of ethylene glycol diglycidyl ether was added to the surface-treating agent solution. This produced surface-crosslinked water-absorbing resin particles (10), as well as a particulate water-absorbing resin composition (10) which passed through an 850 μm sieve.

[Example 11] Alteration of Type of Surfactant and Type of Chelating Agent

Operations were carried out similarly to Example 7, except that (1) the 0.001 parts by mass of polyoxyethylene (20) sorbitan monostearate was replaced with 0.001 parts by mass of polyoxyethylene (20) sorbitan monooleate and (2) the 0.01 parts by mass of diethylenetriamine pentaacetic acid trisodium (DTPA.3Na) was replaced with 0.02 parts by mass of triethylenetetramine hexaacetic acid hexasodium (TTHA.6Na). This produced surface-crosslinked water-absorbing resin particles (11), as well as a particulate water-absorbing resin composition (11) which passed through an 850 μm sieve.

[Example 12] Alteration of Type of Chelating Agent

Operations were carried out similarly to Example 11, except that the 0.02 parts by mass of triethylenetetramine hexaacetic acid hexasodium (TTHA.6Na) was replaced with 0.02 parts by mass of ethylenediamine-N,N'-disuccinic acid trisodium (EDDS.3Na). This produced surface-crosslinked water-absorbing resin particles (12), as well as a particulate water-absorbing resin composition (12) which passed through an 850 μm sieve.

[Example 13] Alteration of Type of Chelating Agent

Operations were carried out similarly to Example 11, except that the 0.02 parts by mass of triethylenetetramine hexaacetic acid hexasodium (TTHA.6Na) was replaced with 0.02 parts by mass of ethylenediamine tetramethylene phosphonic acid pentasodium (EDTMP.5Na). This produced surface-crosslinked water-absorbing resin particles (13), as well as a particulate water-absorbing resin composition (13) which passed through an 850 μm sieve.

[Example 14] Alteration of Type of Chelating Agent

Operations were carried out similarly to Example 11, except that the 0.02 parts by mass of triethylenetetramine hexaacetic acid hexasodium (TTHA.6Na) was replaced with 0.02 parts by mass of 3-hydroxy-2,2-iminodisuccinic acid tetrasodium (HIDS.4Na). This produced surface-crosslinked water-absorbing resin particles (14), as well as a particulate water-absorbing resin composition (14) which passed through an 850 μm sieve.

[Example 15] Alteration of Type of Surfactant, Type of Chelating Agent, and Amount of Chelating Agent Operations were carried out similarly to Example 8, except that (1) the 0.001 parts by mass of polyoxyethylene (20) sorbitan monostearate was replaced with 0.001 parts by mass of sorbitan monostearate (SPAN (registered trademark) 60) and (2) the 0.01 parts by mass of diethylenetriamine pentaacetic acid trisodium (DTPA.3Na) was replaced with 0.02 parts by mass of triethylenetetramine hexaacetic acid hexasodium (TTHA.6Na). This produced surface-crosslinked water-absorbing resin particles (15), as well as a particulate water-absorbing resin composition (15) which passed through an 850 μm sieve.

[Example 16] Alteration of Type of Chelating Agent

Operations were carried out similarly to Example 15, except that the 0.02 parts by mass of triethylenetetramine hexaacetic acid hexasodium (TTHA.6Na) was replaced with 0.02 parts by mass of ethylenediamine-N,N'-disuccinic acid trisodium (EDDS.3Na). This produced surface-crosslinked water-absorbing resin particles (16), as well as a particulate water-absorbing resin composition (16) which passed through an 850 μm sieve.

[Example 17] Alteration of Type of Chelating Agent

Operations were carried out similarly to Example 15, except that the 0.02 parts by mass of triethylenetetramine hexaacetic acid hexasodium (TTHA.6Na) was replaced with 0.02 parts by mass of ethylenediamine tetramethylene phosphonic acid pentasodium (EDTMP.5Na). This produced surface-crosslinked water-absorbing resin particles (17), as well as a particulate water-absorbing resin composition (17) which passed through an 850 μm sieve.

[Example 18] Alteration of Type of Chelating Agent

Operations were carried out similarly to Example 15, except that the 0.02 parts by mass of triethylenetetramine hexaacetic acid hexasodium (TTHA.6Na) was replaced with 0.02 parts by mass of 3-hydroxy-2,2-iminodisuccinic acid tetrasodium (HIDS.4Na). This produced surface-crosslinked water-absorbing resin particles (18), as well as a particulate water-absorbing resin composition (18) which passed through an 850 μm sieve.

[Example 19] Alteration of Type of Surfactant, Type of Chelating Agent, and Amount of Chelating Agent Operations were carried out similarly to Example 10, except that (1) the 0.001 parts by mass of polyoxyethylene (20) sorbitan monostearate was replaced with 0.001 parts by mass of polyethylene glycol monolaurate and (2) the 0.01 parts by mass of diethylenetriamine pentaacetic acid trisodium (DTPA.3Na) was replaced with 0.02 parts by mass of triethylenetetramine hexaacetic acid hexasodium (TTHA.6Na). This produced surface-crosslinked water-absorbing resin particles (19), as well as a particulate water-absorbing resin composition (19) which passed through an 850 μm sieve.

[Example 20] Alteration of Type of Chelating Agent

Operations were carried out similarly to Example 19, except that the 0.02 parts by mass of triethylenetetramine hexaacetic acid hexasodium (TTHA.6Na) was replaced with 0.02 parts by mass of ethylenediamine-N,N'-disuccinic acid trisodium (EDDS.3Na). This produced surface-crosslinked water-absorbing resin particles (20), as well as a particulate water-absorbing resin composition (20) which passed through an 850 μm sieve.

[Example 21] Alteration of Type of Chelating Agent

Operations were carried out similarly to Example 19, except that the 0.02 parts by mass of triethylenetetramine hexaacetic acid hexasodium (TTHA.6Na) was replaced with 0.02 parts by mass of ethylenediamine tetramethylene phosphonic acid pentasodium (EDTMP.5Na). This produced surface-crosslinked water-absorbing resin particles (21), as well as a particulate water-absorbing resin composition (21) which passed through an 850 μm sieve.

[Example 22] Alteration of Type of Chelating Agent

Operations were carried out similarly to Example 19, except that the 0.02 parts by mass of triethylenetetramine hexaacetic acid hexasodium (TTHA.6Na) was replaced with 0.02 parts by mass of 3-hydroxy-2,2-iminodisuccinic acid tetrasodium (HIDS.4Na). This produced surface-crosslinked water-absorbing resin particles (22), as well as a particulate water-absorbing resin composition (22) which passed through an 850 μm sieve.

[Example 23] Addition of Polyvalent Metal Salt

In Example 2, to the water-absorbing resin composition (2) as obtained in Example 2, a liquid mixture further added, the liquid mixture being constituted by 0.53 parts by mass of a 27.5 mass % aqueous aluminum sulfate solution (8 mass % based on aluminum oxide), 0.16 parts by mass of a 60 mass % aqueous sodium lactate solution, and 0.01 parts by mass of propylene glycol. Thereafter, in a windless environment, a resulting mixture was dried for 1 hour at 60° C. and then crushed until it passed through a JIS standard sieve having a mesh size of 850 μm. This produced a particulate water-absorbing resin composition (23) which passed through the 850 μm sieve.

[Example 24] Addition of Polyvalent Metal Salt

Operations were carried out similarly to Example 23, except that the liquid mixture added to the water-absorbing resin composition (2) was replaced with a liquid mixture constituted by 1.00 parts by mass by mass of a 27.5 mass % aqueous aluminum sulfate solution (8 mass % based on aluminum oxide), 0.30 parts by mass by mass of a 60 mass % aqueous sodium lactate solution, and 0.02 parts by mass of propylene glycol. This produced a particulate water-absorbing resin composition (24) which passed through an 850 μm sieve.

[Example 25] Addition of Polyvalent Metal Salt

Operations were carried out similarly to Example 24, except that the water-absorbing resin composition (2) was replaced with the water-absorbing resin composition (7). This produced a particulate water-absorbing resin composition (25) which passed through an 850 μm sieve.

[Example 26] Addition of Polyvalent Metal Salt

Operations were carried out similarly to Example 24, except that the water-absorbing resin composition (2) was replaced with the water-absorbing resin composition (13). This produced a particulate water-absorbing resin composition (26) which passed through an 850 μm sieve.

[Example 27] Addition of Polyvalent Metal Salt

Operations were carried out similarly to Example 23, except that the water-absorbing resin composition (2) was replaced with the water-absorbing resin composition (19). This produced a particulate water-absorbing resin composition (27) which passed through an 850 μm sieve.

[Example 28] Addition of Inorganic Fine Particles

In Example 2, to the water-absorbing resin composition (2) as obtained in Example 2, 0.30 parts by mass of Aerosil (registered trademark) 200 (manufactured by Nippon Aerosil Co., Ltd.) was further added. This produced a particulate water-absorbing resin composition (28) which passed through an 850 μm sieve.

[Example 29] Addition of Dust Inhibiting Agent

To the water-absorbing resin composition (23) as obtained in Example 23, 0.5 parts by mass of an aqueous polyethylene glycol 600 solution having a concentration of 10% by mass was added and mixed therewith. This produced a particulate water-absorbing resin composition (29) which passed through an 850 μm sieve.

[Example 30] Addition of Dust Inhibiting Agent

Operations were carried out similarly to Example 29, except that the 0.5 parts by mass of the aqueous polyethylene glycol 600 solution having a concentration of 10% by mass was replaced with 0.5 parts by mass of an aqueous polyethylene glycol 400 solution having a concentration of 10% by mass. This produced a water-absorbing resin composition (30).

[Example 31] No Surfactant; Only Chelating Agent Added

With 100 parts by mass of the water-absorbing resin particles (A2) having a non-uniform particle shape (particle diameter: 710 μm to 45 μm) as obtained in Production Example 2, a surface-treating agent solution was uniformly mixed, the surface-treating agent solution being obtained by mixing 0.4 parts by mass of ethylene carbonate, 0.6 parts by mass of propylene glycol, and 2.5 parts by mass of deionized water. The resulting mixture was subjected to a heating treatment in a paddle mixer heated to 200° C. An average time (retention time) that the mixture was retained in the paddle mixer was approximately 55 minutes. The heated material was cooled and then subjected to classification with use of JIS standard sieves. Used for classification were a sieve having a mesh size of 850 μm and a sieve having a mesh size of 212 μm. Particles which passed through the sieve having the mesh size of 850 μm but which were retained by the sieve having the mesh size of 212 μm were selected. In this way, surface-crosslinked water-absorbing resin particles (31) were obtained. Note that in Example 31, no crushing was carried out on agglutinated particles which remained on the 850 μm sieve during classification.

Next, with 100 parts by mass of the surface-crosslinked water-absorbing resin particles (31), a solution was mixed uniformly, the solution being obtained by mixing 1.0 parts by mass of deionized water and 0.01 parts by mass of diethylenetriamine pentaacetic acid trisodium (DTPA.3Na). Thereafter, in a windless environment, a resulting mixture was subjected to a heating treatment for minutes at 60° C. and then crushed until it passed through a JIS standard sieve having a mesh size of 850 μm. This produced a particulate water-absorbing resin composition (31) which passed through an 850 μm sieve.

[Example 32] Removal of Fine Powder (Second Classification) After Surface-Crosslinking Operations were carried out similarly to Example 31, except that the classification carried out after the surface-crosslinking step was changed to classification using an air classifier (product name: Hi-Bolter MR-300S, manufactured by Toyo Hitec Co., Ltd.) having a sieve mesh with a mesh size of 150 μm (feed rate of crosslinked water-absorbing resin particles: 100 kg/hr). This produced a particulate water-absorbing resin composition (32).

[Example 33] Addition of Polyvalent Metal Salt

Operations were carried out similarly to Example 23, except that the water-absorbing resin composition (2) was replaced with the water-absorbing resin composition (31). This produced a particulate water-absorbing resin composition (33) which passed through an 850 μm sieve.

[Example 34] Addition of Polyvalent Metal Salt

Operations were carried out similarly to Example 24, except that the water-absorbing resin composition (2) was replaced with the water-absorbing resin composition (31). This produced a particulate water-absorbing resin composition (34) which passed through an 850 μm sieve.

[Example 35] Addition of Dust Inhibiting Agent

To the water-absorbing resin composition (34) as obtained in Example 34, 0.5 parts by mass of an aqueous polyethylene glycol 400 solution having a concentration of 10% by mass was added and mixed. This produced a particulate water-absorbing resin composition (35) which passed through an 850 μm sieve.

[Example 36] Addition of Inorganic Fine Particles

To the water-absorbing resin composition (31) as obtained in Example 31, 0.30 parts by mass of Aerosil (registered trademark) 200 (manufactured by Nippon Aerosil Co., Ltd.) was added. This produced a particulate water-absorbing resin composition (36) which passed through an 850 μm sieve.

[Comparative Example 1] Without Surfactant

Surface-crosslinked comparative water-absorbing resin particles (1) and a particulate comparative water-absorbing resin composition (1) having passed through a 850-μm mesh were obtained by carrying out the same operations as in Example 1, except that the 10% by mass polyoxyethylene (20) sorbitan monostearate solution (product name: RHEODOL TW-S120V; available from Kao Corporation) was not used in a surface-treating agent solution.

[Comparative Example 2] Without Surfactant

Surface-crosslinked comparative water-absorbing resin particles (2) and a particulate comparative water-absorbing resin composition (2) having passed through a 850-μm mesh were obtained by carrying out the same operations as in Example 2, except that the 10% by mass polyoxyethylene (20) sorbitan monostearate solution (product name: RHEODOL TW-S120V; available from Kao Corporation) was not used in a surface-treating agent solution.

[Comparative Example 3] Without Chelating Agent

Surface-crosslinked comparative water-absorbing resin particles (3) and a particulate comparative water-absorbing resin composition (3) having passed through a 850-μm mesh were obtained by carrying out the same operations as in Example 1, except that 0.001 parts by mass of the polyoxyethylene (20) sorbitan monostearate was replaced with 0.001 parts by mass of sorbitan monolaurate (product name: IONET S-20; available from Sanyo Chemical Industries, Ltd.), and the diethylenetriamine pentaacetic acid trisodium (DTPA.3Na) was not used.

[Comparative Example 4] Without Chelating Agent

Surface-crosslinked comparative water-absorbing resin particles (4) and a particulate comparative water-absorbing resin composition (4) having passed through a 850-μm mesh were obtained by carrying out the same operations as in Example 2, except that the diethylenetriamine pentaacetic acid trisodium (DTPA.3Na) was not used.

[Comparative Example 5] Addition of Surfactant After Surface-Crosslinking 100 parts by mass of the water-absorbing resin particles (A2), obtained in Production Example 2, having a non-uniform particle shape (particle diameter: 710 μm to 45 μm) was mixed uniformly with a surface-treating agent solution which was obtained by mixing 0.385 parts by mass of ethylene carbonate, 0.644 parts by mass of propylene glycol, and 2.6 parts by mass of deionized water. Thereafter, the resulting mixture was subjected to heating treatment in a paddle mixer which was heated at 200° C. A mean retention time of the mixture was approximately 50 minutes. The heated product was cooled and classified with JIS standard sieves having respective mesh sizes of 850 μm and 150 μm. In this way, surface-crosslinked comparative water-absorbing resin particles (5) was obtained. Note that water-absorbing resin particles (agglomerates) on the sieve having a mesh size of 850 μm after surface-crosslinking was crushed until they passed through the sieve having a mesh size of 850 μm.

Next, 100 parts by mass of the surface-crosslinked comparative water-absorbing resin particles (5) was mixed uniformly with a solution obtained by mixing 0.01 parts by mass of a 10% by mass polyoxyethylene (20) sorbitan monostearate solution (0.001 parts by mass of polyoxyethylene (20) sorbitan monostearate), 0.01 parts by mass of diethylenetriamine pentaacetic acid trisodium (DTPA.3Na), and 1.0 parts by mass of deionized water. Thereafter, the resulting mixture, after subjected to heating treatment in a windless environment at 60° C. for 45 minutes, was crushed until it passed through a JIS standard sieve having a mesh size of 850 μm. In this way, a particulate comparative water-absorbing resin composition (5) having passed through a 850-μm mesh was obtained.

[Comparative Example 6] Increase in Amount of Surfactant

Surface-crosslinked comparative water-absorbing resin particles (6) and a particulate comparative water-absorbing resin composition (6) having passed through a 850-μm mesh were obtained by carrying out the same operations as in Example 2, except that the amount of the 10% by mass polyoxyethylene (20) sorbitan monostearate solution used was changed to 1.2 parts by mass (0.12 parts by mass of polyoxyethylene (20) sorbitan monostearate).

[Comparative Example 7] Without Surfactant

Surface-crosslinked comparative water-absorbing resin particles (7) and a particulate comparative water-absorbing resin composition (7) having passed through a 850-μm mesh were obtained by carrying out the same operations as in Example 7, except that the 10% by mass polyoxyethylene (20) sorbitan monostearate solution was not used in a surface-treating agent solution.

[Comparative Example 8] Without Surfactant

Surface-crosslinked comparative water-absorbing resin particles (8) and a particulate comparative water-absorbing resin composition (8) having passed through a 850-μm mesh were obtained by carrying out the same operations as in Example 8, except that the 10% by mass polyoxyethylene (20) sorbitan monostearate solution was not used in a surface-treating agent solution.

[Comparative Example 9] Without Surfactant

Surface-crosslinked comparative water-absorbing resin particles (9) and a particulate comparative water-absorbing resin composition (9) having passed through a 850-μm mesh were obtained by carrying out the same operations as in Example 9, except that the 10% by mass polyoxyethylene (20) sorbitan monostearate solution was not used in a surface-treating agent solution.

[Comparative Example 10] Without Chelating Agent

Surface-crosslinked comparative water-absorbing resin particles (10) and a particulate comparative water-absorbing resin composition (10) having passed through a 850-μm mesh were obtained by carrying out the same operations as in Example 7, except that the diethylenetriamine pentaacetic acid trisodium (DTPA.3Na) was not used with respect to the surface-crosslinked water-absorbing resin particles.

[Comparative Example 11] Without Chelating Agent

Surface-crosslinked comparative water-absorbing resin particles (11) and a particulate comparative water-absorbing resin composition (11) having passed through a 850-μm mesh were obtained by carrying out the same operations as in Example 8, except that the diethylenetriamine pentaacetic acid trisodium (DTPA.3Na) was not used with respect to the surface-crosslinked water-absorbing resin particles.

[Comparative Example 12] Without Chelating Agent

Surface-crosslinked comparative water-absorbing resin particles (12) and a particulate comparative water-absorbing resin composition (12) having passed through a 850-μm mesh were obtained by carrying out the same operations as in Example 9, except that the diethylenetriamine pentaacetic acid trisodium (DTPA.3Na) was not used with respect to the surface-crosslinked water-absorbing resin particles.

[Comparative Example 13] Without Surfactant

Surface-crosslinked comparative water-absorbing resin particles (13) and a particulate comparative water-absorbing resin composition (13) having passed through a 850-μm mesh were obtained by carrying out the same operations as in Example 11, except that the polyoxyethylene (20) sorbitan monooleate was not used in a surface-treating agent solution.

[Comparative Example 14] Without Surfactant

Surface-crosslinked comparative water-absorbing resin particles (14) and a particulate comparative water-absorbing resin composition (14) having passed through a 850-μm mesh were obtained by carrying out the same operations as in Example 12, except that the polyoxyethylene (20) sorbitan monooleate was not used in a surface-treating agent solution.

[Comparative Example 15] Without Surfactant

Surface-crosslinked comparative water-absorbing resin particles (15) and a particulate comparative water-absorbing resin composition (15) having passed through a 850-μm mesh were obtained by carrying out the same operations as in Example 13, except that the polyoxyethylene (20) sorbitan monooleate was not used in a surface-treating agent solution.

[Comparative Example 16] Without Surfactant

Surface-crosslinked comparative water-absorbing resin particles (16) and a particulate comparative water-absorbing resin composition (16) having passed through a 850-μm mesh were obtained by carrying out the same operations as in Example 14, except that the polyoxyethylene (20) sorbitan monooleate was not used in a surface-treating agent solution.

[Comparative Example 17] Without Chelating Agent

Surface-crosslinked comparative water-absorbing resin particles (17) and a comparative water-absorbing resin composition (17) were obtained by carrying out the same operations as in Example 11, except that the triethylenetetraamine hexaacetic acid hexasodium (TTHA.6Na) was not used with respect to the surface-crosslinked water-absorbing resin particles.

[Comparative Example 18] Without Chelating Agent

Surface-crosslinked comparative water-absorbing resin particles (18) and a particulate comparative water-absorbing resin composition (18) having passed through a 850-μm mesh were obtained by carrying out the same operations as in Example 15, except that the triethylenetetraamine hexaacetic acid hexasodium (TTHA.6Na) was not used with respect to the surface-crosslinked water-absorbing resin particles.

[Comparative Example 19] Without Chelating Agent

Surface-crosslinked comparative water-absorbing resin particles (19) and a particulate comparative water-absorbing resin composition (19) having passed through a 850-μm mesh were obtained by carrying out the same operations as in Example 19, except that the triethylenetetraamine hexaacetic acid hexasodium (TTHA.6Na) was not used with respect to the surface-crosslinked water-absorbing resin particles.

[Comparative Example 20] Additional Test of Example of Patent Literature 3 (Addition of Surfactant and Chelating Agent After Surface-Crosslinking)

Surface-crosslinked comparative water-absorbing resin particles (20) and a particulate comparative water-absorbing resin composition (20) having passed through a 850-μm mesh were obtained by carrying out the same operations as in Example 1 which is described in Patent Literature 3 (Japanese Patent Application Publication, Tokukai, No. 2014-073448) of the background art.

Specifically, in conformity with [Example 1] of Patent Literature 3, a reactive surfactant (X) represented by $CH_3$—$Si(CH_3)_2$—O—$[Si(CH_3)_2$—O$]_m$—$[Si(CH_3)(R)$—O—$]_n$—$Si(CH_3)_3$ was synthesized, wherein R=$(C_2H_4O)_a(C_3H_6O)_b$—$NH_2$. The reactive surfactant (X) had HLB of 10 and had a viscosity of 4000 $mm^2$/s.

Furthermore, 0.5 parts by mass of a mixture solution obtained by mixing 0.05 parts by mass of the reactive surfactant (X) and 0.45 parts by mass of 2-propanol was added, while being stirred, to 100 parts by mass of the water-absorbing resin particles (A) (particle diameter: 850 μm to 150 μm) obtained in Production Example of Patent Literature 3. Subsequently, an aqueous solution in which 0.04 parts by mass of ethylenediaminetetra (methylenephosphonic acid) pentasodium (hereinafter abbreviated to "EDTMP.5Na") was dissolved in 6.66 parts by mass of water was added, while being stirred, and was mixed for 1 minute. Thereafter, the resulting mixture was put in a reclosable bag (available from SEISANNIPPONSHA Ltd.; Uni-Pack (Registered Trademark)), and the reclosable bag was then sealed. The mixture was hardened at 80° C. for 1 hour. Thereafter, the resulting hardened product was crushed until it passed through a JIS standard sieve having a mesh size of 850 μm, so that a comparative water-absorbing resin composition (20) (particulate water-absorbing agent (1) of Patent Literature 3) was obtained.

[Comparative Example 21] Additional Test of Example of Patent Literature 4 (Addition of Surfactant and Chelating Agent After Surface-Crosslinking)

Surface-crosslinked comparative water-absorbing resin particles (21) and a particulate comparative water-absorbing resin composition (21) having passed through a 850-μm mesh were obtained by carrying out the same operations as in Example 1 which is described in Patent Literature 4 (International Publication No. 2012/133734) of the background art.

Specifically, 0.706 parts by mass of zinc stearate water dispersion (available from ADEKA CHEMICAL SUPPLY Co., Ltd.; product name: AFCO-DISPER ZD (Registered Trademark); solid content of 42.5% by mass; containing a surfactant) and 6.254 parts by mass of water were mixed in conformity with [Example 1] of Patent Literature 4. Thereafter, 0.04 parts by mass of ethylenediaminetetra (methylenephosphonic acid) pentasodium (hereinafter, abbreviated to "EDTMP.5Na") was added. In this way, a dispersion liquid (1) was prepared.

Next, 7 parts by mass of the dispersion liquid (1) (virtual added amount; 0.3 parts by mass of zinc stearate, 0.04 parts by mass of EDTMP.5Na, 6.66 parts by mass of water) was added, while being stirred, to 100 parts by mass of the surface-crosslinked water-absorbing resin particles (A1) (particle diameter before surface-crosslinking: 850 μm to 150 μm) obtained in Production Example 1 of Patent Literature 4, and was mixed for 1 minute. Thereafter, the resulting mixture was put in a reclosable bag, and the reclosable bag was then sealed. The mixture was hardened at 80° C. for 1 hour. Thereafter, the resulting hardened product was crushed until it passed through a JIS standard sieve having a mesh size of 850 μm, so that water-absorbing resin particles (B1) were obtained.

Further, a surfactant aqueous solution (1) was prepared from 0.1 parts by mass of polyoxyethylene alkyl ether (available from Nippon Shokubai Co., Ltd.; SOFTANOL 90 (Registered Trademark); solid content of 100% by mass) and 2.0 parts by mass of water. Then, 2.1 parts by mass of the surfactant aqueous solution (1) was added, while being stirred, to 100 parts by mass of the water-absorbing resin particles (B1), and was mixed for 1 minute. Thereafter, the resulting mixture was put in a reclosable bag (available from SEISANNIPPONSHA Ltd.; Uni-Pack (Registered Trademark)), and the reclosable bag was then sealed. The mixture was hardened at 80° C. for 1 hour. Thereafter, the resulting hardened product was crushed (sized) until it passed through a JIS standard sieve having a mesh size of 850 μm, so that a comparative water-absorbing resin composition (21) (particulate water-absorbing agent (1) of Patent Literature 4) was obtained.

[Comparative Example 22] Additional Test of Example of Patent Literature 5 (Addition of Surfactant and Chelating Agent After Surface-Crosslinking)

Surface-crosslinked comparative water-absorbing resin particles (22) and a particulate comparative water-absorbing resin composition (22) having passed through a 850-μm mesh were obtained by carrying out the same operations as in Example 14 which is described in Patent Literature 5 (International Publication No. 2009/048145) of the background art.

Specifically, in conformity with [Example 14] of Patent Literature 5, 2.015 parts by mass of a solution obtained by mixing 10 ppm by mass of hexanoic acid (available from Wako Pure Chemical Industries, Ltd.; CAS-No. 142-62-1), 10 ppm by mass of ethyl butyrate (available from Wako Pure Chemical Industries, Ltd.; CAS-No. 105-54-4), 10 ppm by mass of 3-methyl-2-cyclopentene-1-on (available from Kanto Chemical Co., Inc.; CAS-No. 2758-18-1), 0.01 parts by mass of diethylenetriamine pentaacetate trisodium, 0.002 parts by mass of polyoxyethylene (20) sorbitan monostearate (product name: RHEODOL TW-5120V; marketed by Kao Corporation), 1.3 parts by mass of water, and 0.7 parts by mass of ethanol was added to and mixed with 100 parts by mass of the water-absorbing resin particles (1) obtained in Production Example 1 of Patent Literature 4. Thereafter, the resulting mixture was allowed to stand in a sealed windless dryer at 60° C. for 1 hour and was then allowed to pass through a JIS standard sieve having a mesh size of 850 µm, so that a comparative water-absorbing resin composition (22) (water-absorbing resin composition (14) of Patent Literature 4) was obtained.

(Results)

Table 1 shows the results of measurements of properties of the particulate water-absorbing resin compositions (1) to (36) and comparative particulate water-absorbing resin compositions (1) to (22).

Further, the water-absorbing resin compositions (1) to (36) and comparative water-absorbing resin compositions (1) to (22) were used to prepare individual absorbent articles. Table 1 also shows the results of performance evaluations of the absorbent articles.

It should be noted that each of the obtained water-absorbing resin compositions was a particulate water-absorbing resin composition in which particles having a particle diameter of 850 µm to 150 µm account for not less than 95% by mass of the whole. Particularly, in Example 2 in which re-classification (second classification) was carried out, particles having passed through a 150-µm mesh were not more than 2.0%.

TABLE 1

| | CRC g/g | AAP 0.3 g/g | AAP 0.7 g/g | VDAUP 0.3 g/g | Surface-eluted soluble component mass % | PDT[*1] 1-hour eluted soluble component wt % | SD[*2] | AVS[*3] |
|---|---|---|---|---|---|---|---|---|
| Water-absorbing resin composition (1) | 40.0 | 33.8 | 20.5 | 20.2 | 1.9 | 17.4 | 2.0 | 0.11 |
| Water-absorbing resin composition (2) | 38.0 | 33.2 | 24.0 | 22.0 | 0.8 | 16.8 | 1.8 | 0.11 |
| Water-absorbing resin composition (3) | 38.4 | 33.5 | 24.2 | 21.8 | 0.8 | 16.5 | 1.8 | 0.11 |
| Water-absorbing resin composition (4) | 41.8 | 32.5 | 13.5 | 18.6 | 4.4 | 17.6 | 2.2 | 0.15 |
| Water-absorbing resin composition (5) | 36.0 | 32.0 | 25.1 | 22.3 | 0.6 | 15.9 | 1.6 | 0.17 |
| Water-absorbing resin composition (6) | 38.2 | 33.4 | 24.3 | 21.8 | 0.8 | 16.3 | 1.8 | 0.10 |
| Water-absorbing resin composition (7) | 38.2 | 33.0 | 24.3 | 21.7 | 0.9 | 16.5 | 1.6 | 0.11 |
| Water-absorbing resin composition (8) | 37.9 | 32.9 | 24.2 | 21.8 | 0.8 | 16.6 | 1.6 | 0.11 |
| Water-absorbing resin composition (9) | 37.4 | 32.2 | 24.0 | 21.4 | 0.8 | 17.2 | 1.8 | 0.11 |
| Water-absorbing resin composition (10) | 36.8 | 33.5 | 25.3 | 22.3 | 0.6 | 15.1 | 1.4 | 0.11 |
| Water-absorbing resin composition (11) | 39.4 | 34.3 | 22.0 | 20.8 | 1.6 | 15.8 | 1.6 | 0.10 |
| Water-absorbing resin composition (12) | 38.0 | 32.9 | 24.3 | 21.6 | 1.1 | 15.0 | 1.2 | 0.10 |
| Water-absorbing resin composition (13) | 38.2 | 33.1 | 24.1 | 21.6 | 0.8 | 15.5 | 1.4 | 0.10 |
| Water-absorbing resin composition (14) | 37.8 | 32.5 | 24.0 | 21.8 | 1.0 | 15.3 | 1.2 | 0.10 |
| Water-absorbing resin composition (15) | 37.7 | 32.2 | 24.4 | 21.4 | 1.1 | 15.5 | 1.4 | 0.16 |
| Water-absorbing resin composition (16) | 37.5 | 32.0 | 23.8 | 21.5 | 1.2 | 15.2 | 1.2 | 0.16 |
| Water-absorbing resin composition (17) | 38.0 | 33.1 | 24.3 | 21.5 | 0.8 | 15.7 | 1.4 | 0.16 |
| Water-absorbing resin composition (18) | 37.5 | 32.0 | 24.0 | 21.6 | 0.8 | 15.0 | 1.2 | 0.16 |
| Water-absorbing resin composition (19) | 37.0 | 33.3 | 25.5 | 22.3 | 0.5 | 15.0 | 1.2 | 0.13 |
| Water-absorbing resin composition (20) | 37.1 | 33.0 | 25.1 | 21.9 | 0.7 | 14.8 | 1.2 | 0.13 |
| Water-absorbing resin composition (21) | 37.0 | 33.1 | 25.3 | 22.1 | 0.6 | 15.5 | 1.2 | 0.13 |
| Water-absorbing resin composition (22) | 37.1 | 33.0 | 25.2 | 22.0 | 0.6 | 14.9 | 1.2 | 0.13 |
| Water-absorbing resin composition (23) | 38.0 | 33.0 | 23.5 | 20.5 | 0.7 | 17.0 | 2.0 | 0.11 |
| Water-absorbing resin composition (24) | 37.8 | 32.7 | 23.1 | 18.8 | 0.6 | 17.0 | 2.0 | 0.11 |
| Water-absorbing resin composition (25) | 38.1 | 32.1 | 23.2 | 18.7 | 0.8 | 16.8 | 1.6 | 0.11 |
| Water-absorbing resin composition (26) | 38.0 | 32.2 | 23.6 | 18.9 | 0.9 | 16.1 | 1.6 | 0.10 |
| Water-absorbing resin composition (27) | 37.0 | 32.2 | 24.8 | 19.4 | 0.5 | 15.2 | 1.4 | 0.13 |
| Water-absorbing resin composition (28) | 37.0 | 28.8 | 18.1 | 22.1 | 0.8 | 15.6 | 1.4 | 0.13 |
| Water-absorbing resin composition (29) | 38.0 | 33.1 | 23.8 | 20.6 | 0.7 | 17.0 | 2.0 | 0.11 |

TABLE 1-continued

| | | | | | | | | |
|---|---|---|---|---|---|---|---|---|
| Water-absorbing resin composition (30) | 38.0 | 33.0 | 24.1 | 20.7 | 0.7 | 16.8 | 2.0 | 0.11 |
| Water-absorbing resin composition (31) | 37.9 | 33.0 | 24.2 | 22.4 | 0.7 | 16.4 | 1.6 | |
| Water-absorbing resin composition (32) | 38.4 | 33.7 | 25.0 | 22.7 | 0.5 | 15.8 | 1.4 | |
| Water-absorbing resin composition (33) | 37.9 | 32.4 | 23.2 | 21.2 | 0.7 | 16.8 | 1.8 | |
| Water-absorbing resin composition (34) | 37.7 | 31.8 | 22.8 | 19.1 | 0.7 | 17.1 | 1.8 | |
| Water-absorbing resin composition (35) | 37.6 | 31.7 | 22.5 | 19.2 | 0.7 | 17.0 | 1.8 | |
| Water-absorbing resin composition (36) | 37.9 | 28.4 | 17.9 | 22.1 | 0.7 | 16.3 | 1.4 | |
| Comparative water-absorbing resin composition (1) | 40.1 | 31.3 | 18.5 | 14.8 | 3.2 | 21.6 | 3.2 | — |
| Comparative water-absorbing resin composition (2) | 37.8 | 31.2 | 21.3 | 19.7 | 2.2 | 20.0 | 3.0 | — |
| Comparative water-absorbing resin composition (3) | 40.5 | 33.0 | 19.2 | 15.4 | | 37.1 | 5.0 | 0.15 |
| Comparative water-absorbing resin composition (4) | 38.3 | 33.3 | 23.6 | 21.4 | | 34.4 | 5.0 | 0.11 |
| Comparative water-absorbing resin composition (5) | 37.9 | 31.0 | 21.2 | 19.6 | 2.2 | 20.3 | 3.2 | 0.11 |
| Comparative water-absorbing resin composition (6) | 43.9 | 27.4 | 7.8 | 6.2 | 6.9 | 28.0 | 4.6 | 0.11 |
| Comparative water-absorbing resin composition (7) | 38.0 | 30.8 | 21.1 | 19.5 | 2.3 | 20.1 | 3.0 | — |
| Comparative water-absorbing resin composition (8) | 38.1 | 30.9 | 21.0 | 19.5 | 2.2 | 20.4 | 3.2 | — |
| Comparative water-absorbing resin composition (9) | 37.3 | 30.4 | 20.7 | 19.2 | 2.4 | 21.0 | 3.4 | — |
| Comparative water-absorbing resin composition (10) | 37.8 | 31.2 | 21.1 | 19.6 | | 34.5 | 5.0 | 0.11 |
| Comparative water-absorbing resin composition (11) | 37.9 | 31.2 | 21.0 | 19.6 | | 34.8 | 5.0 | 0.11 |
| Comparative water-absorbing resin composition (12) | 37.5 | 31.5 | 20.7 | 19.6 | | 35.0 | 5.0 | 0.11 |
| Comparative water-absorbing resin composition (13) | 38.4 | 31.0 | 20.3 | 19.2 | 2.4 | 20.0 | 2.8 | — |
| Comparative water-absorbing resin composition (14) | 38.0 | 30.5 | 20.5 | 19.1 | 2.3 | 19.8 | 2.8 | — |
| Comparative water-absorbing resin composition (15) | 38.3 | 30.8 | 20.0 | 19.0 | 2.3 | 20.1 | 3.2 | — |
| Comparative water-absorbing resin composition (16) | 38.4 | 30.9 | 20.1 | 19.1 | 2.5 | 20.4 | 3.0 | — |
| Comparative water-absorbing resin composition (17) | 38.2 | 30.8 | 19.8 | 18.9 | | 34.2 | 5.0 | 0.10 |
| Comparative water-absorbing resin composition (18) | 37.8 | 30.3 | 20.2 | 18.9 | | 33.8 | 5.0 | 0.16 |
| Comparative water-absorbing resin composition (19) | 37.0 | 31.1 | 21.8 | 19.9 | | 32.7 | 4.8 | 0.13 |
| Comparative water-absorbing resin composition (20) | 37.8 | 27.0 | | | | 20.1 | 3.0 | — |
| Comparative water-absorbing resin composition (21) | 37.3 | 26.8 | | | | 20.3 | 3.2 | — |
| Comparative water-absorbing resin composition (22) | 34.0 | 30.1 | 23.3 | | | 19.2 | 2.2 | — |

| | Moisture Content mass % | Surface Tension mN/m | Content of water-absorbing resin in dust ppm | MABR*4 % | FGBP | Liquid absorbing time sec | Re-wet g |
|---|---|---|---|---|---|---|---|
| Water-absorbing resin composition (1) | 2.8 | 72 | 185 | 95 | 4 | 270 | 12 |
| Water-absorbing resin composition (2) | 2.9 | 73 | 205 | 100 | 8 | 250 | 14 |
| Water-absorbing resin composition (3) | 3.0 | 73 | 177 | 93 | 8 | 240 | 13 |
| Water-absorbing resin composition (4) | 3.2 | 72 | 187 | 96 | 3 | 270 | 13 |
| Water-absorbing resin composition (5) | 3.1 | 72 | 203 | 100 | 20 | 260 | 14 |
| Water-absorbing resin composition (6) | 3.0 | 71 | 210 | 95 | 7 | 260 | 15 |
| Water-absorbing resin composition (7) | 2.7 | 73 | 195 | 95 | 7 | 250 | 13 |

TABLE 1-continued

| | | | | | | | |
|---|---|---|---|---|---|---|---|
| Water-absorbing resin composition (8) | 2.8 | 73 | 200 | 100 | 8 | 260 | 14 |
| Water-absorbing resin composition (9) | 2.8 | 72 | 210 | 100 | 10 | 260 | 14 |
| Water-absorbing resin composition (10) | 2.9 | 73 | 208 | 60 | 12 | 240 | 12 |
| Water-absorbing resin composition (11) | 3.2 | 70 | 208 | 95 | 5 | 270 | 12 |
| Water-absorbing resin composition (12) | 3.0 | 70 | 205 | 97 | 8 | 260 | 11 |
| Water-absorbing resin composition (13) | 3.0 | 71 | 210 | 95 | 8 | 250 | 11 |
| Water-absorbing resin composition (14) | 2.9 | 72 | 211 | 95 | 9 | 260 | 12 |
| Water-absorbing resin composition (15) | 2.8 | 71 | 208 | 98 | 10 | 250 | 12 |
| Water-absorbing resin composition (16) | 2.8 | 71 | 198 | 99 | 10 | 260 | 11 |
| Water-absorbing resin composition (17) | 2.9 | 72 | 200 | 100 | 8 | 260 | 11 |
| Water-absorbing resin composition (18) | 3.0 | 71 | 201 | 95 | 10 | 250 | 10 |
| Water-absorbing resin composition (19) | 2.9 | 71 | 190 | 52 | 12 | 240 | 11 |
| Water-absorbing resin composition (20) | 2.9 | 72 | 195 | 61 | 11 | 230 | 10 |
| Water-absorbing resin composition (21) | 2.7 | 72 | 200 | 55 | 11 | 240 | 11 |
| Water-absorbing resin composition (22) | 3.0 | 71 | 188 | 56 | 10 | 230 | 10 |
| Water-absorbing resin composition (23) | 3.0 | 73 | 198 | 38 | 38 | 230 | 14 |
| Water-absorbing resin composition (24) | 3.1 | 73 | 210 | 25 | 46 | 220 | 14 |
| Water-absorbing resin composition (25) | 2.9 | 72 | 190 | 31 | 50 | 220 | 13 |
| Water-absorbing resin composition (26) | 3.0 | 72 | 205 | 28 | 47 | 220 | 12 |
| Water-absorbing resin composition (27) | 3.0 | 71 | 201 | 3 | 60 | 210 | 11 |
| Water-absorbing resin composition (28) | 2.7 | 71 | 204 | 0 | 260 | 160 | 14 |
| Water-absorbing resin composition (29) | 2.9 | 71 | 18 | 5 | 38 | 240 | 14 |
| Water-absorbing resin composition (30) | 3.1 | 70 | 12 | 7 | 35 | 240 | 14 |
| Water-absorbing resin composition (31) | 2.4 | 74 | 185 | 93 | 10 | 240 | 13 |
| Water-absorbing resin composition (32) | 2.6 | 74 | 180 | 90 | 10 | 240 | 12 |
| Water-absorbing resin composition (33) | 2.8 | 73 | 179 | 33 | 41 | 230 | 14 |
| Water-absorbing resin composition (34) | 3.0 | 73 | 173 | 21 | 55 | 220 | 13 |
| Water-absorbing resin composition (35) | 3.0 | 72 | 10 | 4 | 57 | 220 | 13 |
| Water-absorbing resin composition (36) | 2.5 | 72 | 183 | 0 | 280 | 150 | 13 |
| Comparative water-absorbing resin composition (1) | 4.0 | 73 | 310 | 98 | 3 | 300 | 18 |
| Comparative water-absorbing resin composition (2) | 4.1 | 73 | 352 | 100 | 5 | 290 | 20 |
| Comparative water-absorbing resin composition (3) | 4.0 | 73 | | | | | |
| Comparative water-absorbing resin composition (4) | 4.2 | 73 | | | | | |
| Comparative water-absorbing resin composition (5) | 4.1 | 71 | 305 | 98 | 7 | 290 | 19 |
| Comparative water-absorbing resin composition (6) | 5.4 | 39 | 204 | 100 | 1 | 310 | 24 |
| Comparative water-absorbing resin composition (7) | 3.8 | 73 | 311 | 99 | 6 | 290 | 18 |
| Comparative water-absorbing resin composition (8) | 3.8 | 73 | 313 | 100 | 6 | 290 | 19 |
| Comparative water-absorbing resin composition (9) | 3.8 | 73 | 321 | 98 | 8 | 300 | 21 |
| Comparative water-absorbing resin composition (10) | 3.9 | 72 | | | | | |
| Comparative water-absorbing resin composition (11) | 3.9 | 72 | | | | | |

TABLE 1-continued

| | | | | | | | |
|---|---|---|---|---|---|---|---|
| Comparative water-absorbing resin composition (12) | 3.9 | 72 | | | | | |
| Comparative water-absorbing resin composition (13) | 3.8 | 73 | 309 | 100 | 5 | 290 | 17 |
| Comparative water-absorbing resin composition (14) | 4.0 | 73 | 316 | 100 | 4 | 280 | 17 |
| Comparative water-absorbing resin composition (15) | 4.0 | 72 | 321 | 98 | 4 | 290 | 18 |
| Comparative water-absorbing resin composition (16) | 3.9 | 71 | 333 | 98 | 4 | 280 | 17 |
| Comparative water-absorbing resin composition (17) | 4.0 | 70 | | | | | |
| Comparative water-absorbing resin composition (18) | 4.1 | 71 | | | | | |
| Comparative water-absorbing resin composition (19) | 3.9 | 71 | | | | | |
| Comparative water-absorbing resin composition (20) | 11 | 68 | | | | 280 | 26 |
| Comparative water-absorbing resin composition (21) | 12.1 | 45 | | | | 300 | 25 |
| Comparative water-absorbing resin composition (22) | 3.1 | 70 | | | | | |

*[1]PDT is an abbreviation for "Post-degradation-test".
*[2]SD is an abbreviation for "Stickiness of diaper" (i.e., average value of results of evaluations made by five evaluators).
*[3]AVS is an abbreviation for "Acid value of surfactant".
*[4]MABR is an abbreviation for "Moisture absorption blocking rate".

As shown in Table 1, the water-absorbing resin compositions (1) to (36) were smaller in amount of post-degradation-test one-hour eluted soluble component than the comparative water-absorbing resin compositions (1) to (22). Further, individual absorbent bodies (diapers) processed from the water-absorbing resin compositions (1) to (36) had a reduced stickiness by the touch and were also improved in liquid absorbing time (sec) and in re-wet (g).

Further, a comparison between the results in Examples 1 and 2 and the results in Comparative Examples 1 to 4 and a comparison between Examples 7 to 15 and Comparative Examples 7 to 18 show that a combined use of a surfactant and a chelating agent, which is an example method for producing a water-absorbing resin composition in accordance with the present invention, allowed a post-degradation-test one-hour eluted soluble component to be reduced significantly.

This was a surprising result in view of the fact that a surfactant itself has no effect in reducing a post-degradation-test one-hour eluted soluble component.

A comparison between Example 1 and Example 3 indicates that removal of fine powder (second classification) after surface-crosslinking allows the amount of post-degradation-test soluble component to be reduced.

A comparison between Examples 1 and 2 and Examples 4 to 6 indicates that similar effects are produced even though the surfactants are different in type and/or in amount.

A comparison between Example 2 and Examples 7 to 9 indicates that similar effects are produced even though the surfactants are different from each other.

Examples 11 to 16 indicate that similar effects are produced even though at least one of the surfactants and the chelating agents are different in type.

Comparative Example 6 indicates that an excessive amount of surfactant leads to not only a decrease in surface tension but also decreases in urine resistance and in fluid retention capacity under pressure (AAP0.3, AAP0.7, and VDAUP0.3).

Comparative Examples 20 to 22 indicate that none of Patent Literatures 3 to 5 of the background art of the present invention discloses a water-absorbing resin composition in accordance with the present invention.

As described above, the inventors of the present invention have considered the amount of dust (which has not at all been considered in the conventional art as disclosed in each of Patent Literatures 1 to 5) and obtained high urine resistance by controlling the content of water-absorbing resin in dust. A water-absorbing resin composition in accordance with an embodiment of the present invention allows a reduced re-wet, a shortened liquid absorbing time, and a reduced stickiness when used in a diaper in comparison to the water-absorbing resin compositions disclosed in, for example, Patent Literatures 1 to 5, and is thus suitable for actual use. Consequently, the above water-absorbing resin composition provides an excellent sanitary material (disposable diaper in particular).

INDUSTRIAL APPLICABILITY

A water-absorbing resin composition produced by a method in accordance with an embodiment of the present invention is excellent in urine resistance. Such a water-absorbing resin composition is applicable to an absorbent body (e.g., a diaper) which is excellent in fluid retention capacity and has a reduced stickiness.

The invention claimed is:

1. A water-absorbing resin composition comprising (i) a chelating agent and (ii) a surfactant and/or a lubricant, wherein the water-absorbing resin composition has the following properties:
   (1) A centrifuge retention capacity (CRC) being not less than 35 g/g;
   (2) A post-degradation-test one-hour eluted soluble component being not more than 19% by mass;
   (3) An absorbency against pressure 0.7 psi (AAP0.7) being not less than 10 g/g; and
   (4) A content of a water-absorbing resin in dust being not more than 300 ppm with respect to a total mass of the water-absorbing resin composition.

2. The water-absorbing resin composition according to claim 1, comprising:
   the chelating agent in an amount of not less than 0.0001 parts by mass and not more than 1.0 part by mass with respect to 100 parts by mass of the water-absorbing resin composition.

3. The water-absorbing resin composition according to claim 1, wherein
the water-absorbing resin composition has a surface tension of not less than 65 mN/m.

4. The water-absorbing resin composition according to claim 1, wherein
the water-absorbing resin composition has a moisture content of not more than 5% by mass.

5. The water-absorbing resin composition according to claim 1, comprising:
a polyvalent metal salt and/or an inorganic fine particle.

6. The water-absorbing resin composition according to claim 1, wherein
the water-absorbing resin composition has a vertical diffusing absorbency under pressure 0.3 psi (VDAUP0.3) of not less than 10 g/g.

7. The water-absorbing resin composition according to claim 1, wherein
the water-absorbing resin composition includes a surface-eluted soluble component of not more than 2.0% by mass.

8. The water-absorbing resin composition according to claim 1, wherein
a proportion of a particle capable of passing through a classification mesh having a mesh size of 150 μm is not more than 5% by mass with respect to the total mass of the water-absorbing resin composition.

9. The water-absorbing resin composition according to of claim 1, wherein
in a case where a droplet of a 0.9 mass % aqueous sodium chloride solution has been dropped on the water-absorbing resin composition, a contact angle is not more than 90 degrees.

10. The water-absorbing resin composition according to claim 1, wherein
the water-absorbing resin composition is a particulate water-absorbing resin composition including a polyacrylic acid (salt)-based water-absorbing resin particle in an amount within a range of 60 parts by mass to 100 parts by mass with respect to 100 parts by mass as the total mass of the water-absorbing resin composition.

11. A sanitary product, comprising:
a water-absorbing resin composition according to claim 1.

* * * * *